United States Patent
Faridmoayer et al.

(10) Patent No.: US 11,819,544 B2
(45) Date of Patent: *Nov. 21, 2023

(54) IMMUNOGENIC COMPOSITION

(71) Applicant: GLAXOSMITHKLINE BIOLOGICALS SA, Rixensart (BE)

(72) Inventors: Amirreza Faridmoayer, Schlieren (CH); Sabina Marietta Gerber, Schlieren (CH); Stefan Jochen Kemmler, Schlieren (CH)

(73) Assignee: GlaxoSmithKline Biologicals SA, Rixensart (BE)

( * ) Notice: Subject to any disclaimer, the term of this patent is extended or adjusted under 35 U.S.C. 154(b) by 429 days.

This patent is subject to a terminal disclaimer.

(21) Appl. No.: 16/954,337

(22) PCT Filed: Dec. 19, 2018

(86) PCT No.: PCT/EP2018/085857
§ 371 (c)(1),
(2) Date: Jun. 16, 2020

(87) PCT Pub. No.: WO2019/121926
PCT Pub. Date: Jun. 27, 2019

(65) Prior Publication Data
US 2021/0077607 A1    Mar. 18, 2021

(30) Foreign Application Priority Data
Dec. 21, 2017 (GB) .................................. 1721582

(51) Int. Cl.
*A61K 39/085* (2006.01)
*A61K 47/64* (2017.01)
*A61K 39/00* (2006.01)
*C07K 14/31* (2006.01)

(52) U.S. Cl.
CPC .......... *A61K 39/085* (2013.01); *A61K 47/646* (2017.08); *C07K 14/31* (2013.01); *A61K 2039/6068* (2013.01)

(58) Field of Classification Search
None
See application file for complete search history.

(56) References Cited

U.S. PATENT DOCUMENTS 11,426,455 B2 * 8/2022 Bagnoli ............... A61K 39/085

FOREIGN PATENT DOCUMENTS

| BE | 1022565 B1 | 6/2016 |
| WO | 2006119987 A2 | 11/2006 |
| WO | 2011138361 A1 | 11/2011 |
| WO | 2016020499 A2 | 2/2016 |

OTHER PUBLICATIONS

Rudinger J. In: Peptide Hormones. (Ed) JA Parsons, University Park Press, pp. 1-7, 1976.*
Lazar et al. Mol. Cellular Biol. 8: 1247-1252, 1988.*
Greenspan et al. Nature Biotechnology 17:936-937, 1999.*
Skolnick et al. Trends in Biotechnology 18: 34-39, 2000.*
David et al. Clin. Microbiol. Rev. 23: 616-687, 2010.*
International Search Report and Written Opinion in corresponding International Application No. PCT/EP2018/085857 dated Apr. 15, 2019 (15 pages).
Ganesh et al., PLOS Pathogens, vol. 4, issue 11: 1-10 (2008).
Silverman et al., Journal of Biological Chemistry, vol. 291, issue 42: 22001-22010 (2016).
Josefsson et al., PLOS One, vol. 3, issue 5: 1-7 (2008).
Maira-Litran et al., PLOS One, vol. 7, issue 9: 1-9 (2012).
Hssen et al., Microbial Cell Factories, vol. 9, issue 61: 1-13 (2010).
Adamo, Accounts of Chemical Research, vol. 50, issue 5: 1270-1279 (2017).

* cited by examiner

*Primary Examiner* — S. Devi

(57) ABSTRACT

The present invention discloses modified *Staphylococcus aureus* ClfA proteins that contain glycosylation site consensus sequences. The invention also discloses a conjugate comprising a modified ClfA protein and an antigen (for example a *Staphylococcus aureus* saccharide antigen), wherein the antigen is linked (either directly or through a linker) to an amino acid residue of the modified ClfA protein.

15 Claims, 14 Drawing Sheets

Specification includes a Sequence Listing.

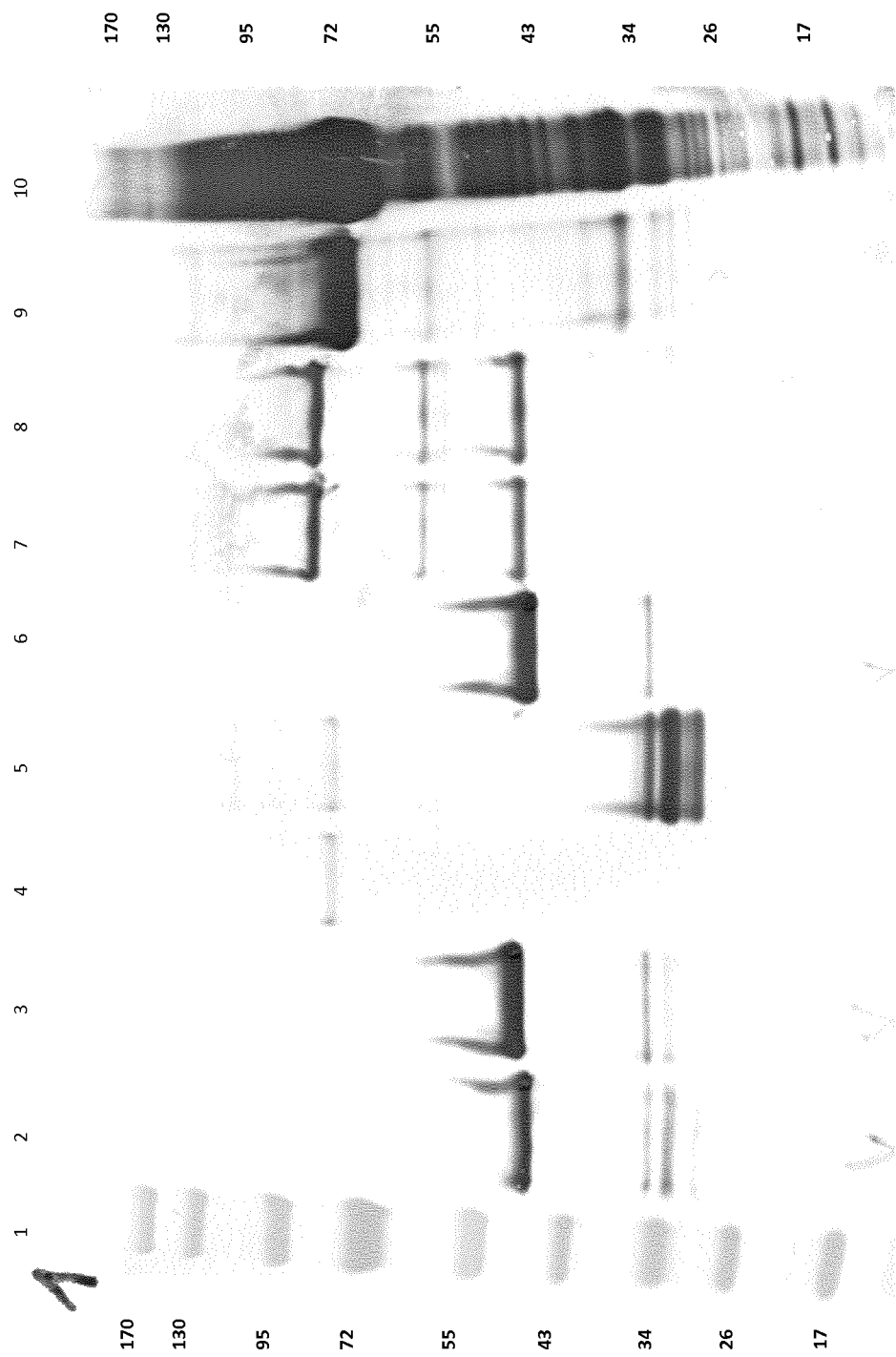

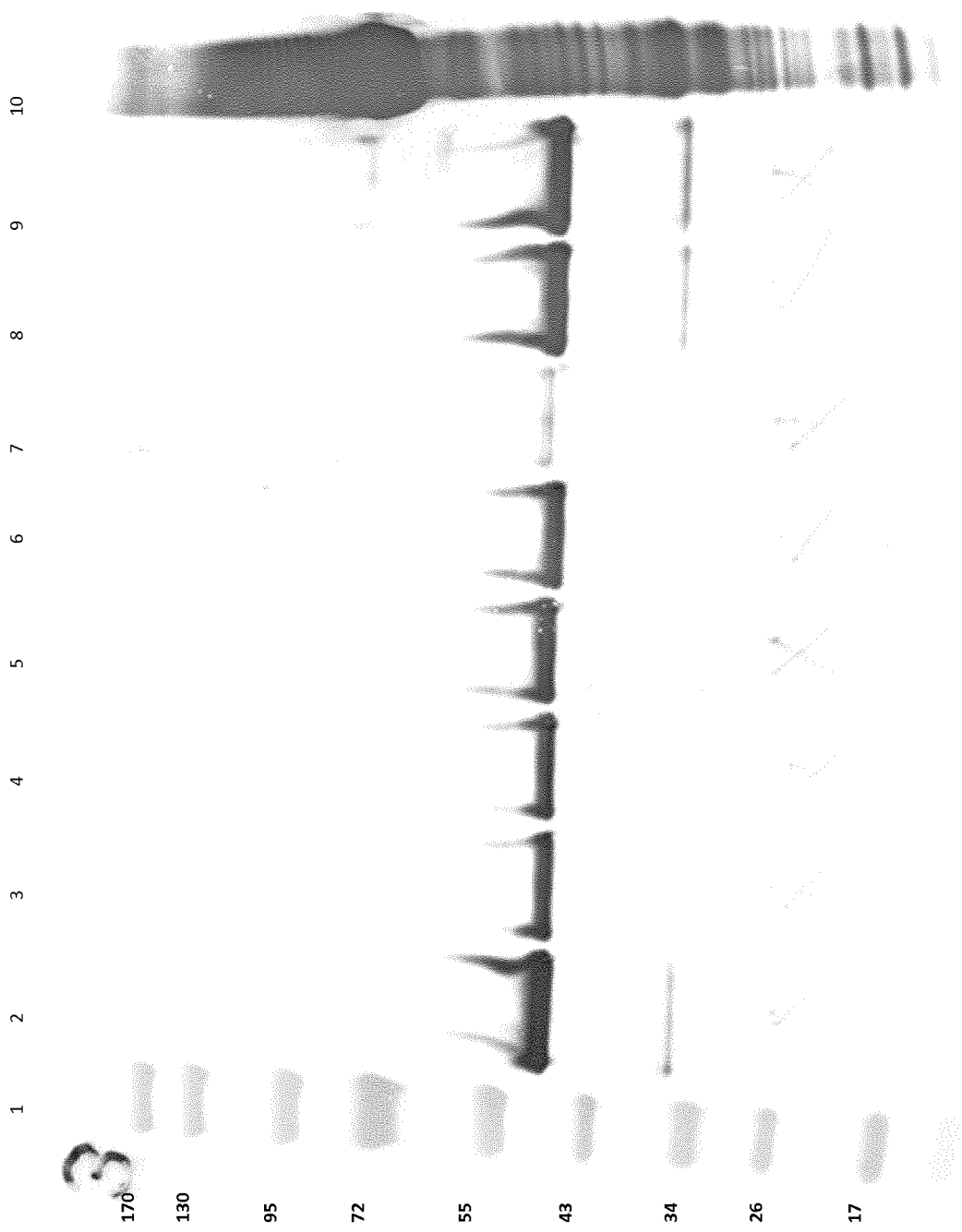

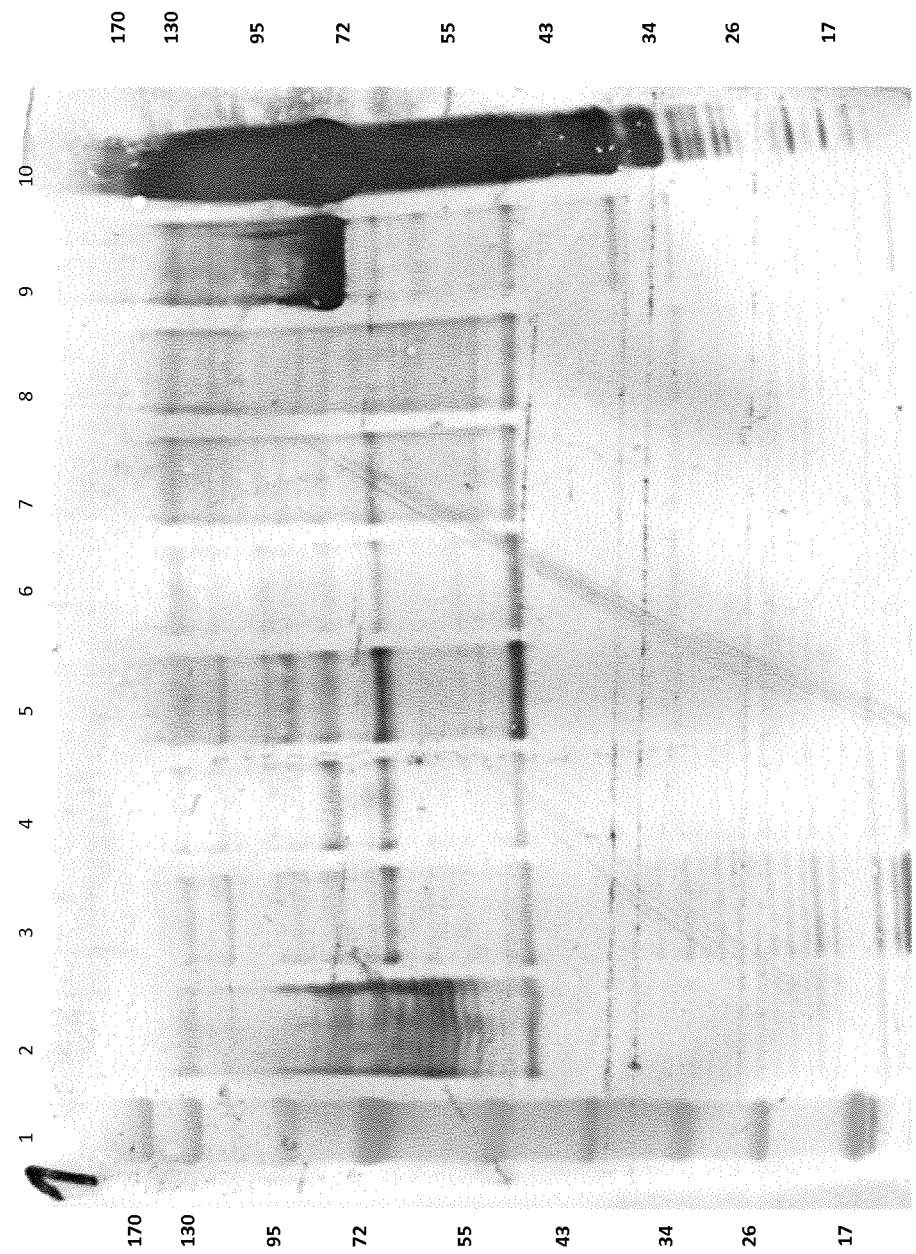

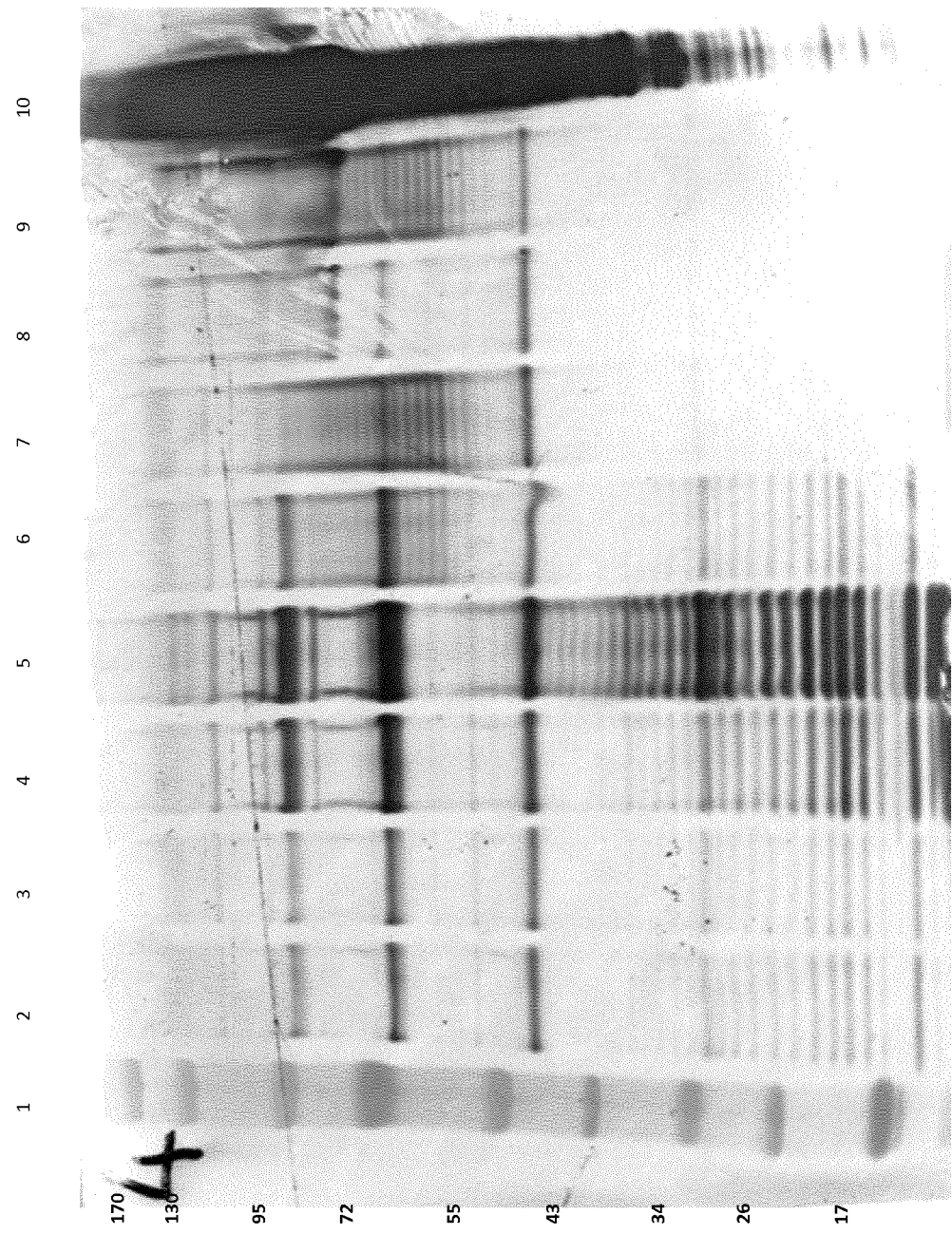

SEQUENCE LISTING

<160> NUMBER OF SEQ ID NOS: 37

<210> SEQ ID NO 1
<211> LENGTH: 560
<212> TYPE: PRT
<213> ORGANISM: Staphylococcus aureus

<400> SEQUENCE: 1

```
Met Asn Met Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Ser Val Ser Ala
        50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
                100                 105                 110

Val Thr Gly Glu Ala Thr Thr Thr Thr Asn Gln Ala Asn Thr Pro
            115                 120                 125

Ala Thr Thr Gln Ser Ser Asn Thr Asn Ala Glu Glu Leu Val Asn Gln
        130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
                180                 185                 190

Ser Thr Asp Ala Ser Asn Lys Asp Val Val Asn Gln Ala Val Asn Thr
            195                 200                 205

Ser Ala Pro Arg Met Arg Ala Phe Ser Leu Ala Ala Val Ala Ala Asp
        210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
            275                 280                 285

Thr Ser Thr Ala Lys Val Pro Pro Ile Met Ala Gly Asp Gln Val Leu
        290                 295                 300

Ala Asn Gly Val Ile Asp Ser Asp Gly Asn Val Ile Tyr Thr Phe Thr
```

```
            305                 310                 315                 320
Asp Tyr Val Asn Thr Lys Asp Val Lys Ala Thr Leu Thr Met Pro
            325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
            355                 360                 365

Tyr Glu Lys Tyr Gly Lys Phe Tyr Asn Leu Ser Ile Lys Gly Thr Ile
            370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
            405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
            450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
            485                 490                 495

Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu Asp
545                 550                 555                 560

<210> SEQ ID NO 2
<211> LENGTH: 522
<212> TYPE: PRT
<213> ORGANISM: Staphylococcus aureus

<400> SEQUENCE: 2

Ala Ser Glu Asn Ser Val Thr Gln Ser Asp Ser Ala Ser Asn Glu Ser
1               5                   10                  15

Lys Ser Asn Asp Ser Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
        35                  40                  45

Thr Ser Val Ala Gln Asn Pro Ala Gln Gln Glu Thr Gln Ser Ser
    50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Gln Ser Ser
            85                  90                  95

Asn Thr Asn Ala Glu Glu Leu Val Asn Gln Thr Ser Asn Glu Thr Thr
            100                 105                 110

Phe Asn Asp Thr Asn Thr Val Ser Ser Val Asn Ser Pro Gln Asn Ser
            115                 120                 125
```

Thr Asn Ala Glu Asn Val Ser Thr Thr Gln Asp Thr Ser Thr Glu Ala
130                 135                 140

Thr Pro Ser Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
                165                 170                 175

Ala Phe Ser Leu Ala Ala Val Ala Ala Asp Ala Pro Ala Ala Gly Thr
            180                 185                 190

Asp Ile Thr Asn Gln Leu Thr Asn Val Thr Val Gly Ile Asp Ser Gly
        195                 200                 205

Thr Thr Val Tyr Pro His Gln Ala Gly Tyr Val Lys Leu Asn Tyr Gly
210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
                245                 250                 255

Pro Pro Ile Met Ala Gly Asp Gln Val Leu Ala Asn Gly Val Ile Asp
            260                 265                 270

Ser Asp Gly Asn Val Ile Tyr Thr Phe Thr Asp Tyr Val Asn Thr Lys
275                 280                 285

Asp Asp Val Lys Ala Thr Leu Thr Met Pro Ala Tyr Ile Asp Pro Glu
290                 295                 300

Asn Val Lys Lys Thr Gly Asn Val Thr Leu Ala Thr Gly Ile Gly Ser
305                 310                 315                 320

Thr Thr Ala Asn Lys Thr Val Leu Val Asp Tyr Glu Lys Tyr Gly Lys
                325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
        355                 360                 365

Val Ile Ala Pro Val Leu Thr Gly Asn Leu Lys Pro Asn Thr Asp Ser
370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
                405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Asp Gln Ile Thr Thr Pro
        435                 440                 445

Tyr Ile Val Val Asn Gly His Ile Asp Pro Asn Ser Lys Gly Asp
450                 455                 460

Leu Ala Leu Arg Ser Thr Leu Tyr Gly Tyr Asn Ser Asn Ile Ile Trp
465                 470                 475                 480

Arg Ser Met Ser Trp Asp Asn Glu Val Ala Phe Asn Asn Gly Ser Gly
                485                 490                 495

Ser Gly Asp Gly Ile Asp Lys Pro Val Val Pro Glu Gln Pro Asp Glu
            500                 505                 510

Pro Gly Glu Ile Glu Pro Ile Pro Glu Asp
        515                 520

<210> SEQ ID NO 3
<211> LENGTH: 340
<212> TYPE: PRT

<213> ORGANISM: Staphylococcus aureus

<400> SEQUENCE: 3

```
Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Val Lys Ala Thr
            100                 105                 110

Leu Thr Met Pro Ala Tyr Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Pro Gly Glu Ile Glu Pro
                325                 330                 335

Ile Pro Glu Asp
            340
```

<210> SEQ ID NO 4
<211> LENGTH: 340
<212> TYPE: PRT
<213> ORGANISM: Artificial Sequence
<220> FEATURE:
<223> OTHER INFORMATION: ClfAN2N3P116S/Y118A

<400> SEQUENCE: 4

Val Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
            35                  40                  45

Ala Val Lys Gly Asp Thr Phe Lys Ile Thr Val Pro Lys Glu Leu Asn
50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
            85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
            115                 120                 125

Asn Val Thr Leu Ala Thr Gly Ile Gly Ser Thr Thr Ala Asn Lys Thr
            130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
            165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
            195                 200                 205

Gln Asn Thr Ser Ile Lys Val Tyr Lys Val Asp Asn Ala Ala Asp Leu
210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
            245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
            275                 280                 285

Leu Tyr Gly Tyr Asn Ser Asn Ile Ile Trp Arg Ser Met Ser Trp Asp
            290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Pro Gly Glu Ile Glu Pro
            325                 330                 335

Ile Pro Glu Asp
            340

<210> SEQ ID NO 5
<211> LENGTH: 360
<212> TYPE: PRT
<213> ORGANISM: Artificial Sequence
<220> FEATURE:
<223> OTHER INFORMATION: ClfAN2N3P116S/Y118A with N-terminal S and Flgl
      signal sequence

<400> SEQUENCE: 5

Met Ile Lys Phe Leu Ser Ala Leu Ile Leu Leu Leu Val Thr Thr Ala

```
  1               5                  10                 15
Ala Gln Ala Ser Val Ala Ala Asp Ala Pro Ala Ala Gly Thr Asp Ile
                20                 25                 30
Thr Asn Gln Leu Thr Asn Val Thr Val Gly Ile Asp Ser Gly Thr Thr
                35                 40                 45
Val Tyr Pro His Gln Ala Gly Tyr Val Lys Leu Asn Tyr Gly Phe Ser
 50                 55                 60
Val Pro Asn Ser Ala Val Lys Gly Asp Thr Phe Lys Ile Thr Val Pro
 65                 70                 75                 80
Lys Glu Leu Asn Leu Asn Gly Val Thr Ser Thr Ala Lys Val Pro Pro
                85                 90                 95
Ile Met Ala Gly Asp Gln Val Leu Ala Asn Gly Val Ile Asp Ser Asp
                100                105                110
Gly Asn Val Ile Tyr Thr Phe Thr Asp Tyr Val Asn Thr Lys Asp Asp
                115                120                125
Val Lys Ala Thr Leu Thr Met Ser Ala Ala Ile Asp Pro Glu Asn Val
                130                135                140
Lys Lys Thr Gly Asn Val Thr Leu Ala Thr Gly Ile Gly Ser Thr Thr
145                150                155                160
Ala Asn Lys Thr Val Leu Val Asp Tyr Glu Lys Tyr Gly Lys Phe Tyr
                165                170                175
Asn Leu Ser Ile Lys Gly Thr Ile Asp Gln Ile Asp Lys Thr Asn Asn
                180                185                190
Thr Tyr Arg Gln Thr Ile Tyr Val Asn Pro Ser Gly Asp Asn Val Ile
                195                200                205
Ala Pro Val Leu Thr Gly Asn Leu Lys Pro Asn Thr Asp Ser Asn Ala
                210                215                220
Leu Ile Asp Gln Gln Asn Thr Ser Ile Lys Val Tyr Lys Val Asp Asn
225                230                235                240
Ala Ala Asp Leu Ser Glu Ser Tyr Phe Val Asn Pro Glu Asn Phe Glu
                245                250                255
Asp Val Thr Asn Ser Val Asn Ile Thr Phe Pro Asn Pro Asn Gln Tyr
                260                265                270
Lys Val Glu Phe Asn Thr Pro Asp Asp Gln Ile Thr Thr Pro Tyr Ile
                275                280                285
Val Val Val Asn Gly His Ile Asp Pro Asn Ser Lys Gly Asp Leu Ala
                290                295                300
Leu Arg Ser Thr Leu Tyr Gly Tyr Asn Ser Asn Ile Ile Trp Arg Ser
305                310                315                320
Met Ser Trp Asp Asn Glu Val Ala Phe Asn Asn Gly Ser Gly Ser Gly
                325                330                335
Asp Gly Ile Asp Lys Pro Val Val Pro Glu Gln Pro Asp Glu Pro Gly
                340                345                350
Glu Ile Glu Pro Ile Pro Glu Asp
                355                360

<210> SEQ ID NO 6
<211> LENGTH: 341
<212> TYPE: PRT
<213> ORGANISM: Artificial Sequence
<220> FEATURE:
<223> OTHER INFORMATION: ClfAN2N3P116S/Y118A with N-terminal S

<400> SEQUENCE: 6

Ser Val Ala Ala Asp Ala Pro Ala Ala Gly Thr Asp Ile Thr Asn Gln
```

```
                1               5                   10                  15
            Leu Thr Asn Val Thr Val Gly Ile Asp Ser Gly Thr Thr Val Tyr Pro
                            20                  25                  30

His Gln Ala Gly Tyr Val Lys Leu Asn Tyr Gly Phe Ser Val Pro Asn
                            35                  40                  45

Ser Ala Val Lys Gly Asp Thr Phe Lys Ile Thr Val Pro Lys Glu Leu
                50                  55                  60

Asn Leu Asn Gly Val Thr Ser Thr Ala Lys Val Pro Pro Ile Met Ala
            65                  70                  75                  80

Gly Asp Gln Val Leu Ala Asn Gly Val Ile Asp Ser Asp Gly Asn Val
                            85                  90                  95

Ile Tyr Thr Phe Thr Asp Tyr Val Asn Thr Lys Asp Val Lys Ala
                            100                 105                 110

Thr Leu Thr Met Ser Ala Ala Ile Asp Pro Glu Asn Val Lys Lys Thr
                            115                 120                 125

Gly Asn Val Thr Leu Ala Thr Gly Ile Gly Ser Thr Thr Ala Asn Lys
                    130                 135                 140

Thr Val Leu Val Asp Tyr Glu Lys Tyr Gly Lys Phe Tyr Asn Leu Ser
            145                 150                 155                 160

Ile Lys Gly Thr Ile Asp Gln Ile Asp Lys Thr Asn Asn Thr Tyr Arg
                            165                 170                 175

Gln Thr Ile Tyr Val Asn Pro Ser Gly Asp Asn Val Ile Ala Pro Val
                            180                 185                 190

Leu Thr Gly Asn Leu Lys Pro Asn Thr Asp Ser Asn Ala Leu Ile Asp
                            195                 200                 205

Gln Gln Asn Thr Ser Ile Lys Val Tyr Lys Val Asp Asn Ala Ala Asp
                    210                 215                 220

Leu Ser Glu Ser Tyr Phe Val Asn Pro Glu Asn Phe Glu Asp Val Thr
            225                 230                 235                 240

Asn Ser Val Asn Ile Thr Phe Pro Asn Pro Asn Gln Tyr Lys Val Glu
                            245                 250                 255

Phe Asn Thr Pro Asp Asp Gln Ile Thr Thr Pro Tyr Ile Val Val Val
                            260                 265                 270

Asn Gly His Ile Asp Pro Asn Ser Lys Gly Asp Leu Ala Leu Arg Ser
                            275                 280                 285

Thr Leu Tyr Gly Tyr Asn Ser Asn Ile Ile Trp Arg Ser Met Ser Trp
                    290                 295                 300

Asp Asn Glu Val Ala Phe Asn Asn Gly Ser Gly Ser Gly Asp Gly Ile
            305                 310                 315                 320

Asp Lys Pro Val Val Pro Glu Gln Pro Asp Glu Pro Gly Glu Ile Glu
                            325                 330                 335

Pro Ile Pro Glu Asp
                    340

<210> SEQ ID NO 7
<211> LENGTH: 528
<212> TYPE: PRT
<213> ORGANISM: Artificial Sequence
<220> FEATURE:
<223> OTHER INFORMATION: Wild-type ClfAN1N2N3 with glycosite at
      position corresponding to mutant 30 (I557 of full-length ClfA)

<400> SEQUENCE: 7

Ala Ser Glu Asn Ser Val Thr Gln Ser Asp Ser Ala Ser Asn Glu Ser
1               5                   10                  15
```

-continued

```
Lys Ser Asn Asp Ser Ser Val Ser Ala Ala Pro Lys Thr Asp Asp
             20              25              30

Thr Asn Val Ser Asp Thr Lys Thr Ser Ser Asn Thr Asn Asn Gly Glu
         35              40              45

Thr Ser Val Ala Gln Asn Pro Ala Gln Gln Glu Thr Thr Gln Ser Ser
 50              55              60

Ser Thr Asn Ala Thr Thr Glu Glu Thr Pro Val Thr Gly Glu Ala Thr
 65              70              75              80

Thr Thr Thr Thr Asn Gln Ala Asn Thr Pro Ala Thr Thr Gln Ser Ser
             85              90              95

Asn Thr Asn Ala Glu Glu Leu Val Asn Gln Thr Ser Asn Glu Thr Thr
                 100             105             110

Phe Asn Asp Thr Asn Thr Val Ser Ser Val Asn Ser Pro Gln Asn Ser
         115             120             125

Thr Asn Ala Glu Asn Val Ser Thr Thr Gln Asp Thr Ser Thr Glu Ala
 130             135             140

Thr Pro Ser Asn Glu Ser Ala Pro Gln Ser Thr Asp Ala Ser Asn
145             150             155             160

Lys Asp Val Val Asn Gln Ala Val Asn Thr Ser Ala Pro Arg Met Arg
                 165             170             175

Ala Phe Ser Leu Ala Ala Val Ala Ala Asp Ala Pro Ala Ala Gly Thr
         180             185             190

Asp Ile Thr Asn Gln Leu Thr Asn Val Thr Val Gly Ile Asp Ser Gly
             195             200             205

Thr Thr Val Tyr Pro His Gln Ala Gly Tyr Val Lys Leu Asn Tyr Gly
 210             215             220

Phe Ser Val Pro Asn Ser Ala Val Lys Gly Asp Thr Phe Lys Ile Thr
225             230             235             240

Val Pro Lys Glu Leu Asn Leu Asn Gly Val Thr Ser Thr Ala Lys Val
                 245             250             255

Pro Pro Ile Met Ala Gly Asp Gln Val Leu Ala Asn Gly Val Ile Asp
         260             265             270

Ser Asp Gly Asn Val Ile Tyr Thr Phe Thr Asp Tyr Val Asn Thr Lys
             275             280             285

Asp Asp Val Lys Ala Thr Leu Thr Met Pro Ala Tyr Ile Asp Pro Glu
 290             295             300

Asn Val Lys Lys Thr Gly Asn Val Thr Leu Ala Thr Gly Ile Gly Ser
305             310             315             320

Thr Thr Ala Asn Lys Thr Val Leu Val Asp Tyr Glu Lys Tyr Gly Lys
                 325             330             335

Phe Tyr Asn Leu Ser Ile Lys Gly Thr Ile Asp Gln Ile Asp Lys Thr
         340             345             350

Asn Asn Thr Tyr Arg Gln Thr Ile Tyr Val Asn Pro Ser Gly Asp Asn
             355             360             365

Val Ile Ala Pro Val Leu Thr Gly Asn Leu Lys Pro Asn Thr Asp Ser
 370             375             380

Asn Ala Leu Ile Asp Gln Gln Asn Thr Ser Ile Lys Val Tyr Lys Val
385             390             395             400

Asp Asn Ala Ala Asp Leu Ser Glu Ser Tyr Phe Val Asn Pro Glu Asn
                 405             410             415

Phe Glu Asp Val Thr Asn Ser Val Asn Ile Thr Phe Pro Asn Pro Asn
         420             425             430

Gln Tyr Lys Val Glu Phe Asn Thr Pro Asp Asp Gln Ile Thr Thr Pro
```

```
            435                 440                 445
Tyr Ile Val Val Asn Gly His Ile Asp Pro Asn Ser Lys Gly Asp
    450                 455                 460

Leu Ala Leu Arg Ser Thr Leu Tyr Gly Tyr Asn Ser Asn Ile Ile Trp
465                 470                 475                 480

Arg Ser Met Ser Trp Asp Asn Glu Val Ala Phe Asn Asn Gly Ser Gly
                485                 490                 495

Ser Gly Asp Gly Ile Asp Lys Pro Val Val Pro Glu Gln Pro Asp Glu
            500                 505                 510

Pro Gly Glu Ile Glu Pro Lys Asp Gln Asn Ala Thr Lys Pro Glu Asp
            515                 520                 525

<210> SEQ ID NO 8
<211> LENGTH: 528
<212> TYPE: PRT
<213> ORGANISM: Artificial Sequence
<220> FEATURE:
<223> OTHER INFORMATION: ClfAN1N2N3 P298S/Y300A with glycosite at
      position corresponding to mutant 30 (I557 of full-length ClfA)

<400> SEQUENCE: 8

Ala Ser Glu Asn Ser Val Thr Gln Ser Asp Ser Ala Ser Asn Glu Ser
1               5                   10                  15

Lys Ser Asn Asp Ser Ser Val Ser Ala Ala Pro Lys Thr Asp Asp
            20                  25                  30

Thr Asn Val Ser Asp Thr Lys Thr Ser Ser Asn Thr Asn Asn Gly Glu
        35                  40                  45

Thr Ser Val Ala Gln Asn Pro Ala Gln Gln Glu Thr Thr Gln Ser Ser
    50                  55                  60

Ser Thr Asn Ala Thr Thr Glu Glu Thr Pro Val Thr Gly Glu Ala Thr
65                  70                  75                  80

Thr Thr Thr Thr Asn Gln Ala Asn Thr Pro Ala Thr Thr Gln Ser Ser
                85                  90                  95

Asn Thr Asn Ala Glu Glu Leu Val Asn Gln Thr Ser Asn Glu Thr Thr
            100                 105                 110

Phe Asn Asp Thr Asn Thr Val Ser Ser Val Asn Ser Pro Gln Asn Ser
        115                 120                 125

Thr Asn Ala Glu Asn Val Ser Thr Thr Gln Asp Thr Ser Thr Glu Ala
130                 135                 140

Thr Pro Ser Asn Asn Glu Ser Ala Pro Gln Ser Thr Asp Ala Ser Asn
145                 150                 155                 160

Lys Asp Val Val Asn Gln Ala Val Asn Thr Ser Ala Pro Arg Met Arg
                165                 170                 175

Ala Phe Ser Leu Ala Ala Val Ala Ala Asp Ala Pro Ala Ala Gly Thr
            180                 185                 190

Asp Ile Thr Asn Gln Leu Thr Asn Val Thr Val Gly Ile Asp Ser Gly
        195                 200                 205

Thr Thr Val Tyr Pro His Gln Ala Gly Tyr Val Lys Leu Asn Tyr Gly
    210                 215                 220

Phe Ser Val Pro Asn Ser Ala Val Lys Gly Asp Thr Phe Lys Ile Thr
225                 230                 235                 240

Val Pro Lys Glu Leu Asn Leu Asn Gly Val Thr Ser Thr Ala Lys Val
                245                 250                 255

Pro Pro Ile Met Ala Gly Asp Gln Val Leu Ala Asn Gly Val Ile Asp
            260                 265                 270
```

Ser Asp Gly Asn Val Ile Tyr Thr Phe Thr Asp Tyr Val Asn Thr Lys
            275                 280                 285

Asp Asp Val Lys Ala Thr Leu Thr Met Ser Ala Ala Ile Asp Pro Glu
        290                 295                 300

Asn Val Lys Lys Thr Gly Asn Val Thr Leu Ala Thr Gly Ile Gly Ser
305                 310                 315                 320

Thr Thr Ala Asn Lys Thr Val Leu Val Asp Tyr Glu Lys Tyr Gly Lys
                325                 330                 335

Phe Tyr Asn Leu Ser Ile Lys Gly Thr Ile Asp Gln Ile Asp Lys Thr
            340                 345                 350

Asn Asn Thr Tyr Arg Gln Thr Ile Tyr Val Asn Pro Ser Gly Asp Asn
        355                 360                 365

Val Ile Ala Pro Val Leu Thr Gly Asn Leu Lys Pro Asn Thr Asp Ser
370                 375                 380

Asn Ala Leu Ile Asp Gln Gln Asn Thr Ser Ile Lys Val Tyr Lys Val
385                 390                 395                 400

Asp Asn Ala Ala Asp Leu Ser Glu Ser Tyr Phe Val Asn Pro Glu Asn
                405                 410                 415

Phe Glu Asp Val Thr Asn Ser Val Asn Ile Thr Phe Pro Asn Pro Asn
            420                 425                 430

Gln Tyr Lys Val Glu Phe Asn Thr Pro Asp Gln Ile Thr Thr Pro
        435                 440                 445

Tyr Ile Val Val Asn Gly His Ile Asp Pro Asn Ser Lys Gly Asp
            450                 455                 460

Leu Ala Leu Arg Ser Thr Leu Tyr Gly Tyr Asn Ser Asn Ile Ile Trp
465                 470                 475                 480

Arg Ser Met Ser Trp Asp Asn Glu Val Ala Phe Asn Asn Gly Ser Gly
                485                 490                 495

Ser Gly Asp Gly Ile Asp Lys Pro Val Val Pro Glu Gln Pro Asp Glu
            500                 505                 510

Pro Gly Glu Ile Glu Pro Lys Asp Gln Asn Ala Thr Lys Pro Glu Asp
        515                 520                 525

<210> SEQ ID NO 9
<211> LENGTH: 346
<212> TYPE: PRT
<213> ORGANISM: Artificial Sequence
<220> FEATURE:
<223> OTHER INFORMATION: Wild-type ClfAN2N3 with mutant 30 glycosite

<400> SEQUENCE: 9

Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

-continued

```
Leu Thr Met Pro Ala Tyr Ile Asp Pro Glu Asn Val Lys Lys Thr Gly
            115                 120                 125
Asn Val Thr Leu Ala Thr Gly Ile Gly Ser Thr Thr Ala Asn Lys Thr
        130                 135                 140
Val Leu Val Asp Tyr Glu Lys Tyr Gly Lys Phe Tyr Asn Leu Ser Ile
145                 150                 155                 160
Lys Gly Thr Ile Asp Gln Ile Asp Lys Thr Asn Asn Thr Tyr Arg Gln
                165                 170                 175
Thr Ile Tyr Val Asn Pro Ser Gly Asp Asn Val Ile Ala Pro Val Leu
            180                 185                 190
Thr Gly Asn Leu Lys Pro Asn Thr Asp Ser Asn Ala Leu Ile Asp Gln
        195                 200                 205
Gln Asn Thr Ser Ile Lys Val Tyr Lys Val Asp Asn Ala Ala Asp Leu
    210                 215                 220
Ser Glu Ser Tyr Phe Val Asn Pro Glu Asn Phe Glu Asp Val Thr Asn
225                 230                 235                 240
Ser Val Asn Ile Thr Phe Pro Asn Pro Asn Gln Tyr Lys Val Glu Phe
                245                 250                 255
Asn Thr Pro Asp Asp Gln Ile Thr Thr Pro Tyr Ile Val Val Asn
            260                 265                 270
Gly His Ile Asp Pro Asn Ser Lys Gly Asp Leu Ala Leu Arg Ser Thr
        275                 280                 285
Leu Tyr Gly Tyr Asn Ser Asn Ile Ile Trp Arg Ser Met Ser Trp Asp
    290                 295                 300
Asn Glu Val Ala Phe Asn Asn Gly Ser Gly Ser Gly Asp Gly Ile Asp
305                 310                 315                 320
Lys Pro Val Val Pro Glu Gln Pro Asp Glu Pro Gly Glu Ile Glu Pro
                325                 330                 335
Lys Asp Gln Asn Ala Thr Lys Pro Glu Asp
            340                 345

<210> SEQ ID NO 10
<211> LENGTH: 346
<212> TYPE: PRT
<213> ORGANISM: Artificial Sequence
<220> FEATURE:
<223> OTHER INFORMATION: ClfAN2N3P116S/Y118A with mutant 30 glycosite

<400> SEQUENCE: 10

Val Ala Ala Asp Ala Pro Ala Ala Gly Thr Asp Ile Thr Asn Gln Leu
1               5                   10                  15
Thr Asn Val Thr Val Gly Ile Asp Ser Gly Thr Thr Val Tyr Pro His
                20                  25                  30
Gln Ala Gly Tyr Val Lys Leu Asn Tyr Gly Phe Ser Val Pro Asn Ser
            35                  40                  45
Ala Val Lys Gly Asp Thr Phe Lys Ile Thr Val Pro Lys Glu Leu Asn
        50                  55                  60
Leu Asn Gly Val Thr Ser Thr Ala Lys Val Pro Pro Ile Met Ala Gly
65                  70                  75                  80
Asp Gln Val Leu Ala Asn Gly Val Ile Asp Ser Asp Gly Asn Val Ile
                85                  90                  95
Tyr Thr Phe Thr Asp Tyr Val Asn Thr Lys Asp Asp Val Lys Ala Thr
            100                 105                 110
Leu Thr Met Ser Ala Ala Ile Asp Pro Glu Asn Val Lys Lys Thr Gly
            115                 120                 125
```

```
Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
                180                 185                 190

Thr Gly Asn Leu Lys Pro Asn Thr Asp Ser Asn Ala Leu Ile Asp Gln
            195                 200                 205

Gln Asn Thr Ser Ile Lys Val Tyr Lys Val Asp Asn Ala Ala Asp Leu
        210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
                260                 265                 270

Gly His Ile Asp Pro Asn Ser Lys Gly Asp Leu Ala Leu Arg Ser Thr
            275                 280                 285

Leu Tyr Gly Tyr Asn Ser Asn Ile Ile Trp Arg Ser Met Ser Trp Asp
290                 295                 300

Asn Glu Val Ala Phe Asn Asn Gly Ser Gly Ser Asp Gly Ile Asp
305                 310                 315                 320

Lys Pro Val Val Pro Glu Gln Pro Asp Glu Pro Gly Glu Ile Glu Pro
                325                 330                 335

Lys Asp Gln Asn Ala Thr Lys Pro Glu Asp
            340                 345
```

<210> SEQ ID NO 11
<211> LENGTH: 366
<212> TYPE: PRT
<213> ORGANISM: Artificial Sequence
<220> FEATURE:
<223> OTHER INFORMATION: ClfAN2N3P116S/Y118A with N-terminal S and FlgI
      signal sequence and mutant 30 glycosite

<400> SEQUENCE: 11

```
Met Ile Lys Phe Leu Ser Ala Leu Ile Leu Leu Leu Val Thr Thr Ala
1               5                   10                  15

Ala Gln Ala Ser Val Ala Ala Asp Ala Pro Ala Ala Gly Thr Asp Ile
            20                  25                  30

Thr Asn Gln Leu Thr Asn Val Thr Val Gly Ile Asp Ser Gly Thr Thr
        35                  40                  45

Val Tyr Pro His Gln Ala Gly Tyr Val Lys Leu Asn Tyr Gly Phe Ser
50                  55                  60

Val Pro Asn Ser Ala Val Lys Gly Asp Thr Phe Lys Ile Thr Val Pro
65                  70                  75                  80

Lys Glu Leu Asn Leu Asn Gly Val Thr Ser Thr Ala Lys Val Pro Pro
                85                  90                  95

Ile Met Ala Gly Asp Gln Val Leu Ala Asn Gly Val Ile Asp Ser Asp
            100                 105                 110

Gly Asn Val Ile Tyr Thr Phe Thr Asp Tyr Val Asn Thr Lys Asp Asp
        115                 120                 125

Val Lys Ala Thr Leu Thr Met Ser Ala Ala Ile Asp Pro Glu Asn Val
130                 135                 140
```

```
Lys Lys Thr Gly Asn Val Thr Leu Ala Thr Gly Ile Gly Ser Thr Thr
145                 150                 155                 160

Ala Asn Lys Thr Val Leu Val Asp Tyr Glu Lys Tyr Gly Lys Phe Tyr
                165                 170                 175

Asn Leu Ser Ile Lys Gly Thr Ile Asp Gln Ile Asp Lys Thr Asn Asn
            180                 185                 190

Thr Tyr Arg Gln Thr Ile Tyr Val Asn Pro Ser Gly Asp Asn Val Ile
            195                 200                 205

Ala Pro Val Leu Thr Gly Asn Leu Lys Pro Asn Thr Asp Ser Asn Ala
        210                 215                 220

Leu Ile Asp Gln Gln Asn Thr Ser Ile Lys Val Tyr Lys Val Asp Asn
225                 230                 235                 240

Ala Ala Asp Leu Ser Glu Ser Tyr Phe Val Asn Pro Glu Asn Phe Glu
                245                 250                 255

Asp Val Thr Asn Ser Val Asn Ile Thr Phe Pro Asn Pro Asn Gln Tyr
            260                 265                 270

Lys Val Glu Phe Asn Thr Pro Asp Asp Gln Ile Thr Thr Pro Tyr Ile
            275                 280                 285

Val Val Val Asn Gly His Ile Asp Pro Asn Ser Lys Gly Asp Leu Ala
        290                 295                 300

Leu Arg Ser Thr Leu Tyr Gly Tyr Asn Ser Asn Ile Ile Trp Arg Ser
305                 310                 315                 320

Met Ser Trp Asp Asn Glu Val Ala Phe Asn Asn Gly Ser Gly Ser Gly
                325                 330                 335

Asp Gly Ile Asp Lys Pro Val Val Pro Glu Gln Pro Asp Glu Pro Gly
            340                 345                 350

Glu Ile Glu Pro Lys Asp Gln Asn Ala Thr Lys Pro Glu Asp
        355                 360                 365

<210> SEQ ID NO 12
<211> LENGTH: 347
<212> TYPE: PRT
<213> ORGANISM: Artificial Sequence
<220> FEATURE:
<223> OTHER INFORMATION: ClfAN2N3P116S/Y118A with N-terminal S and
      mutant 30 glycosite

<400> SEQUENCE: 12

Ser Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
            20                  25                  30

His Gln Ala Gly Tyr Val Lys Leu Asn Tyr Gly Phe Ser Val Pro Asn
                35                  40                  45

Ser Ala Val Lys Gly Asp Thr Phe Lys Ile Thr Val Pro Lys Glu Leu
50                  55                  60

Asn Leu Asn Gly Val Thr Ser Thr Ala Lys Val Pro Pro Ile Met Ala
65                  70                  75                  80

Gly Asp Gln Val Leu Ala Asn Gly Val Ile Asp Ser Asp Gly Asn Val
            85                  90                  95

Ile Tyr Thr Phe Thr Asp Tyr Val Asn Thr Lys Asp Asp Val Lys Ala
                100                 105                 110

Thr Leu Thr Met Ser Ala Ala Ile Asp Pro Glu Asn Val Lys Lys Thr
            115                 120                 125

Gly Asn Val Thr Leu Ala Thr Gly Ile Gly Ser Thr Thr Ala Asn Lys
```

```
            130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Asn Thr Tyr Arg
                165                 170                 175

Gln Thr Ile Tyr Val Asn Pro Ser Gly Asp Asn Val Ile Ala Pro Val
            180                 185                 190

Leu Thr Gly Asn Leu Lys Pro Asn Thr Asp Ser Asn Ala Leu Ile Asp
        195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
                245                 250                 255

Phe Asn Thr Pro Asp Asp Gln Ile Thr Thr Pro Tyr Ile Val Val Val
            260                 265                 270

Asn Gly His Ile Asp Pro Asn Ser Lys Gly Asp Leu Ala Leu Arg Ser
        275                 280                 285

Thr Leu Tyr Gly Tyr Asn Ser Asn Ile Ile Trp Arg Ser Met Ser Trp
    290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu
                325                 330                 335

Pro Lys Asp Gln Asn Ala Thr Lys Pro Glu Asp
            340                 345

<210> SEQ ID NO 13
<211> LENGTH: 19
<212> TYPE: PRT
<213> ORGANISM: Escherichia coli

<400> SEQUENCE: 13

Met Ile Lys Phe Leu Ser Ala Leu Ile Leu Leu Val Thr Thr Ala
1               5                   10                  15

Ala Gln Ala

<210> SEQ ID NO 14
<211> LENGTH: 21
<212> TYPE: PRT
<213> ORGANISM: Escherichia coli

<400> SEQUENCE: 14

Met Lys Lys Thr Ala Ile Ala Ile Ala Val Ala Leu Ala Gly Phe Ala
1               5                   10                  15

Thr Val Ala Gln Ala
            20

<210> SEQ ID NO 15
<211> LENGTH: 26
<212> TYPE: PRT
<213> ORGANISM: Escherichia coli

<400> SEQUENCE: 15

Met Lys Ile Lys Thr Gly Ala Arg Ile Leu Ala Leu Ser Ala Leu Thr
1               5                   10                  15
```

```
Thr Met Met Phe Ser Ala Ser Ala Leu Ala
        20                  25

<210> SEQ ID NO 16
<211> LENGTH: 22
<212> TYPE: PRT
<213> ORGANISM: Erwinia carotovora

<400> SEQUENCE: 16

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 17
<211> LENGTH: 23
<212> TYPE: PRT
<213> ORGANISM: Escherichia coli

<400> SEQUENCE: 17

Met Ser Phe Lys Lys Ile Ile Lys Ala Phe Val Ile Met Ala Ala Leu
1               5                   10                  15

Val Ser Val Gln Ala His Ala
            20

<210> SEQ ID NO 18
<211> LENGTH: 19
<212> TYPE: PRT
<213> ORGANISM: Escherichia coli

<400> SEQUENCE: 18

Met Lys Lys Ile Trp Leu Ala Leu Ala Gly Leu Val Leu Ala Phe Ser
1               5                   10                  15

Ala Ser Ala

<210> SEQ ID NO 19
<211> LENGTH: 21
<212> TYPE: PRT
<213> ORGANISM: Escherichia coli

<400> SEQUENCE: 19

Met Lys Gln Ala Leu Arg Val Ala Phe Gly Phe Leu Ile Leu Trp Ala
1               5                   10                  15

Ser Val Leu His Ala
            20

<210> SEQ ID NO 20
<211> LENGTH: 26
<212> TYPE: PRT
<213> ORGANISM: Escherichia coli

<400> SEQUENCE: 20

Met Lys Met Asn Lys Lys Val Leu Leu Thr Ser Thr Met Ala Ala Ser
1               5                   10                  15

Leu Leu Ser Val Ala Ser Val Gln Ala Ser
            20                  25

<210> SEQ ID NO 21
<211> LENGTH: 5
<212> TYPE: PRT
<213> ORGANISM: Artificial Sequence
<220> FEATURE:
<223> OTHER INFORMATION: glycosite
```

```
<220> FEATURE:
<221> NAME/KEY: MOD_RES
<222> LOCATION: (1)..(1)
<223> OTHER INFORMATION: Xaa can be Asp or Glu
<220> FEATURE:
<221> NAME/KEY: MOD_RES
<222> LOCATION: (2)..(2)
<223> OTHER INFORMATION: Xaa can be any naturally occurring amino acid
      except proline
<220> FEATURE:
<221> NAME/KEY: MOD_RES
<222> LOCATION: (4)..(4)
<223> OTHER INFORMATION: Xaa can be any naturally occurring amino acid
      except proline
<220> FEATURE:
<221> NAME/KEY: MOD_RES
<222> LOCATION: (5)..(5)
<223> OTHER INFORMATION: Xaa can be Ser or Thr

<400> SEQUENCE: 21

Xaa Xaa Asn Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: glycosite
<220> FEATURE:
<221> NAME/KEY: MOD_RES
<222> LOCATION: (2)..(2)
<223> OTHER INFORMATION: Xaa can be Asp or Glu
<220> FEATURE:
<221> NAME/KEY: MOD_RES
<222> LOCATION: (3)..(3)
<223> OTHER INFORMATION: Xaa can be any naturally occurring amino acid
      except proline
<220> FEATURE:
<221> NAME/KEY: MOD_RES
<222> LOCATION: (5)..(5)
<223> OTHER INFORMATION: Xaa can be any naturally occurring amino acid
      except proline
<220> FEATURE:
<221> NAME/KEY: MOD_RES
<222> LOCATION: (6)..(6)
<223> OTHER INFORMATION: Xaa can be Ser or Thr

<400> SEQUENCE: 22

Lys Xaa Xaa Asn Xaa Xaa Lys
1               5

<210> SEQ ID NO 23
<211> LENGTH: 7
<212> TYPE: PRT
<213> ORGANISM: Artificial Sequence
<220> FEATURE:
<223> OTHER INFORMATION: glycosite

<400> SEQUENCE: 23

Lys Asp Gln Asn Ala Thr Lys
1               5

<210> SEQ ID NO 24
<211> LENGTH: 7
<212> TYPE: PRT
<213> ORGANISM: Artificial Sequence
<220> FEATURE:
<223> OTHER INFORMATION: glycosite

<400> SEQUENCE: 24

Lys Asp Gln Asn Arg Thr Lys
```

<210> SEQ ID NO 25
<211> LENGTH: 354
<212> TYPE: PRT
<213> ORGANISM: Artificial Sequence
<220> FEATURE:
<223> OTHER INFORMATION: ClfAN2N3P116S/Y118A with mutant 30 glycosite, additional GS and 6-His C-terminal tag

<400> SEQUENCE: 25

```
Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Pro Gly Glu Ile Glu Pro
                325                 330                 335

Lys Asp Gln Asn Ala Thr Lys Pro Glu Asp Gly Ser His His His His
            340                 345                 350
```

His His

<210> SEQ ID NO 26
<211> LENGTH: 374
<212> TYPE: PRT
<213> ORGANISM: Artificial Sequence
<220> FEATURE:
<223> OTHER INFORMATION: ClfAN2N3P116S/Y118A with N-terminal S and FlgI
    signal sequence and mutant 30 glycosite, additional GS and 6-His
    C-terminal tag

<400> SEQUENCE: 26

```
Met Ile Lys Phe Leu Ser Ala Leu Ile Leu Leu Val Thr Thr Ala
1               5                   10                  15

Ala Gln Ala Ser Val Ala Ala Asp Ala Pro Ala Ala Gly Thr Asp Ile
            20                  25                  30

Thr Asn Gln Leu Thr Asn Val Thr Val Gly Ile Asp Ser Gly Thr Thr
            35                  40                  45

Val Tyr Pro His Gln Ala Gly Tyr Val Lys Leu Asn Tyr Gly Phe Ser
50                  55                  60

Val Pro Asn Ser Ala Val Lys Gly Asp Thr Phe Lys Ile Thr Val Pro
65                  70                  75                  80

Lys Glu Leu Asn Leu Asn Gly Val Thr Ser Thr Ala Lys Val Pro Pro
                85                  90                  95

Ile Met Ala Gly Asp Gln Val Leu Ala Asn Gly Val Ile Asp Ser Asp
            100                 105                 110

Gly Asn Val Ile Tyr Thr Phe Thr Asp Tyr Val Asn Thr Lys Asp Asp
            115                 120                 125

Val Lys Ala Thr Leu Thr Met Ser Ala Ala Ile Asp Pro Glu Asn Val
130                 135                 140

Lys Lys Thr Gly Asn Val Thr Leu Ala Thr Gly Ile Gly Ser Thr Thr
145                 150                 155                 160

Ala Asn Lys Thr Val Leu Val Asp Tyr Glu Lys Tyr Gly Lys Phe Tyr
                165                 170                 175

Asn Leu Ser Ile Lys Gly Thr Ile Asp Gln Ile Asp Lys Thr Asn Asn
            180                 185                 190

Thr Tyr Arg Gln Thr Ile Tyr Val Asn Pro Ser Gly Asp Asn Val Ile
            195                 200                 205

Ala Pro Val Leu Thr Gly Asn Leu Lys Pro Asn Thr Asp Ser Asn Ala
210                 215                 220

Leu Ile Asp Gln Gln Asn Thr Ser Ile Lys Val Tyr Lys Val Asp Asn
225                 230                 235                 240

Ala Ala Asp Leu Ser Glu Ser Tyr Phe Val Asn Pro Glu Asn Phe Glu
                245                 250                 255

Asp Val Thr Asn Ser Val Asn Ile Thr Phe Pro Asn Pro Gln Tyr
            260                 265                 270

Lys Val Glu Phe Asn Thr Pro Asp Asp Gln Ile Thr Thr Pro Tyr Ile
            275                 280                 285

Val Val Val Asn Gly His Ile Asp Pro Asn Ser Lys Gly Asp Leu Ala
290                 295                 300

Leu Arg Ser Thr Leu Tyr Gly Tyr Asn Ser Asn Ile Ile Trp Arg Ser
305                 310                 315                 320

Met Ser Trp Asp Asn Glu Val Ala Phe Asn Asn Gly Ser Gly Ser Gly
                325                 330                 335

Asp Gly Ile Asp Lys Pro Val Val Pro Glu Gln Pro Asp Glu Pro Gly
            340                 345                 350
```

Glu Ile Glu Pro Lys Asp Gln Asn Ala Thr Lys Pro Glu Asp Gly Ser
            355                 360                 365

His His His His His His
    370

<210> SEQ ID NO 27
<211> LENGTH: 355
<212> TYPE: PRT
<213> ORGANISM: Artificial Sequence
<220> FEATURE:
<223> OTHER INFORMATION: ClfAN2N3P116S/Y118A with N-terminal S,
      glycosite, additional GS and 6-His C-terminal tag

<400> SEQUENCE: 27

Ser Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
            20                  25                  30

His Gln Ala Gly Tyr Val Lys Leu Asn Tyr Gly Phe Ser Val Pro Asn
        35                  40                  45

Ser Ala Val Lys Gly Asp Thr Phe Lys Ile Thr Val Pro Lys Glu Leu
50                  55                  60

Asn Leu Asn Gly Val Thr Ser Thr Ala Lys Val Pro Pro Ile Met Ala
65                  70                  75                  80

Gly Asp Gln Val Leu Ala Asn Gly Val Ile Asp Ser Asp Gly Asn Val
                85                  90                  95

Ile Tyr Thr Phe Thr Asp Tyr Val Asn Thr Lys Asp Asp Val Lys Ala
            100                 105                 110

Thr Leu Thr Met Ser Ala Ala Ile Asp Pro Glu Asn Val Lys Lys Thr
        115                 120                 125

Gly Asn Val Thr Leu Ala Thr Gly Ile Gly Ser Thr Thr Ala Asn Lys
130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Asn Thr Tyr Arg
                165                 170                 175

Gln Thr Ile Tyr Val Asn Pro Ser Gly Asp Asn Val Ile Ala Pro Val
            180                 185                 190

Leu Thr Gly Asn Leu Lys Pro Asn Thr Asp Ser Asn Ala Leu Ile Asp
        195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
                245                 250                 255

Phe Asn Thr Pro Asp Asp Gln Ile Thr Thr Pro Tyr Ile Val Val Val
            260                 265                 270

Asn Gly His Ile Asp Pro Asn Ser Lys Gly Asp Leu Ala Leu Arg Ser
        275                 280                 285

Thr Leu Tyr Gly Tyr Asn Ser Asn Ile Ile Trp Arg Ser Met Ser Trp
    290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu

```
                    325                 330                 335
Pro Lys Asp Gln Asn Ala Thr Lys Pro Glu Asp Gly Ser His His His
                340                 345                 350

His His His
        355

<210> SEQ ID NO 28
<211> LENGTH: 346
<212> TYPE: PRT
<213> ORGANISM: Artificial Sequence
<220> FEATURE:
<223> OTHER INFORMATION: ClfAN2N3P116S/Y118A mutant 1

<400> SEQUENCE: 28

Val Ala Ala Asp Ala Pro Ala Ala Gly Thr Asp Ile Thr Asn Gln Leu
1               5                   10                  15

Thr Asn Val Thr Val Gly Ile Lys Asp Gln Asn Ala Thr Lys Ser Gly
                20                  25                  30

Thr Thr Val Tyr Pro His Gln Ala Gly Tyr Val Lys Leu Asn Tyr Gly
            35                  40                  45

Phe Ser Val Pro Asn Ser Ala Val Lys Gly Asp Thr Phe Lys Ile Thr
50                  55                  60

Val Pro Lys Glu Leu Asn Leu Asn Gly Val Thr Ser Thr Ala Lys Val
65                  70                  75                  80

Pro Pro Ile Met Ala Gly Asp Gln Val Leu Ala Asn Gly Val Ile Asp
                85                  90                  95

Ser Asp Gly Asn Val Ile Tyr Thr Phe Thr Asp Tyr Val Asn Thr Lys
            100                 105                 110

Asp Asp Val Lys Ala Thr Leu Thr Met Ser Ala Ala Ile Asp Pro Glu
        115                 120                 125

Asn Val Lys Lys Thr Gly Asn Val Thr Leu Ala Thr Gly Ile Gly Ser
    130                 135                 140

Thr Thr Ala Asn Lys Thr Val Leu Val Asp Tyr Glu Lys Tyr Gly Lys
145                 150                 155                 160

Phe Tyr Asn Leu Ser Ile Lys Gly Thr Ile Asp Gln Ile Asp Lys Thr
                165                 170                 175

Asn Asn Thr Tyr Arg Gln Thr Ile Tyr Val Asn Pro Ser Gly Asp Asn
            180                 185                 190

Val Ile Ala Pro Val Leu Thr Gly Asn Leu Lys Pro Asn Thr Asp Ser
        195                 200                 205

Asn Ala Leu Ile Asp Gln Gln Asn Thr Ser Ile Lys Val Tyr Lys Val
    210                 215                 220

Asp Asn Ala Ala Asp Leu Ser Glu Ser Tyr Phe Val Asn Pro Glu Asn
225                 230                 235                 240

Phe Glu Asp Val Thr Asn Ser Val Asn Ile Thr Phe Pro Asn Pro Asn
                245                 250                 255

Gln Tyr Lys Val Glu Phe Asn Thr Pro Asp Asp Gln Ile Thr Thr Pro
            260                 265                 270

Tyr Ile Val Val Val Asn Gly His Ile Asp Pro Asn Ser Lys Gly Asp
        275                 280                 285

Leu Ala Leu Arg Ser Thr Leu Tyr Gly Tyr Asn Ser Asn Ile Ile Trp
    290                 295                 300

Arg Ser Met Ser Trp Asp Asn Glu Val Ala Phe Asn Asn Gly Ser Gly
305                 310                 315                 320

Ser Gly Asp Gly Ile Asp Lys Pro Val Val Pro Glu Gln Pro Asp Glu
```

Pro Gly Glu Ile Glu Pro Ile Pro Glu Asp
                325                 330                 335

Pro Gly Glu Ile Glu Pro Ile Pro Glu Asp
            340                 345

<210> SEQ ID NO 29
<211> LENGTH: 346
<212> TYPE: PRT
<213> ORGANISM: Artificial Sequence
<220> FEATURE:
<223> OTHER INFORMATION: ClfAN2N3P116S/Y118A mutant 27

<400> SEQUENCE: 29

Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Gly Ser Gly Ser Gly Asp Gly Ile Asp
305                 310                 315                 320

Lys Pro Val Val Pro Glu Lys Asp Gln Asn Ala Thr Lys Pro Asp Glu
                325                 330                 335

Pro Gly Glu Ile Glu Pro Ile Pro Glu Asp

<210> SEQ ID NO 30
<211> LENGTH: 346
<212> TYPE: PRT
<213> ORGANISM: Artificial Sequence
<220> FEATURE:
<223> OTHER INFORMATION: ClfAN2N3P116S/Y118A mutant 28

<400> SEQUENCE: 30

```
Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Lys Asp Gln Asn Ala Thr Lys Glu
                325                 330                 335

Pro Gly Glu Ile Glu Pro Ile Pro Glu Asp
            340                 345
```

<210> SEQ ID NO 31
<211> LENGTH: 346
<212> TYPE: PRT
<213> ORGANISM: Artificial Sequence
<220> FEATURE:
<223> OTHER INFORMATION: ClfAN2N3P116S/Y118A mutant 29

<400> SEQUENCE: 31

```
Val Ala Ala Asp Ala Pro Ala Ala Gly Thr Asp Ile Thr Asn Gln Leu
1               5                   10                  15

Thr Asn Val Thr Val Gly Ile Asp Ser Gly Thr Thr Val Tyr Pro His
            20                  25                  30

Gln Ala Gly Tyr Val Lys Leu Asn Tyr Gly Phe Ser Val Pro Asn Ser
        35                  40                  45

Ala Val Lys Gly Asp Thr Phe Lys Ile Thr Val Pro Lys Glu Leu Asn
    50                  55                  60

Leu Asn Gly Val Thr Ser Thr Ala Lys Val Pro Pro Ile Met Ala Gly
65                  70                  75                  80

Asp Gln Val Leu Ala Asn Gly Val Ile Asp Ser Asp Gly Asn Val Ile
                85                  90                  95

Tyr Thr Phe Thr Asp Tyr Val Asn Thr Lys Asp Asp Val Lys Ala Thr
            100                 105                 110

Leu Thr Met Ser Ala Ala Ile Asp Pro Glu Asn Val Lys Lys Thr Gly
        115                 120                 125

Asn Val Thr Leu Ala Thr Gly Ile Gly Ser Thr Thr Ala Asn Lys Thr
    130                 135                 140

Val Leu Val Asp Tyr Glu Lys Tyr Gly Lys Phe Tyr Asn Leu Ser Ile
145                 150                 155                 160

Lys Gly Thr Ile Asp Gln Ile Asp Lys Thr Asn Asn Thr Tyr Arg Gln
                165                 170                 175

Thr Ile Tyr Val Asn Pro Ser Gly Asp Asn Val Ile Ala Pro Val Leu
            180                 185                 190

Thr Gly Asn Leu Lys Pro Asn Thr Asp Ser Asn Ala Leu Ile Asp Gln
        195                 200                 205

Gln Asn Thr Ser Ile Lys Val Tyr Lys Val Asp Asn Ala Ala Asp Leu
    210                 215                 220

Ser Glu Ser Tyr Phe Val Asn Pro Glu Asn Phe Glu Asp Val Thr Asn
225                 230                 235                 240

Ser Val Asn Ile Thr Phe Pro Asn Pro Asn Gln Tyr Lys Val Glu Phe
                245                 250                 255

Asn Thr Pro Asp Asp Gln Ile Thr Thr Pro Tyr Ile Val Val Val Asn
            260                 265                 270

Gly His Ile Asp Pro Asn Ser Lys Gly Asp Leu Ala Leu Arg Ser Thr
        275                 280                 285

Leu Tyr Gly Tyr Asn Ser Asn Ile Ile Trp Arg Ser Met Ser Trp Asp
    290                 295                 300

Asn Glu Val Ala Phe Asn Asn Gly Ser Gly Ser Gly Asp Gly Ile Asp
305                 310                 315                 320

Lys Pro Val Val Pro Glu Gln Pro Asp Glu Lys Asp Gln Asn Ala Thr
                325                 330                 335

Lys Gly Glu Ile Glu Pro Ile Pro Glu Asp
            340                 345
```

<210> SEQ ID NO 32
<211> LENGTH: 349
<212> TYPE: PRT

```
<213> ORGANISM: Artificial Sequence
<220> FEATURE:
<223> OTHER INFORMATION: ClfAN2N3P116S/Y118A with mutant 30 glycosite,
      N-terminal S, C-terminal GS

<400> SEQUENCE: 32

Ser Val Ala Ala Asp Ala Pro Ala Ala Gly Thr Asp Ile Thr Asn Gln
1               5                   10                  15

Leu Thr Asn Val Thr Val Gly Ile Asp Ser Gly Thr Thr Val Tyr Pro
            20                  25                  30

His Gln Ala Gly Tyr Val Lys Leu Asn Tyr Gly Phe Ser Val Pro Asn
        35                  40                  45

Ser Ala Val Lys Gly Asp Thr Phe Lys Ile Thr Val Pro Lys Glu Leu
    50                  55                  60

Asn Leu Asn Gly Val Thr Ser Thr Ala Lys Val Pro Pro Ile Met Ala
65                  70                  75                  80

Gly Asp Gln Val Leu Ala Asn Gly Val Ile Asp Ser Asp Gly Asn Val
                85                  90                  95

Ile Tyr Thr Phe Thr Asp Tyr Val Asn Thr Lys Asp Asp Val Lys Ala
            100                 105                 110

Thr Leu Thr Met Ser Ala Ala Ile Asp Pro Glu Asn Val Lys Lys Thr
        115                 120                 125

Gly Asn Val Thr Leu Ala Thr Gly Ile Gly Ser Thr Thr Ala Asn Lys
    130                 135                 140

Thr Val Leu Val Asp Tyr Glu Lys Tyr Gly Lys Phe Tyr Asn Leu Ser
145                 150                 155                 160

Ile Lys Gly Thr Ile Asp Gln Ile Asp Lys Thr Asn Asn Thr Tyr Arg
                165                 170                 175

Gln Thr Ile Tyr Val Asn Pro Ser Gly Asp Asn Val Ile Ala Pro Val
            180                 185                 190

Leu Thr Gly Asn Leu Lys Pro Asn Thr Asp Ser Asn Ala Leu Ile Asp
        195                 200                 205

Gln Gln Asn Thr Ser Ile Lys Val Tyr Lys Val Asp Asn Ala Ala Asp
    210                 215                 220

Leu Ser Glu Ser Tyr Phe Val Asn Pro Glu Asn Phe Glu Asp Val Thr
225                 230                 235                 240

Asn Ser Val Asn Ile Thr Phe Pro Asn Pro Asn Gln Tyr Lys Val Glu
                245                 250                 255

Phe Asn Thr Pro Asp Asp Gln Ile Thr Thr Pro Tyr Ile Val Val Val
            260                 265                 270

Asn Gly His Ile Asp Pro Asn Ser Lys Gly Asp Leu Ala Leu Arg Ser
        275                 280                 285

Thr Leu Tyr Gly Tyr Asn Ser Asn Ile Ile Trp Arg Ser Met Ser Trp
    290                 295                 300

Asp Asn Glu Val Ala Phe Asn Asn Gly Ser Gly Ser Gly Asp Gly Ile
305                 310                 315                 320

Asp Lys Pro Val Val Pro Glu Gln Pro Asp Glu Pro Gly Glu Ile Glu
                325                 330                 335

Pro Lys Asp Gln Asn Ala Thr Lys Pro Glu Asp Gly Ser
            340                 345

<210> SEQ ID NO 33
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Leu Pro Asp Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Ser or Thr

<400> SEQUENCE: 34

Xaa Xaa Asn Xaa Xaa
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Gln Asn Ala Thr
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 36

His His His His His His
1               5
```

```
<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      His-Arg tag

<400> SEQUENCE: 37

His Arg His Arg
1
```

IMMUNOGENIC COMPOSITION

SEQUENCE LISTING

The instant application contains a Sequence Listing which has been submitted electronically in ASCII format and is hereby incorporated by reference in its entirety. Said ASCII copy, created on Jul. 26, 2023 is named VB66308 US Corrected SL 27 Jul. 2023.txt and is 72 KB in size.

TECHNICAL FIELD

The present invention relates to the field of immunogenic compositions and vaccines, their manufacture and the use of such compositions in medicine. More particularly, it relates to a polypeptide from *Staphylococcus aureus* and its use as a vaccine antigen, in particular as a carrier protein conjugated to saccharide antigens.

BACKGROUND

*Staphylococcus aureus* is a major cause of invasive human infections, including bacteremia, endocarditis, pneumonia, and wound infections. *S. aureus* develops antibiotic resistance very rapidly, and strains have emerged which are resistant to commonly used antibiotics such as methicillin and even the antibiotic of last resort, vancomycin. Methicillin-resistant *S. aureus* (MRSA) is endemic in hospitals, and community-associated MRSA strains are spreading worldwide, posing a major global challenge.

There is thus an urgent need for a vaccine to prevent staphylococcal disease. Several vaccines have been tested in clinical trials, including capsular polysaccharide (CPS) conjugates, individual protein antigens, and monoclonal antibodies (mAbs) to lipoteichoic acid. However, all have failed at various developmental stages, and to date there is no vaccine against *S. aureus* on the market.

*S. aureus* vaccines that elicit both humoral and cell mediated immune responses are currently under evaluation, and both protein antigens including adhesins such as clumping factor A (ClfA) and CPS are key antigens under consideration for inclusion in a multicomponent vaccine.

Adherence of bacteria to host extracellular matrix components is a critical initial phase in bacterial infection. ClfA is an important *S. aureus* adhesin which is required for virulence and helps the bacteria evade host defence mechanisms. It binds to fibrinogen in the ECM, aiding in adherence and colonisation of host tissues and additionally causing cell clumping and coating of the bacterial cells in fibrinogen, which promotes immune evasion by impairing deposition of opsonins on the bacteria. ClfA is thus a promising antigen for inclusion in a *S. aureus* multicomponent vaccine.

90% of *S. aureus* strains express either Type 5 or Type 8 capsular polysaccharide, so a vaccine comprising CP5 and CP8 could potentially protect against the majority of circulating *S. aureus* strains. Vaccines comprising *S. aureus* capsular polysaccharides have been used to generate a protective immune response against staphylococci, but vaccines comprising CPS alone have not proved fully effective. A vaccine containing conjugates of *S. aureus* Type 5 and Type 8 capsular polysaccharides conjugated to *Pseudomonas* exoprotein A (StaphVAX—Nabi Biopharmaceuticals) has been tested in clinical trials, where it demonstrated safety and efficacy in PhI and II but failed to achieve the required endpoint in PhIII, as described in WO 03/61558.

A multicomponent vaccine comprising *S. aureus* CPS and the ClfA (Anderson et al 2012, Hum Vaccine Immunother 8: 1585-1594) has been tested in PhI human trials. The vaccine induced opsonic anti-CP antibodies and inhibitory anti-ClfA antibodies in PhI, and is currently being tested in PhIIb efficacy trials for prophylactic use in elective spinal fusion surgery patients.

Bioconjugates of *S. aureus* CP8 with *P. aeruginosa* EPA or *S. aureus* ClfA as carrier protein have been described in WO2015/082571. CP8-EPA bioconjugates were able to induce opsonic antibodies in rabbits, and vaccination of mice with CP8-EPA bioconjugates protected against bacteraemia induced by serotype 8 *S. aureus* strains. CP8-ClfA bioconjugates thus have potential for use in a vaccine against *S. aureus*.

SUMMARY OF THE INVENTION

The present invention provides a staphylococcal ClfA protein modified in order to introduce a glycosylation site for PglB, and bioconjugates thereof.

Accordingly, there is provided in one aspect of the present invention, a polypeptide comprising or consisting of an amino acid sequence of SEQ ID NO. 3 or an amino acid sequence at least 80%, 85%, 90%, 92%, 95%, 96%, 97%, 98% or 99% identical to SEQ ID NO. 3, for example SEQ ID NO: 4, modified in that the amino acid sequence comprises one or more consensus sequence(s) selected from D/E-X-N-Z-S/T (SEQ ID NO. 21) and K-D/E-X-N-Z-S/T-K (SEQ ID NO. 22), wherein X and Z are independently any amino acid apart from proline. In a preferred embodiment, said consensus sequence has been added at, or substituted for, one or more amino acids between amino acid residues 313-340 of SEQ ID NO: 3 or at an equivalent position within an amino acid sequence at least 80%, 85%, 90%, 92%, 95%, 96%, 97%, 98% or 99% identical to SEQ ID NO. 3.

In an embodiment, said consensus sequence is substituted for amino acid residue Q327, D329, P331 and/or I337 in SEQ ID NO. 3, or substituted in an amino acid sequence at least 80%, 85%, 90%, 92%, 95%, 96%, 97%, 98% or 99% identical to SEQ ID NO. 3 at an amino acid position equivalent to amino acid residue Q327, D329, P331, and/or I337 in SEQ ID NO. 3.

In an embodiment, said consensus sequence is substituted for amino acid residue Q327, D329 or I337 in SEQ ID NO. 3, or substituted in an amino acid sequence at least 80%, 85%, 90%, 92%, 95%, 96%, 97%, 98% or 99% identical to SEQ ID NO. 3 at an amino acid position equivalent to amino acid residue Q327, D329, or I337 in SEQ ID NO. 3.

In a preferred embodiment, said consensus sequence is substituted for amino acid residue I337 in SEQ ID NO. 3, or substituted in an amino acid sequence at least 80%, 85%, 90%, 92%, 95%, 96%, 97%, 98% or 99% identical to SEQ ID NO. 3.

In an embodiment, said consensus sequence has a sequence K-D/E-X-N-Z-S/T-K (SEQ ID NO. 22) wherein X is Q (glutamine) and Z is A (alanine) (e.g. K-D-Q-N-A-T-K (SEQ ID NO. 23)).

The polypeptide may further comprise at least one amino acid substitution selected from P116 to S and Y118 to A with reference to the amino acid sequence of SEQ ID NO. 3 (corresponding to positions P336 and Y338 in the sequence of SEQ ID NO: 1) or an equivalent position in an amino acid sequence at least 80%, 85%, 90%, 92%, 95%, 96%, 97%, 98% or 99% identical to SEQ ID NO. 3), for example SEQ ID NOs 4-5 or 10-12.

The polypeptide may comprise an additional serine residue at the N-terminus, for example SEQ ID NO. 6 or SEQ ID NO. 12, and/or additional residues such as Gly or Gly-Ser at the C-terminus, for example SEQ ID NO: 32.

The polypeptide may comprise a signal sequence which is capable of directing the protein to the periplasm of a host cell (e.g. bacterium), optionally said signal sequence being selected from SEQ ID NO. 13-20, preferably SEQ ID NO: 13, optionally said protein having an amino acid sequence at least 97%, 98%, 99% or 100% identical to SEQ ID NO. 5 or SEQ ID NO. 11.

The polypeptide may comprise a peptide tag which is useful for the purification of the ClfA protein, optionally said peptide tag comprising six histidine residues and optionally said peptide tag being located at the C-terminus of the amino acid sequence, optionally said peptide tag being preceded by a linker such as Gly or Gly-Ser, optionally said protein having an amino acid sequence at least 97%, 98%, 99% or 100% identical to SEQ ID NO: 25, SEQ ID NO: 26, or SEQ ID NO: 27.

According to a further aspect of the invention, there is provided a conjugate (e.g. bioconjugate) comprising an antigen, preferably a polysaccharide antigen, linked to a polypeptide of the invention.

According to a further aspect of the invention, there is provided a polynucleotide encoding a polypeptide of the invention.

According to a further aspect of the invention, there is provided a vector comprising a polynucleotide encoding a polypeptide of the invention.

According to a further aspect of the invention, there is provided a host cell comprising:
i) one or more nucleic acids that encode glycosyltransferase(s);
ii) a nucleic acid that encodes an oligosaccharyl transferase;
iii) a nucleic acid that encodes a polypeptide of the invention; and optionally
iv) a nucleic acid that encodes a polymerase (e.g. wzy).

According to a further aspect of the invention, there is provided a process for producing a bioconjugate that comprises (or consists of) a polypeptide linked to a saccharide, said method comprising: (i) culturing the host cell of the invention under conditions suitable for the production of proteins and (ii) isolating the bioconjugate produced by said host cell.

According to a further aspect of the invention, there is provided a bioconjugate produced by a process of the invention, wherein said bioconjugate comprises a saccharide linked to a polypeptide.

According to a further aspect of the invention, there is provided an immunogenic composition comprising the polypeptide of the invention, or a conjugate of the invention, or a bioconjugate of the invention and a pharmaceutically acceptable excipient or carrier.

According to a further aspect of the invention, there is provided a method of making a immunogenic composition of the invention comprising the step of mixing the polypeptide or the conjugate or the bioconjugate with a pharmaceutically acceptable excipient or carrier.

According to a further aspect of the invention, there is provided a method for the treatment or prevention of *Staphylococcus aureus* infection in a subject in need thereof comprising administering to said subject a therapeutically effective amount of a polypeptide of the invention, or a conjugate of the invention, or a bioconjugate of the invention.

According to a further aspect of the invention, there is provided a method of immunising a human host against *Staphylococcus aureus* infection comprising administering to the host an immunoprotective dose of a polypeptide of the invention, or a conjugate of the invention, or a bioconjugate of the invention.

According to a further aspect of the invention, there is provided a method of inducing an immune response to *Staphylococcus aureus* in a subject, the method comprising administering a therapeutically or prophylactically effective amount of a polypeptide of the invention, or a conjugate of the invention, or a bioconjugate of the invention.

According to a further aspect of the invention, there is provided a polypeptide of the invention, or a conjugate of the invention, or a bioconjugate of the invention for use in the treatment or prevention of a disease caused by *Staphylococcus aureus* infection.

According to a further aspect of the invention, there is provided a polypeptide of the invention, or a conjugate of the invention, or a bioconjugate of the invention in the manufacture of a medicament for the treatment or prevention of a disease caused by *Staphylococcus aureus* infection.

DESCRIPTION OF FIGURES

FIG. 1 is a schematic representation of the domain organization of *S. aureus* clumping factor ClfA. It highlights the fibrinogen binding subdomains N1-N2-N3 and shows the position and nature of the detoxification mutations located in subdomain N2. Numbers refer to amino acid positions (start of each domain). SS=signal sequence; N1-N3: Fibrinogen-binding subdomains; R=serine-aspartate dipeptide repeat region; W=cell wall-spanning region; M=membrane-spanning region.

FIG. 2 represents the crystal structure of *S. aureus* clumping factor domains N2N3 (ClfAN2N3, Deivanayagam et al., EMBO J., 2002, PDB identifier 1N67), showing the extreme N-terminal and C-terminal glycosylation sites tested A: one at the very N-terminal end (D244KDQNATK (SEQ ID NO: 23)=mutant 1) and B: one at the very C-terminal end (I557KDQNATK (SEQ ID NO: 23)=mutant 30).

3a:

| Lane | 1 | 2 | 3 | 4 | 5 | 6 | 7 | 8 | 9 | 10 |
|---|---|---|---|---|---|---|---|---|---|---|
| plasmid | M | 1141 | 1142 | 1143 | 1144 | 974 | 633 | 633 SOC | 150 | EPA-cp8 EF5 |
| Mutant # |  | 1 | 2 | 3 | 4 |  |  |  |  | 003_068 |

3b:

| Lane | 1 | 2 | 3 | 4 | 5 | 6 | 7 | 8 | 9 | 10 |
|---|---|---|---|---|---|---|---|---|---|---|
| plasmid | M | 1145 | 1146 | 1147 | 1148 | 1149 | 1150 | 1151 | 1152 | EPA-cp8 |
| Mutant # | | 5 | 6 | 7 | 8 | 9 | 10 | 11 | 12 | EF5 003_068 |

4a:

| Lane | 1 | 2 | 3 | 4 | 5 | 6 | 7 | 8 | 9 | 10 |
|---|---|---|---|---|---|---|---|---|---|---|
| plasmid | M | 1153 | 1154 | 1155 | 1156 | 1158 | 1159 | 1160 | 1161 | EPA-cp8 |
| Mutant # | | 13 | 14 | 15 | 16 | 18 | 19 | 20 | 21 | EF5 003_068 |

4b:

| Lane | 1 | 2 | 3 | 4 | 5 | 6 | 7 | 8 | 9 | 10 |
|---|---|---|---|---|---|---|---|---|---|---|
| plasmid | M | 1162 | 1163 | 1164 | 1166 | 1167 | 1168 | 1169 | 1170 | EPA-cp8 |
| Mutant # | | 22 | 23 | 24 | 26 | 27 | 28 | 29 | 30 | EF5 003_068 |

Figure 5B:
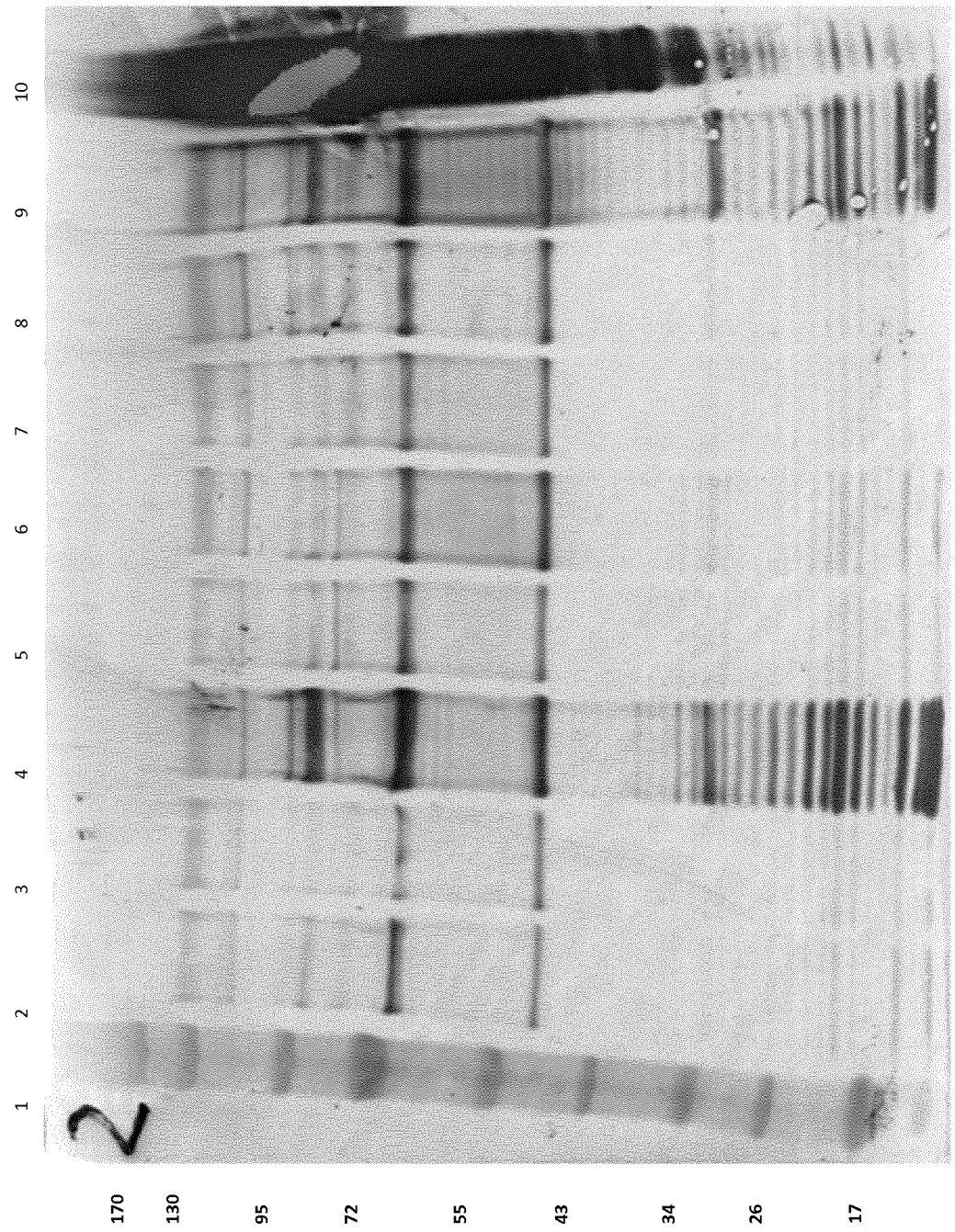
Figure 6A:
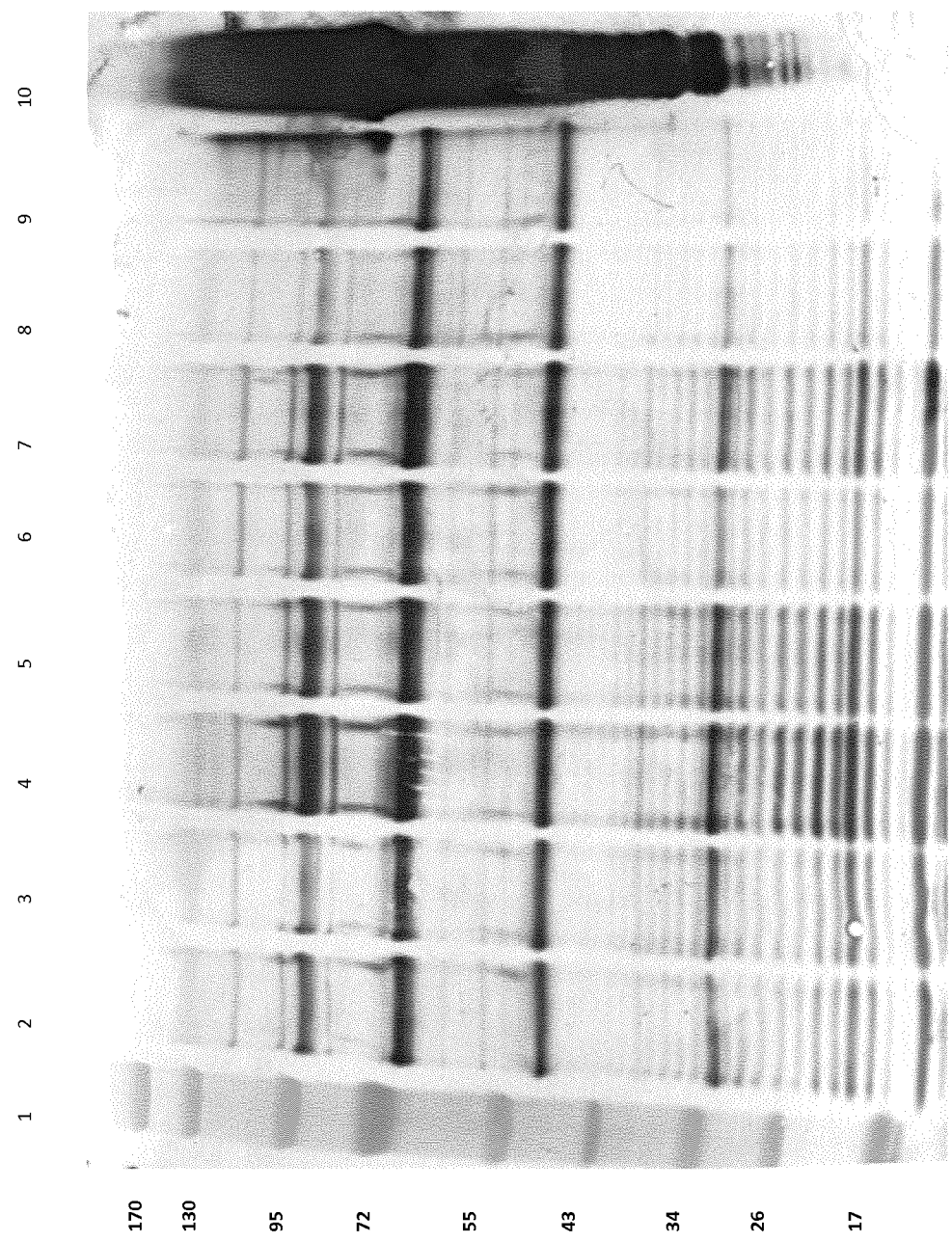

FIGS. 5, 6: Anti-CP8 Western blot of different ClfA glycosite mutant bioconjugates Anti-CP8 Western blot analysis of CP8-ClfAN2N3 bioconjugate production for mutants 1-30 described in Example 1, with D328KDQNRTK (SEQ ID NO: 24) (plasmid 633) as positive control and EPA-CP8 Blot: rabbit α-CP8-EPA-His 1:1000, goat α-rabbit 1:10 000.

5a:

| Lane | 1 | 2 | 3 | 4 | 5 | 6 | 7 | 8 | 9 | 10 |
|---|---|---|---|---|---|---|---|---|---|---|
| plasmid | M | 1141 | 1142 | 1143 | 1144 | 974 | 633 | 633 SOC | 150 | EPA-cp8 |
| Mutant # | | 1 | 2 | 3 | 4 | | | | | EF5 003_068 |

5b:

| Lane | 1 | 2 | 3 | 4 | 5 | 6 | 7 | 8 | 9 | 10 |
|---|---|---|---|---|---|---|---|---|---|---|
| plasmid | M | 1145 | 1146 | 1147 | 1148 | 1149 | 1150 | 1151 | 1152 | EPA-cp8 |
| Mutant # | | 5 | 6 | 7 | 8 | 9 | 10 | 11 | 12 | EF5 003_068 |

6a:

| Lane | 1 | 2 | 3 | 4 | 5 | 6 | 7 | 8 | 9 | 10 |
|---|---|---|---|---|---|---|---|---|---|---|
| plasmid | M | 1153 | 1154 | 1155 | 1156 | 1158 | 1159 | 1160 | 1161 | EPA-cp8 |
| Mutant # | | 13 | 14 | 15 | 16 | 18 | 19 | 20 | 21 | EF5 003_068 |

6b:

| Lane | 1 | 2 | 3 | 4 | 5 | 6 | 7 | 8 | 9 | 10 |
|---|---|---|---|---|---|---|---|---|---|---|
| plasmid | M | 1162 | 1163 | 1164 | 1166 | 1167 | 1168 | 1169 | 1170 | EPA-cp8 |
| Mutant # | | 22 | 23 | 24 | 26 | 27 | 28 | 29 | 30 | EF5 003_068 |

Figure 7:
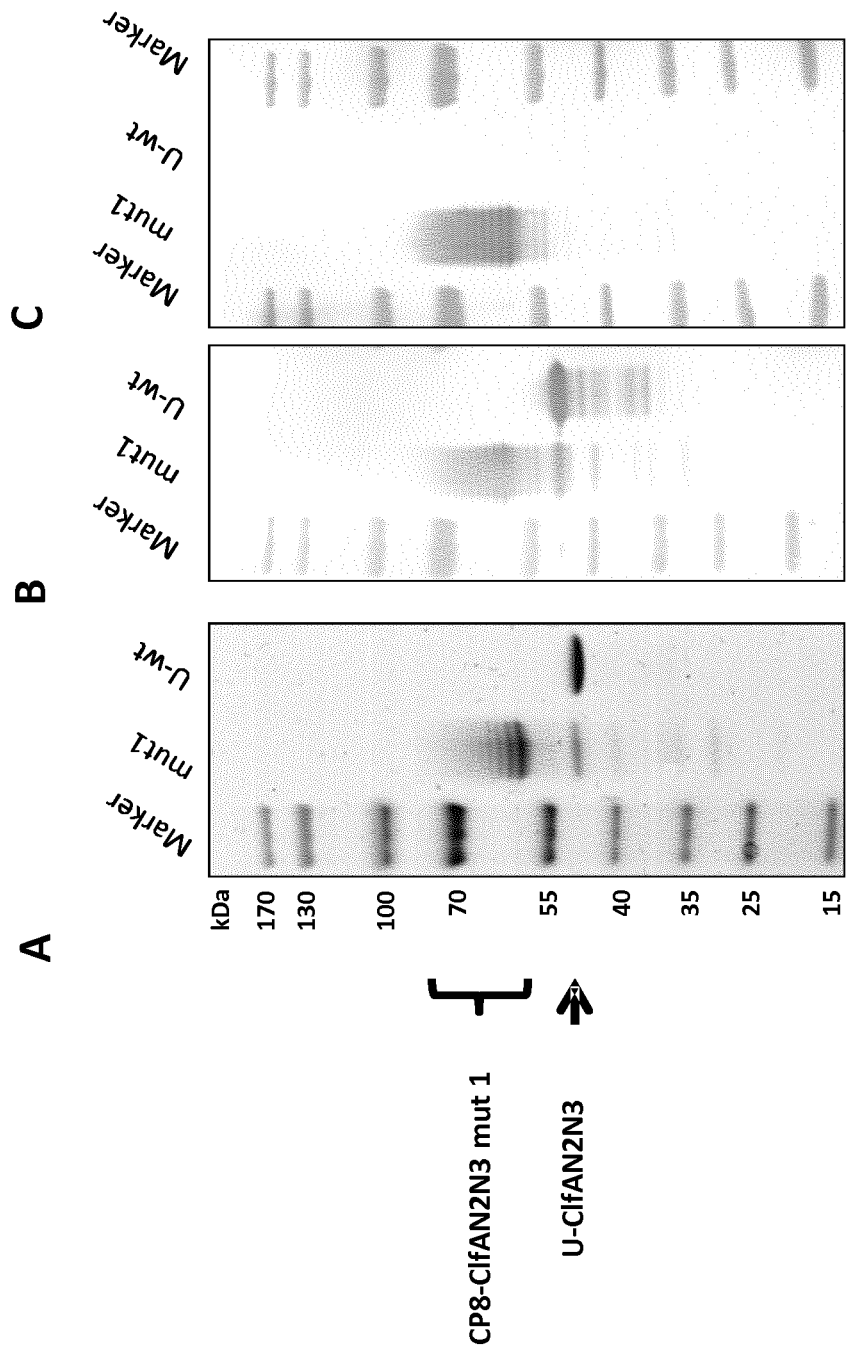

FIG. 7: Expression and purification of CP8-ClfAN2N3 mutant 1 (D244KDQNATK (SEQ ID NO: 23)) bioconjugate FIG. 7 shows a SDS-PAGE SIMPLYBLUE™ SafeStain, an anti-ClfA and an anti-CP8 Western Blot analysis of the final product of CP8-ClfAN2N3 mutant 1, expressed from a three plasmid system in a 20 L bioreactor and purified to homogeneity. A) SIMPLYBLUE™ Safe Stain B) anti-ClfAN2N3 Western Blot Analysis C) anti-CP8 Western Blot of CP8-ClfAN2N3 mut1 (mut1) and unglycosylated ClfAN2N3 wt (U-wt) purified to homogeneity.

Figure 8:
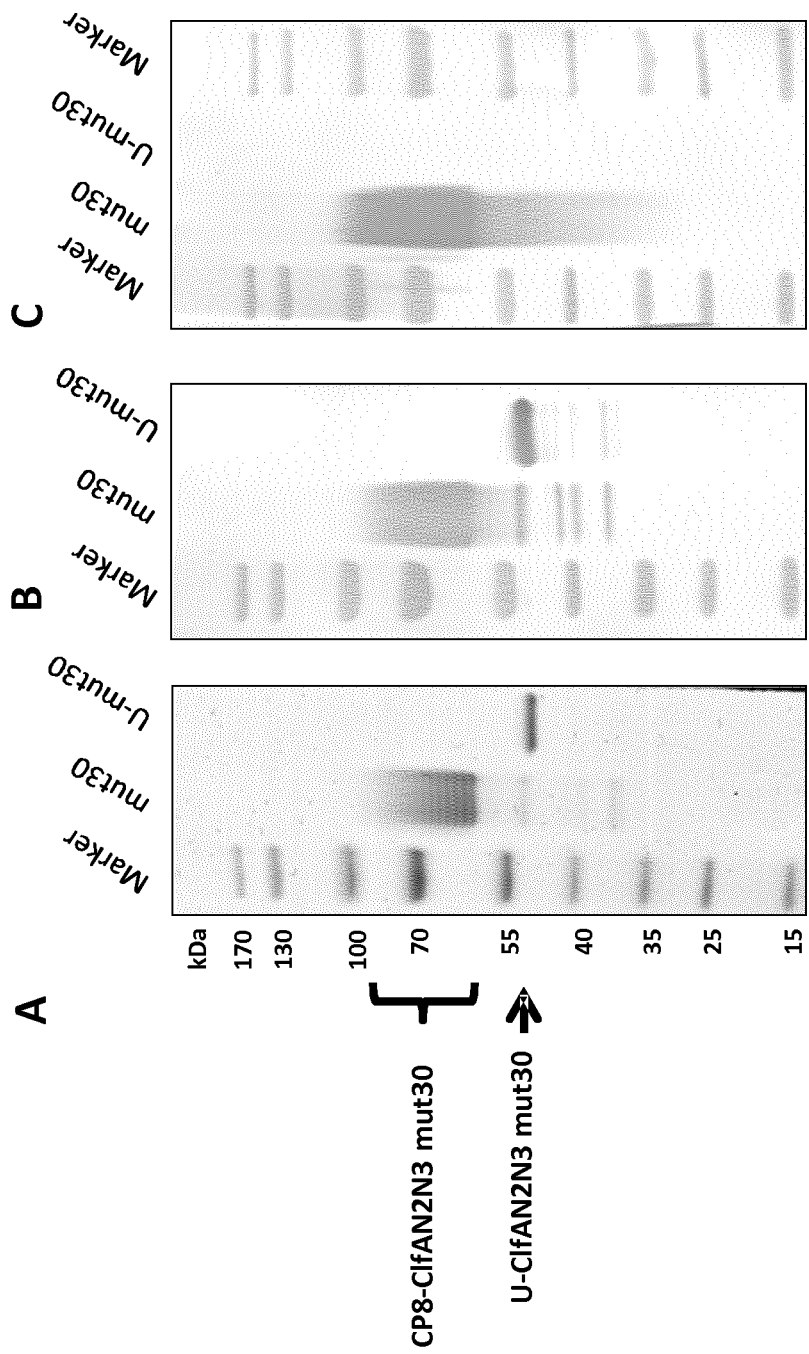

FIG. 8: Expression and purification of CP8-ClfAN2N3 mutant 30 (I557KDQNATK (SEQ ID NO: 23)) bioconjugate FIG. 8 shows a SDS-PAGE SIMPLYBLUE™ SafeStain, an anti-ClfA and an anti-CP8 Western Blot analysis of the final product of CP8-ClfAN2N3 mutant 30, expressed from a one plasmid system in a 20 L bioreactor and purified to homogeneity. A) SIMPLYBLUE™ Safe Stain and B) anti-ClfAN2N3 Western Blot Analysis and C) anti-CP8 Western Blot of CP8-ClfAN2N3 mut30 (mut30) and unglycosylated ClfAN2N3 mut 30 (U-mut 30) purified to homogeneity.

Figure 9:
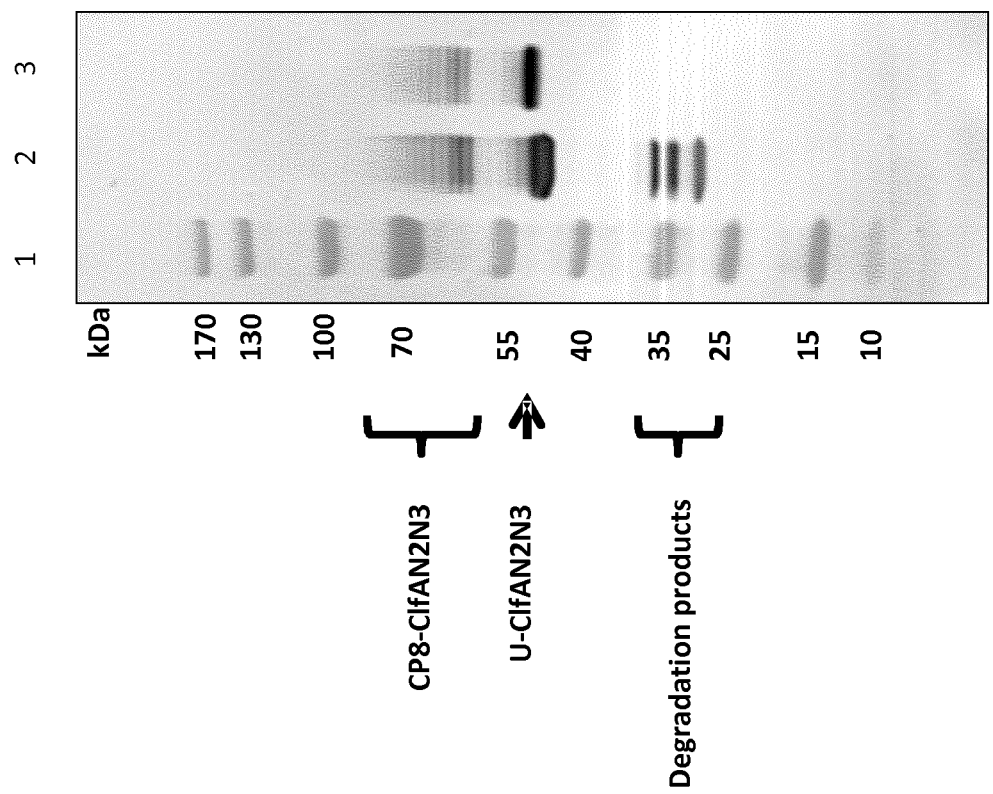

FIG. 9: Improved protein stability of S. aureus bioconjugate production in the context of carrier protein ClfAN2N3 glyco-site mutant 30 compared to glycosite mutant 1

Western blot analysis of CP8-ClfAN2N3 bioconjugate production using the three plasmid system demonstrating reduced protein degradation for glycosite mutant 30 (Lane 3) relative to glycosite mutant 1 (Lane 2). Lane 1=protein marker.

Figure 10:
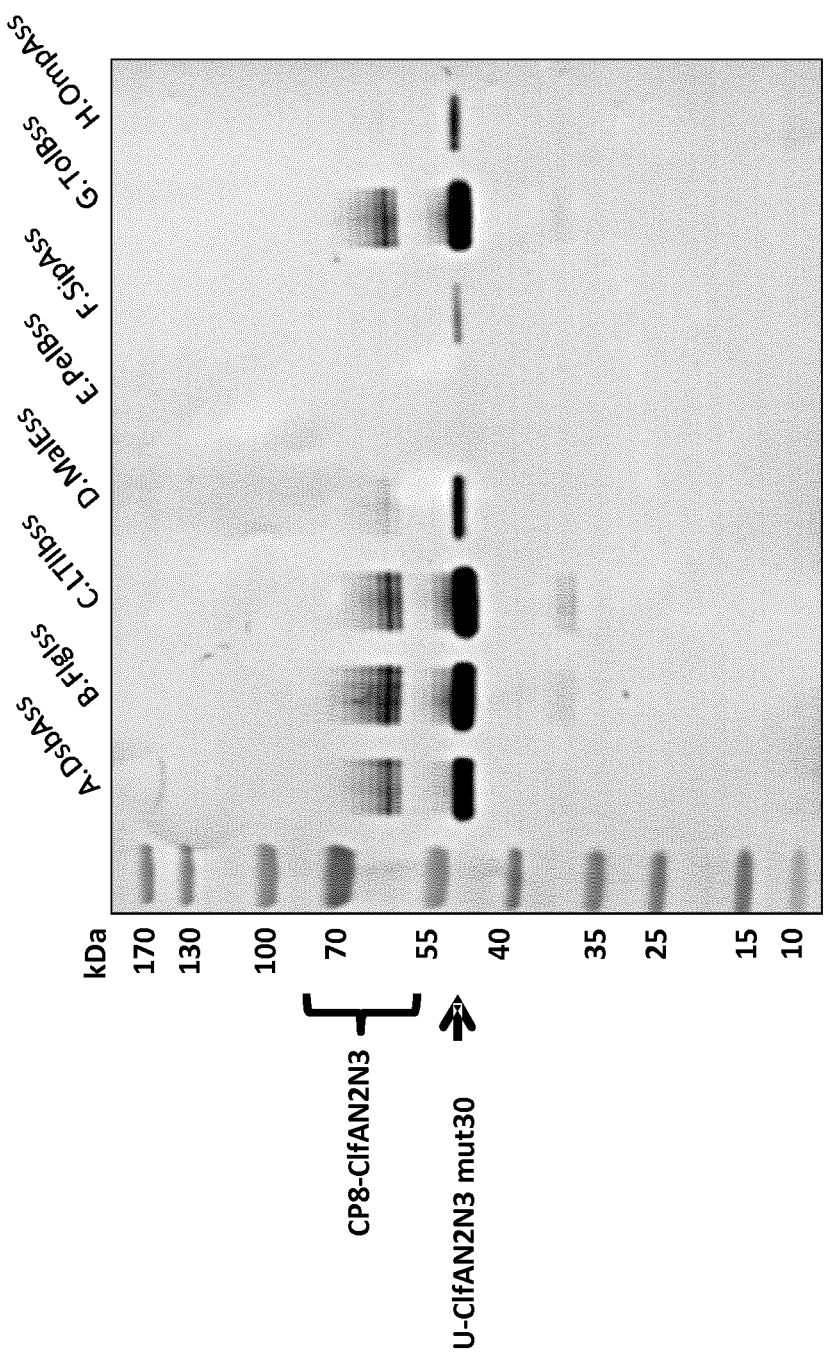

FIG. 10: Impact on production yields with different signal sequences on ClfAN2N3 mutant 30

Ant-His Western blot of ClfA-CP8-ClfAN2N3 mutant 30 with HRHR (SEQ ID NO: 37) tag produced using different signal sequences: E. coli disulfide oxidoreductase DsbA signal sequence (DsbA), a S. flexneri flagellar P-ring protein signal sequence (FlgI), E. coli heat-labile enterotoxin IIB, B chain signal sequence (LTIIb), E. coli maltose binding protein MalE signal sequence (MalE), P. carotovorum pectase lyase 2 precursor signal sequence (PelB), S. agalactiae surface immunogenic protein signal sequence (SipA), E. coli translocation protein signal sequence (TolB), E. coli outer membrane protein signal sequence (OmpA).

Lane 1: PageRuler Prestained Protein Marker
Lane A: DsbA signal sequence
Lane B: FlgI signal sequence
Lane C: LTIIb signal sequence
Lane D: MalE signal sequence
Lane E: PelB signal sequence
Lane F: SipA signal sequence
Lane G: TolB signal sequence
Lane H: OmpA signal sequence

DETAILED DESCRIPTION

Terminology

Carrier protein: a protein covalently attached to an antigen (e.g. saccharide antigen) to create a conjugate (e.g. bioconjugate). A carrier protein activates T-cell mediated immunity in relation to the antigen to which it is conjugated.

Any amino acid apart from proline (pro, P): refers to an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), serine (ser, S), threonine (thr, T), tryptophan (trp, W), tyrosine (tyr, Y), and valine (val, V).

ClfA: Clumping factor A from Staphylococcus aureus
CP: Capsular polysaccharide
LPS: lipopolysaccharide.
wzy: the polysaccharide polymerase gene encoding an enzyme which catalyzes polysaccharide polymerization. The encoded enzyme transfers oligosaccharide units to the non-reducing end forming a glycosidic bond.
waaL: the O antigen ligase gene encoding a membrane bound enzyme. The encoded enzyme transfers undecaprenyl-diphosphate (UPP)-bound O antigen to the lipid A core oligosaccharide, forming lipopolysaccharide.
Und-PP: undecaprenyl pyrophosphate.
Und-P: undecaprenyl phosphate
Reducing end: the reducing end of an oligosaccharide or polysaccharide is the monosaccharide with a free anomeric carbon that is not involved in a glycosidic bond and is thus capable of converting to the open-chain form.

As used herein, the term "bioconjugate" refers to conjugate between a protein (e.g. a carrier protein) and an antigen (e.g. a saccharide) prepared in a host cell background, wherein host cell machinery links the antigen to the protein (e.g. N-links). Usually, in a bioconjugate the polysaccharide is linked to asparagine via N-acetylglucosamine.

As used herein, the term "effective amount," in the context of administering a therapy (e.g. an immunogenic composition or vaccine of the invention) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, the term "subject" refers to an animal, in particular a mammal such as a primate (e.g. human).

As used herein, the term "donor oligosaccharide or polysaccharide" refers to an oligosaccharide or polysaccharide from which a oligosaccharide or polysaccharide is derived. Donor oligosaccharides and polysaccharides, as used herein, comprise a hexose monosaccharide (e.g. glucose) at the reducing end of the first repeat unit. Use of the term donor oligosaccharide or polysaccharide is not meant to suggest that an oligosaccharide or polysaccharide is modified in situ. Rather, use of the term donor oligosaccharide or polysaccharide is meant to refer to an oligosaccharide or polysaccharide that, in its wild-type state, is a weak substrate for oligosaccharyl transferase (e.g. PglB) activity or is not a substrate for oligosaccharyl transferase (e.g. PglB) activity. Exemplary donor oligosaccharides or polysaccharides include those from bacteria, including Staphylococcus aureus CP5 and CP8. Those of skill in the art will readily be able determine whether an oligosaccharide or polysaccharide comprises a hexose monosaccharide (e.g. glucose) at the reducing end of the first repeat unit, and thus whether such an oligosaccharide or polysaccharide is a donor oligosaccharide or polysaccharide as encompassed herein.

As used herein, the term "hexose monosaccharide derivative" refers to a derivative of a hexose monosaccharide that can be a substrate for oligosaccharyl transferase activity. In general, hexose monosaccharide derivatives comprise a monosaccharide comprising an acetamido group at position 2. Exemplary hexose monosaccharide derivatives include GlcNAc, HexNAc, deoxy HexNAc, or 2,4-diacetamido-2,4,6-trideoxyhexose.

As used herein, the term "hybrid oligosaccharide or polysaccharide" refers to an engineered oligosaccharide or polysaccharide that does not comprise a hexose at the reducing end of the first repeat unit, but instead comprises a hexose monosaccharide derivative at the reducing end of the first repeat unit.

As used herein, reference to a percentage sequence identity between two amino or nucleic acid sequences means that, when aligned, that percentage of amino acids or bases are the same in comparing the two sequences. This alignment and the percent homology or sequence identity can be determined using software programs known in the art, for example those described in section 7.7.18 of Current Protocols in Molecular Biology (F. M. Ausubel et al., eds., 1987, Supplement 30). A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2: 482-489. Percentage identity to any particular sequence (e.g. to a particular SEQ ID) is ideally calculated over the entire length of that sequence. The percentage sequence identity between two sequences of different lengths is preferably calculated over the length of the longer sequence.

As used herein, the term "immunogenic fragment" is a portion of an antigen smaller than the whole, that is capable of eliciting a humoral and/or cellular immune response in a host animal, e.g. human, specific for that fragment. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Typically, fragments comprise at least 10, 20, 30, 40, or 50 contiguous amino acids of the full length sequence. However, fragments may also be 100 or more, 200 or more, 300 or more or 400 or more amino acids in length. Fragments may be readily modified by adding or removing 1, 2, 3, 4, 5, 6, 7, 8, 9, 10, 20, 30, 40 or 50 amino acids from either or both of the N and C termini.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "deletion" is the removal of one or more amino acid residues from the protein sequence. Typically, no more than about from 1 to 6 residues (e.g. 1 to 4 residues) are deleted at any one site within the protein molecule.

As used herein, the term "insertion" is the addition of one or more non-native amino acid residues in the protein sequence. Typically, no more than about from 1 to 7 residues (e.g. 1 to 4 residues) are inserted at any one site within the protein molecule.

Proteins

Clumping factor A (ClfA) is a fibrinogen γ-chain-binding S. aureus adhesion protein which is present in nearly all S. aureus strains. It is an important virulence factor, contributing to the pathogenesis of septic arthritis and endocarditis. ClfA binds to the C-terminus of the γ-chain of fibrinogen, and is thereby able to induce clumping of bacteria in fibrinogen solution. Expression of ClfA on S. aureus hampers phagocytosis by both macrophages and neutrophils. In neutrophils this is due to both a fibrinogen-dependent and to a fibrinogen-independent mechanism. In contrast, platelets are activated by bacteria expressing ClfA through its interaction with GPIIb/IIIa leading to aggregation. This is most efficiently executed when fibrinogen is present, but there is also a fibrinogen-independent pathway for platelet activation.

ClfA contains a 520 amino acid N-terminal A domain (the Fibrinogen Binding Region), which comprises three separately folded subdomains N1, N2 and N3. The A domain is followed by a serine-aspartate dipeptide repeat region and a cell wall- and membrane-spanning region, which contains the LPDTG-motif (SEQ ID NO: 33) for sortase-promoted anchoring to the cell wall.

In an embodiment, the polypeptide of the invention may be derived from an amino acid sequence at least 80%, 85%, 90%, 92%, 95%, 96%, 97%, 98% or 99% identical to SEQ ID NO. 1 which is an immunogenic fragment and/or a variant of SEQ ID NO. 1 (e.g. SEQ ID NO. 3).

Figure 1:
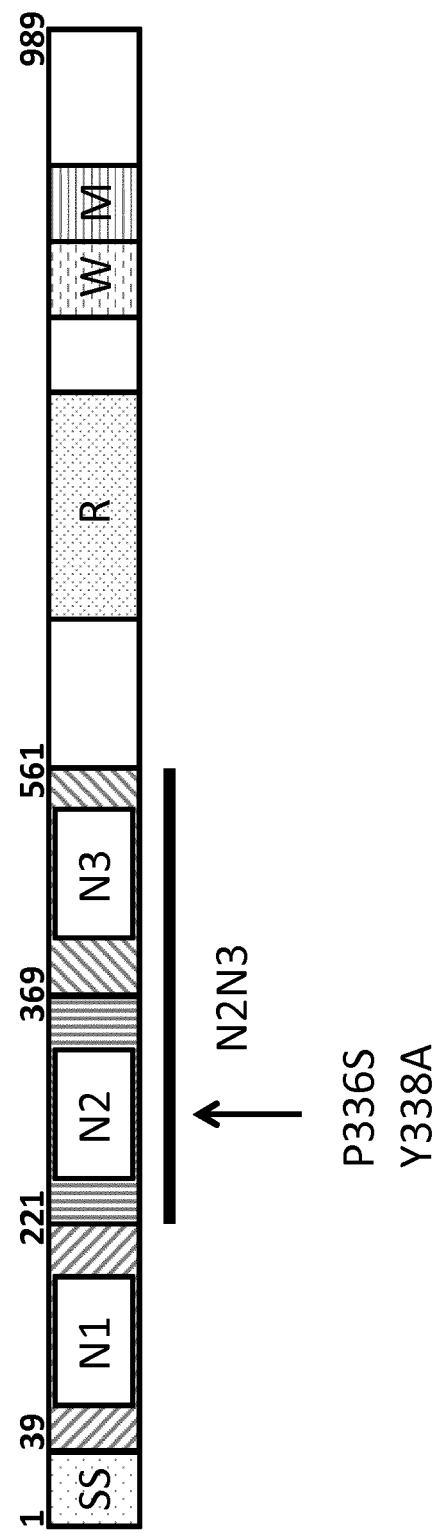
FIG. 1: Overview of protein domains in clumping factor from *Staphylococcus aureus*
Figure 2:
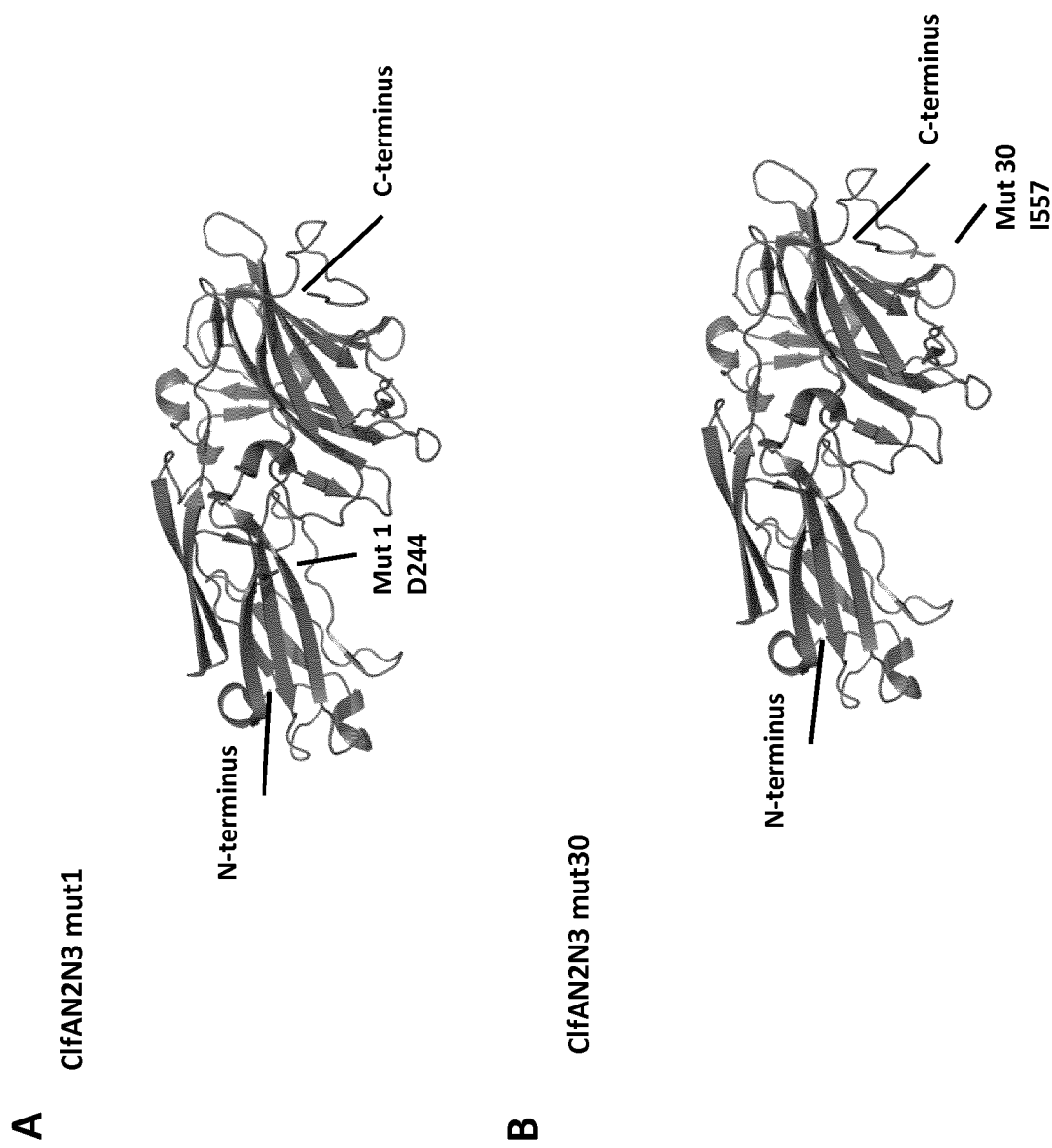
FIG. 2: Crystal structures of *S. aureus* clumping factor domains N2 and N3 (ClfAN2N3, PDB identifier 1N67) showing loci of the glycosylation sites introduced either at the very N-terminal end (mutant 1) or at the very C-terminal end (mutant 30).

In an embodiment, the polypeptide of the invention may be derived from an immunogenic fragment of SEQ ID NO. 1 comprising at least about 15, at least about 20, at least about 40, at least about 60, at least about 100, at least about 300, or at least about 400 contiguous amino acid residues of the full length sequence, wherein said polypeptide is capable of eliciting an immune response specific for said amino acid sequence. The fibrinogen binding domain of native ClfA is known to consist of three separately folded subdomains N1, N2 and N3, as shown in FIG. 1. These domains may be modified by removing and/or modifying one or more of these domains. In an embodiment, the fragment of SEQ ID NO. 1 contains exactly or at least 1, 2 or 3 domains. In another embodiment, the fragment of SEQ ID NO. 1 contains exactly or at least 2 or 3 domains. In another embodiment, the fragment of SEQ ID NO. 1 contains at least 2 domains, preferably domains N2 and N3. In an embodiment, the fragment of SEQ ID NO. 1 may comprise (or consist of) the amino acid residues of N1 (residues 39-220) of SEQ ID NO. 1. In an embodiment, the fragment of SEQ ID NO. 1 may comprise (or consist of) the amino acid residues of N2 (residues 221-368) of SEQ ID NO. 1. In an embodiment, the fragment of SEQ ID NO. 1 may comprise (or consist of) the amino acid residues of N3 (residues 369-560)2 of SEQ ID NO. 1. In an embodiment, the fragment of SEQ ID NO. 1 may comprise (or consist of) the amino acid residues of N1N2N3 (residues 39-560) of SEQ ID NO. 1 (SEQ ID NO: 2). In a preferred embodiment, the fragment of SEQ ID NO. 1 may comprise (or consist of) the amino acid residues of N2N3 (residues 221-560) of SEQ ID NO. 1 (SEQ ID NO: 3).

In some embodiments, the polypeptide of the invention may comprise (or consist of) subdomains N1, N2 and N3 of ClfA (SEQ ID NO: 2) or an amino acid sequence at least 80%, 85%, 90%, 91%, 92%, 93%, 94%, 95%, 96%, 97%, 98% or 99% identical to SEQ ID NO: 2. In other embodiments, the polypeptide of the invention may comprise (or consist of) subdomains N2 and N3 (SEQ ID NO: 3) or an amino acid sequence at least 80%, 85%, 90%, 91%, 92%, 93%, 94%, 95%, 96%, 97%, 98% or 99% identical to SEQ ID NO: 3.

The present invention thus provides a polypeptide comprising (or consisting of) an amino acid sequence of SEQ ID NO. 3 or an amino acid sequence at least 80%, 85%, 90%, 91%, 92%, 93%, 94%, 95%, 96%, 97%, 98% or 99% identical to SEQ ID NO. 3 (e.g. SEQ ID NO. 4), modified in that the amino acid sequence comprises one or more consensus sequence(s) selected from: D/E-X-N-Z-S/T (SEQ ID NO. 21) and K-D/E-X-N-Z-S/T-K (SEQ ID NO. 22), wherein X and Z are independently any amino acid apart from proline. These sequences may be modified by addition of an N-terminal serine for cloning purposes. The sequences may further be modified to contain detoxifying mutations, such as any one or all of the detoxifying mutations described herein.

In an embodiment, the polypeptide of the invention may be derived from an amino acid sequence at least 80%, 85%, 90%, 92%, 95%, 96%, 97%, 98% or 99% identical to SEQ ID NO. 1 which is a variant of SEQ ID NO. 1 which has been modified by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. In an embodiment, the modified ClfA protein of the present invention may be derived from a variant in which 1 to 10, 5 to 10, 1 to 5, 1 to 3, 1 to 2 or 1 amino acids are substituted, deleted, or added in any combination. For example, the polypeptide of the invention may be derived from an amino acid sequence which is a variant of SEQ ID NO. 3 in that it comprises an additional N-terminal serine (e.g. SEQ ID NO: 12).

In an embodiment, the present invention includes fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

The term "polypeptide" refers to a ClfA amino acid sequence (for example, having a ClfA amino acid sequence of SEQ ID NO. 3 or an amino acid sequence at least 80%, 85%, 90%, 91%, 92%, 93%, 94%, 95%, 96%, 97%, 98% or 99% identical to SEQ ID NO. 3), which ClfA amino acid sequence may be a wild-type ClfA amino acid sequence which has been modified by the addition, substitution or deletion of one or more amino acids (for example, by addition of a consensus sequence(s) selected from D/E-X-N-Z-S/T (SEQ ID NO. 21) and K-D/E-X-N-Z-S/T-K (SEQ ID NO. 22); or by substitution of one or more amino acids by a consensus sequence(s) selected from D/E-X-N-Z-S/T (SEQ ID NO. 22) and K-D/E-X-N-Z-S/T-K (SEQ ID NO. 23). The polypeptide may also comprise further modifications (additions, substitutions, deletions) as well as the addition or substitution of one or more consensus sequence (s). For example, the ClfA protein may contain detoxifying mutations to reduce or eliminate fibrinogen binding as described below, the signal sequence of a wild-type ClfA protein may be deleted or substituted with an alternative signal sequence, and/or a peptide tag may be added. In an embodiment, the polypeptide of the invention may be a non-naturally occurring ClfA protein. In an embodiment, the polypeptide of the invention comprises the sequence of SEQ ID NO: 10.

In an embodiment of the invention, one or more amino acids (e.g. 1-7 amino acids, e.g. one amino acid) of the ClfA amino acid sequence (for example, having an amino acid sequence of SEQ ID NO. 3 or a ClfA amino acid sequence at least 80%, 85%, 90%, 91%, 92%, 93%, 94%, 95%, 96%, 97%, 98% or 99% identical to SEQ ID NO. 3) have been substituted by a D/E-X-N-Z-S/T (SEQ ID NO. 21) or K-D/E-X-N-Z-S/T-K (SEQ ID NO. 22) (e.g. K-D-Q-N-A-T-K (SEQ ID NO. 23)) consensus sequence. For example, a single amino acid in the ClfA amino acid sequence (e.g. SEQ ID NO. 3) may be replaced with a D/E-X-N-Z-S/T (SEQ ID NO. 21) or K-D/E-X-N-Z-S/T-K (SEQ ID NO. 22) (e.g. K-D-Q-N-A-T-K (SEQ ID NO. 23)) consensus sequence. Alternatively, 2, 3, 4, 5, 6 or 7 amino acids in the ClfA amino acid sequence (e.g. SEQ ID NO. 3 or a ClfA amino acid sequence at least 80%, 85%, 90%, 92%, 95%, 96%, 97%, 98% or 99% identical to SEQ ID NO. 3) may be replaced with a D/E-X-N-Z-S/T (SEQ ID NO. 21) or K-D/E-X-N-Z-S/T-K (SEQ ID NO. 22) (e.g. K-D-Q-N-A-T-K (SEQ ID NO. 23)) consensus sequence.

Introduction of a consensus sequence(s) selected from: D/E-X-N-Z-S/T (SEQ ID NO. 21) and K-D/E-X-N-Z-S/T-K (SEQ ID NO. 22) enables the polypeptide to be glycosylated. Thus, the present invention also provides a polypeptide of the invention wherein the polypeptide is glycosylated. In specific embodiments, the consensus sequences are introduced into specific regions of the ClfA amino acid sequence, e.g. surface structures of the protein, at the N or C termini of the protein, and/or in loops that are stabilized by disulfide bridges at the base of the protein. In an aspect of the invention, the position of the consensus sequence(s) provides improved glycosylation, for example increased yield. In an embodiment, the consensus sequence(s) selected from D/E-X-N-Z-S/T (SEQ ID NO. 21) and K-D/E-X-N-Z-S/T-K (SEQ ID NO. 22) (e.g. K-D-Q-N-A-T-K (SEQ ID NO. 23)) is located at the C-terminal end of the modified ClfA amino acid sequence at the C terminus, for example at a position 25 amino acids or less from the C terminus. In an embodiment, the consensus sequence is substituted for the amino acid corresponding to position 557 of SEQ ID NO. 1 (e.g. SEQ ID NOs 7-12).

In an embodiment, a consensus sequence selected from D/E-X-N-Z-S/T (SEQ ID NO. 21) and K-D/E-X-N-Z-S/T-K (SEQ ID NO. 22) (e.g. K-D-Q-N-A-T-K (SEQ ID NO. 23)) has been added or substituted for one or more amino acids residues 533-560 (e.g. in place of one or more amino acid residue(s) 550-560, or in place of amino acid residue Q547, P549, P551 or 1557, preferably 1557) of SEQ ID NO. 1 or in an equivalent position in an amino acid sequence at least 80%, 85%, 90%, 92%, 95%, 96%, 97%, 98% or 99% identical to SEQ ID NO. 1 (e.g. in an equivalent position in the amino acid sequence of SEQ ID NO. 3, i.e. Q327, D329, P331 or I337; for example, SEQ ID NOS. 7-12)

It will be understood by a person skilled in the art, that reference to "between amino acids . . . " (for example "between amino acids 533-560") is referring to the amino acid number counting consecutively from the N-terminus of the amino acid sequence, for example "between amino acids 533-560 . . . of SEQ ID NO. 1" refers to position in the amino acid sequence between the $533^{rd}$ and $560^{th}$ amino acid of SEQ ID NO. 1 including both the $533^{rd}$ and $560^{th}$ amino acid. Thus, in an embodiment where "a consensus sequence selected from D/E-X-N-Z-S/T (SEQ ID NO. 21) and K-D/E-X-N-Z-S/T-K (SEQ ID NO. 22) (e.g. K-D-Q-N-A-T-K (SEQ ID NO. 23)) has been added at or substituted for one or more amino acids between amino acid residues 533-560", the consensus sequence may have been added at or substituted for any one (or more) of amino acid numbers 533, 534, 535, 536, 537, 538, 539, 540, 541, 542, 543, 544, 545, 546, 547, 548, 549, 550, 551, 552, 553, 554, 555, 556, 557, 558, 559 or 560 in SEQ ID NO. 1. A person skilled in the art will understand that when the ClfA amino acid sequence is a variant and/or fragment of an amino acid sequence of SEQ ID NO. 1, such as an amino acid sequence at least 80%, 85%, 90%, 92%, 95%, 96%, 97%, 98% or 99% identical to SEQ ID NO. 1 or a fragment thereof such as SEQ ID NO 3 or SEQ ID NO: 4, the reference to "between amino acids . . . " refers to a the position that would be equivalent to the defined position, if this sequence was lined up with an amino acid sequence of SEQ ID NO. 1 in order to maximise the sequence identity between the two sequences (Sequence alignment tools are not limited to Clustal Omega (www(.)ebi(.)ac(.)ac(.)uk) MUSCLE (www(.)ebi(.)ac(.)uk), or T-coffee (www(.)tcoffee(.)org). In one aspect, the sequence alignment tool used is Clustal Omega (www(.)ebi(.)ac(.)ac(.)uk). For example, said amino acid numbers in SEQ ID NO: 1 correspond to amino acid numbers 313, 314, 315, 316, 317, 318, 319, 320, 321, 322, 323, 324, 325, 326, 327, 328, 329, 330, 331, 332, 333, 334, 335, 336, 337, 338, 339 or 340 of SEQ ID NO:3 and 4.

The addition or deletion of amino acids from the variant and/or fragment of SEQ ID NO.1 could lead to a difference in the actual amino acid position of the consensus sequence in the mutated sequence, however, by lining the mutated sequence up with the reference sequence, the amino acid in an equivalent position to the corresponding amino acid in the reference sequence can be identified and hence the appropriate position for addition or substitution of the consensus sequence can be established.

In an embodiment, the modified protein of the invention comprises at least 1, 2, 3 or 4 D/E-X-N-X-S/T (SEQ ID NO: 34) consensus sequences or exactly 1, 2, 3, 4, 5, or 6 D/E-X-N-X-S/T (SEQ ID NO: 34) consensus sequences. In an embodiment, the modified protein of the invention comprises at least 1, 2, 3 or 4 D/E-X-N-Z-S/T (SEQ ID NO. 21) consensus sequences or exactly 1, 2, 3, 4, 5, or 6 D/E-X-N-Z-S/T (SEQ ID NO. 22) consensus sequences. In an embodiment, the modified protein of the invention comprises at least 1, 2, 3 or 4 K-D/E-X-N-Z-S/T-K (SEQ ID NO. 22) consensus sequences or exactly 1, 2, 3, 4, 5, or 6 K-D/E-X-N-Z-S/T-K (SEQ ID NO. 22) consensus sequences. In an embodiment, the modified protein of the invention comprises a single consensus sequence selected from D/E-X-N-Z-S/T (SEQ ID NO. 21) and K-D/E-X-N-Z-S/T-K (SEQ ID NO. 22). In an embodiment, the consensus sequence is D/E-X-N-Z-S/T (SEQ ID NO. 21), wherein X is Q (glutamine) and Z is A (alanine), e.g. D-Q-N-A-T (SEQ ID NO: 35). In an embodiment, the consensus sequence is K-D/E-X-N-Z-S/T-K (SEQ ID NO. 22), wherein X is Q (glutamine) and Z is R (arginine), e.g. K-D-Q-N-R-T-K (SEQ ID NO. 24). In a preferred embodiment, the consensus sequence is K-D/E-X-N-Z-S/T-K (SEQ ID NO. 22), wherein X is Q (glutamine) and Z is A (alanine), e.g. K-D-Q-N-A-T-K (SEQ ID NO. 23).

Because the fibrinogen-binding activity of ClfA is required for it to act as a virulence factor, the ClfA protein may be modified to reduce or eliminate fibrinogen binding activity in order that it may be administered in vivo. A polypeptide may have one of the mutations described in WO2011/007004, for example mutations at one or preferably both of the amino acids corresponding to residues P336 and Y338 of SEQ ID NO: 1 (residues P116 and Y118 of SEQ ID NO: 3), for example P336S and/or Y338A. Exemplary sequences are those of SEQ ID NOs: 4-6 and, 10-12 and 25-27.

In an embodiment, the polypeptide of the invention further comprises a "peptide tag" or "tag", i.e. a sequence of amino acids that allows for the isolation and/or identification of the polypeptide. For example, adding a tag to a polypeptide of the invention can be useful in the purification of that protein and, hence, the purification of conjugate vaccines comprising the tagged modified ClfA protein. Exemplary tags that can be used herein include, without limitation, histidine (HIS) tags (e.g. hexa histidine-tag, or 6×His-Tag), FLAG-TAG, and HA tags. In one embodiment, the tag is a hexa-histidine tag. In certain embodiments, the tags used herein are removable, e.g. removal by chemical agents or by enzymatic means, once they are no longer needed, e.g. after the protein has been purified. Optionally the peptide tag is located at the C-terminus of the amino acid sequence. Optionally the peptide tag comprises six histidine residues at the C-terminus of the amino acid sequence. In one aspect, the modified ClfA protein of the invention comprises (or consists of) an amino acid sequence which is at least 80%, 85%, 90%, 92%, 95%, 97%, 98%, 99% or 100% identical to the sequence of SEQ ID NO. 4, 5, or 6, said amino acid sequence comprising a D/E-X-N-Z-S/T (SEQ ID NO. 21) consensus sequence wherein X and Z are independently any amino acid apart from proline (e.g. K-D/E-X-N-Z-S/T-K (SEQ ID NO. 22) or K-D-Q-N-A-T-K (SEQ ID NO. 23)) and a peptide tag (e.g. six histidine residues at the C-terminus of the amino acid sequence). Optionally, the polypeptide of the invention has an amino acid sequence at least 97%, 98%, 99% or 100% identical to SEQ ID NO. 25, 25 or 27.

In an embodiment, the polypeptide of the invention comprises a signal sequence which is capable of directing the ClfA protein to the periplasm of a host cell (e.g. bacterium). In a specific embodiment, the signal sequence is from E. coli flagellin (FlgI) [MIKFLSALILLLVTTAAQA (Seq ID NO. 13)]. In other embodiments, the signal sequence is from E. coli outer membrane porin A (OmpA) [MKKTAIAIAVA-LAGFATVAQA (Seq ID NO. 14)], E. coli maltose binding protein (MalE) [MKIKTGARILALSALTTMMFSASALA (Seq ID NO. 15)], Erwinia carotovorans pectate lyase (PelB) [MKYLLPTAAAGLLLLAAQPAMA (Seq ID NO. 16)], heat labile E. coli enterotoxin LTIIb [MSFKKIIKAF-VIMAALVSVQAHA (Seq ID NO. 17)], E. coli DsbA [MKKIWLALAGLVLAFSASA (Seq ID NO. 18)], TolB [MKQALRVAFGFLILWASVLHA (Seq ID NO. 19)] or SipA [MKMNKKVLLTSTMAASLLSVASVQAS (SEQ ID NO.20)]. In an embodiment, the signal sequence has an amino acid sequence at least 80%, 85%, 90%, 92%, 95%, 96%, 97%, 98%, 99% or 100% identical to a SEQ ID NO. 13-20. In one aspect, the signal sequence has an amino acid sequence at least 80%, 85%, 90%, 95%, 96%, 97%, 98%, 99% or 100% identical to *E. coli* flagellin signal sequence (FlgI) [MIKFLSALILLLVTTAAQA (Seq ID NO. 13)]. Exemplary modified ClfA sequences comprising a signal sequence are SEQ ID NOs: 5, 11 and 26.

In an embodiment, an additional amino acid residue (for example, serine or alanine) is added between the signal sequence and the start of the sequence of the mature protein, as in for example SEQ ID NO:s 5 and 11. Such an residue has the advantage of leading to more efficient cleavage of the leader sequence.

In one aspect, the polypeptide of the invention comprises (or consists of) an amino acid sequence which is at least 80%, 85%, 90%, 95%, 96%, 97%, 98%, 99% or 100% identical to the sequence of SEQ ID NO. 3, said amino acid sequence comprising: the amino acid substitutions P116 to S and Y118 to A, a D/E-X-N-Z-S/T (SEQ ID NO. 21) consensus sequence wherein X and Z are independently any amino acid apart from proline (e.g. K-D/E-X-N-Z-S/T-K (SEQ ID NO. 22) or K-D-Q-N-A-T-K (SEQ ID NO. 23)) and wherein said consensus sequence is preferably substituted for amino acid residue I337, a 6-His tag at the C-terminus of the amino acid sequence and optionally a signal sequence, preferably a FlgL signal sequence (SEQ ID NO: 13)) at the N-terminus of the signal sequence, optionally followed by an additional serine residue. In an embodiment, a modified ClfA protein of the invention has an amino acid sequence at least 97%, 98%, 99% or 100% identical to an amino acid sequence selected from SEQ ID NOs 10-12 or SEQ ID NOs. 25-27. In another embodiment, the present invention provides a polypeptide having an amino acid sequence selected from SEQ ID NOs 10-12 or SEQ ID NOs. 25-27.

A further aspect of the invention is a polynucleotide encoding a polypeptide of the invention. For example, a polynucleotide encoding a polypeptide, having a nucleotide sequence that encodes a polypeptide with an amino acid sequence that is at least 97%, 98%, 99% or 100% identical to any one of SEQ ID NOs. 10-12 or 25-26. For example, a polynucleotide encoding a polypeptide, having a nucleotide sequence that encodes a polypeptide with an amino acid sequence of any one of SEQ ID NOs. 10-12 or 25-27. A vector comprising such a polynucleotide is a further aspect of the invention.

Conjugates

The present invention also provides a conjugate (e.g. bioconjugate) comprising (or consisting of) a polypeptide of the invention, wherein the polypeptide is linked, e.g. covalently linked, to an antigen, preferably a polysaccharide or oligosaccharide antigen.

In an embodiment, the conjugate comprises a conjugate (e.g. bioconjugate) comprising (or consisting of) a polypeptide of the invention having an amino acid sequence which is at least 97%, 98%, 99% or 100% identical to the sequence of SEQ ID NOs. 4-12 or 25-27 covalently linked to an antigen, wherein the antigen is linked (either directly or through a linker) to an amino acid residue of the polypeptide.

In an embodiment, the polypeptide is covalently linked to the antigen through a chemical linkage obtainable using a chemical conjugation method (i.e. the conjugate is produced by chemical conjugation).

In an embodiment, the chemical conjugation method is selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al Infect. Immunity, 1983 245 256.

In general the following types of chemical groups on a polypeptide can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or $NH_2$. Aldehyde groups can be generated after different treatments such as: periodate, acid hydrolysis, hydrogen peroxide, etc.

Direct Coupling Approaches:

Saccharide-OH+CNBr or CDAP→cyanate ester+$NH_2$-Protein→conjugate

Saccharide-aldehyde+$NH_2$-Protein→Schiff base+NaCNBH3→conjugate

Saccharide-COOH+$NH_2$-Protein+EDAC→conjugate

Saccharide-$NH_2$+COOH-Protein+EDAC→conjugate

Indirect Coupling Via Spacer (Linker) Approaches:

Saccharide-OH+CNBr or CDAP→cyanate ester+$NH_2$—$NH_2$→saccharide-$NH_2$+COOH-Protein+EDAC→conjugate Saccharide-OH+CNBr or CDAP→cyanate ester+$NH_2$—SH→saccharide-SH+SH-Protein (native Protein with an exposed cysteine or obtained after modification of amino groups of the protein by SPDP for instance)→saccharide-S—S-Protein Saccharide-OH+CNBr or CDAP→cyanate ester+$NH_2$—SH→saccharide-SH+maleimide-Protein (modification of amino groups)→conjugate Saccharide-OH+CNBr or CDAP→cyanate ester+$NH_2$—SH→Saccharide-SH+haloacetylated-Protein→Conjugate Saccharide-COOH+EDAC+$NH_2$—$NH_2$→saccharide-$NH_2$+EDAC+COOH-Protein→conjugate Saccharide-COOH+EDAC+NH₂—SH→saccharide-SH+ SH-Protein (native Protein with an exposed cysteine or obtained after modification of amino groups of the protein by SPDP for instance)→saccharide-S—S-Protein Saccharide-COOH+EDAC+NH₂—SH→saccharide-SH+ maleimide-Protein (modification of amino groups)→conjugate Saccharide-COOH+EDAC+NH₂—SH→Saccharide-SH+haloacetylated-Protein→Conjugate Saccharide-Aldehyde+NH₂—NH₂→saccharide-NH₂+ EDAC+COOH-Protein→conjugate Note: instead of EDAC above, any suitable carbodiimide may be used.

In an embodiment, the antigen is directly linked to the polypeptide.

In an embodiment, the antigen is attached to the polypeptide via a linker. Optionally, the linker is selected from the group consisting of linkers with 4-12 carbon atoms, bifunctional linkers, linkers containing 1 or 2 reactive amino groups at the end, B-proprionamido, nitrophenyl-ethylamine, haloacyl halides, 6-aminocaproic acid and ADH. The activated saccharide may thus be coupled directly or via a spacer (linker) group to an amino group on the polypeptide. For example, the spacer could be cystamine or cysteamine to give a thiolated polysaccharide which could be coupled to the modified ClfA via a thioether linkage obtained after reaction with a maleimide-activated polypeptide (for example using GMBS (4-Maleimidobutyric acid N-hydroxysuccinimide ester)) or a haloacetylated polypeptide (for example using SIAB (succinimidyl (4-iodoacetyl)aminobenzoate), or SIA (succinimidyl iodoacetate), or SBAP (succinimidyl-3-(bromoacetamide)propionate)). In an embodiment, the cyanate ester (optionally made by CDAP chemistry) is coupled with hexane diamine or ADH (adipic acid dihydrazide) and the amino-derivatised saccharide is conjugated to the polypeptide using carbodiimide (e.g. 1-Ethyl-3-(3-dimethylaminopropyl)carbodiimide (EDAC or EDC)) chemistry via a carboxyl group on the protein modified ClfA. Such conjugates are described in PCT published application WO 93/15760 Uniformed Services University and WO 95/08348 and WO 96/29094.

In an embodiment, the amino acid residue on the polypeptide to which the antigen is linked is not an asparagine residue and in this case, the conjugate is typically produced by chemical conjugation. In an embodiment, the amino acid residue on the polypeptide to which the antigen is linked is selected from the group consisting of: Ala, Arg, Asp, Cys, Gly, Glu, Gln, His, Ile, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine or a tryptophan. Optionally, the antigen is covalently linked to amino acid on the polypeptide selected from: aspartic acid, glutamic acid, lysine, cysteine, tyrosine, histidine, arginine or tryptophan. Preferably, the antigen is linked to an asparagine residue.

In an embodiment, the amino acid residue on the polypeptide to which the antigen is linked is not part of the D/E-X-N-Z-S/T (SEQ ID NO. 21) and K-D/E-X-N-Z-S/T-K (SEQ ID NO. 22) consensus sequence. In an embodiment, the amino acid residue on the polypeptide to which the antigen is linked is not the asparagine residue in the D/E-X-N-Z-S/T (SEQ ID NO. 21) and K-D/E-X-N-Z-S/T-K (SEQ ID NO. 22) consensus sequence.

Alternatively, in another embodiment, the antigen is linked to an amino acid on the polypeptide selected from asparagine, aspartic acid, glutamic acid, lysine, cysteine, tyrosine, histidine, arginine or tryptophan (e.g. asparagine). In another embodiment, the amino acid residue on the polypeptide to which the antigen is linked is an asparagine residue. In another embodiment, the amino acid residue on the polypeptide to which the antigen is linked is part of the D/E-X-N-Z-S/T (SEQ ID NO. 21) and K-D/E-X-N-Z-S/T-K (SEQ ID NO. 22) consensus sequence (e.g. the asparagine in the D/E-X-N-Z-S/T (SEQ ID NO. 21) and K-D/E-X-N-Z-S/T-K (SEQ ID NO. 22) consensus sequence).

Polysaccharide Antigens

In an embodiment, one of the antigens in a conjugate (e.g. bioconjugate) of the invention is a saccharide such as a bacterial capsular saccharide, a bacterial lipopolysaccharide or a bacterial oligosaccharide. In an embodiment the antigen is a bacterial capsular saccharide.

The saccharides may be selected from a group consisting of: *Staphylococcus aureus* type 5 capsular saccharide, *Staphylococcus aureus* type 8 capsular saccharide, *N. meningitidis* serogroup A capsular saccharide (MenA), *N. meningitidis* serogroup C capsular saccharide (MenC), *N. meningitidis* serogroup Y capsular saccharide (MenY), *N. meningitidis* serogroup W capsular saccharide (MenW), *H. influenzae* type b capsular saccharide (Hib), Group B *Streptococcus* group I capsular saccharide, Group B *Streptococcus* group II capsular saccharide, Group B *Streptococcus* group III capsular saccharide, Group B *Streptococcus* group IV capsular saccharide, Group B *Streptococcus* group V capsular saccharide, Vi saccharide from *Salmonella typhi*, *N. meningitidis* LPS (such as L3 and/or L2), *M. catarrhalis* LPS, *H. influenzae* LPS, *Shigella* O-antigens, *P. aeruginosa* O-antigens, *E. coli* O-antigens or *S. pneumoniae* capsular polysaccharide.

In an embodiment, the antigen is a bacterial capsular saccharide from *Staphylococcus aureus*. The bacterial capsular saccharide from *Staphylococcus aureus* may be selected from a *Staphylococcus aureus* serotype 5 or 8 capsular saccharide. For example, the antigen may be an *Staphylococcus aureus* capsular saccharide from serotype 8.

In an embodiment of the invention, the antigen is a repeat unit of a bacterial capsular saccharide from *Staphylococcus aureus*. In an embodiment of the invention, the antigen comprises a repeat unit of a bacterial capsular saccharide from *Staphylococcus aureus* serotype 5 or 8.

In an embodiment of the invention, the antigen comprises a repeat unit of a bacterial capsular saccharide from *Staphylococcus aureus* serotype 8. In an embodiment of the invention, the antigen comprises:

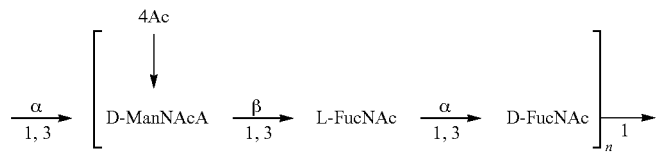

where 'n' is any whole number, but preferably as defined below (eg 2, 3, 4, 5, 6, 7, 8, 9, 10).

In an embodiment of the invention, the antigen comprises a repeat unit of a bacterial capsular saccharide from *Staphylococcus aureus* serotype 5. In an embodiment of the invention, the antigen comprises:

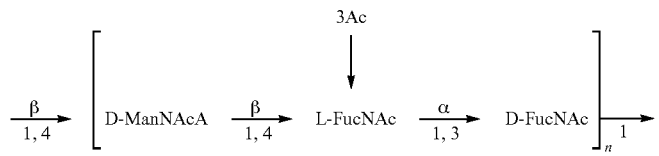

where 'n' is any whole number, but preferably as defined below (eg 2, 3, 4, 5, 6, 7, 8, 9, 10).

In an embodiment, the antigen is a polysaccharide or oligosaccharide. In an embodiment, the antigen comprises two or more monosaccharides, for example 2, 3, 4, 5, 6, 7, 8, 9, 10 or more monosaccharides. In an embodiment, the antigen is an oligosaccharide containing no more than 20, 15, 12, 10, 9, or 8 monosaccharides. In an embodiment, the antigen is an oligosaccharide containing no more than no more than 500, 400, 300, 200, 100, 90, 80, 70, 60, 50, 40, 30, 20, 10 or 5 monosaccharides.

Host Cell

The present invention also provides a host cell comprising:
 i) one or more nucleic acids that encode glycosyltransferase(s);
 ii) a nucleic acid that encodes an oligosaccharyl transferase;
 iii) a nucleic acid that encodes a polypeptide of the invention; and optionally
 iv) a nucleic acid that encodes a polymerase (e.g. wzy).

Host cells that can be used to produce the bioconjugates of the invention, include archea, prokaryotic host cells, and eukaryotic host cells. Exemplary prokaryotic host cells for use in production of the bioconjugates of the invention, without limitation, *Escherichia* species, *Shigella* species, *Klebsiella* species, *Xanthomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell is *E. coli*.

In an embodiment, the host cells used to produce the bioconjugates of the invention are engineered to comprise heterologous nucleic acids, e.g. heterologous nucleic acids that encode one or more carrier proteins and/or heterologous nucleic acids that encode one or more proteins, e.g. genes encoding one or more proteins. In a specific embodiment, heterologous nucleic acids that encode proteins involved in glycosylation pathways (e.g. prokaryotic and/or eukaryotic glycosylation pathways) may be introduced into the host cells of the invention. Such nucleic acids may encode proteins including, without limitation, oligosaccharyl transferases, epimerases, flippases, polymerases, and/or glycosyltransferases. Heterologous nucleic acids (e.g. nucleic acids that encode carrier proteins and/or nucleic acids that encode other proteins, e.g. proteins involved in glycosylation) can be introduced into the host cells of the invention using methods such as electroporation, chemical transformation by heat shock, natural transformation, phage transduction, and conjugation. In specific embodiments, heterologous nucleic acids are introduced into the host cells of the invention using a plasmid, e.g. the heterologous nucleic acids are expressed in the host cells by a plasmid (e.g. an expression vector). In another specific embodiment, heterologous nucleic acids are introduced into the host cells of the invention using the method of insertion described in International Patent application No. PCT/EP2013/068737 (published as WO 14/037585).

Thus, the present invention also provides a host cell comprising:
 i) one or more nucleic acids that encode glycosyltransferase(s);
 ii) a nucleic acid that encodes an oligosaccharyl transferase;
 iii) a nucleic acid that encodes a polypeptide of the invention;
 iv) a nucleic acid that encodes a polymerase (e.g. wzy); and
 vi) a nucleic acid that encodes a flippase (e.g. wxy).

In an embodiment, additional modifications may be introduced (e.g. using recombinant techniques) into the host cells of the invention. For example, host cell nucleic acids (e.g. genes) that encode proteins that form part of a possibly competing or interfering glycosylation pathway (e.g. compete or interfere with one or more heterologous genes involved in glycosylation that are recombinantly introduced into the host cell) can be deleted or modified in the host cell background (genome) in a manner that makes them inactive/dysfunctional (i.e. the host cell nucleic acids that are deleted/modified do not encode a functional protein or do not encode a protein whatsoever). In an embodiment, when nucleic acids are deleted from the genome of the host cells of the invention, they are replaced by a desirable sequence, e.g. a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-pyrophosphate biosynthesis genes (e.g. uppS (Undecaprenyl pyrophosphate synthase), uppP (Undecaprenyl diphosphatase)), Und-P recycling genes, metabolic enzymes involved in nucleotide activated sugar biosynthesis, enterobacterial common antigen cluster, and prophage O antigen modification clusters like the gtrABS cluster.

Such a modified prokaryotic host cell comprises nucleic acids encoding enzymes capable of producing a bioconjugate comprising an antigen, for example a saccharide antigen attached to a polypeptide of the invention. Such host cells may naturally express nucleic acids specific for production of a saccharide antigen, or the host cells may be made to express such nucleic acids, i.e. in certain embodiments said nucleic acids are heterologous to the host cells. In certain embodiments, one or more of said nucleic acids specific for production of a saccharide antigen are heterologous to the host cell and integrated into the genome of the host cell. In certain embodiments, the host cells of the invention comprise nucleic acids encoding additional enzymes active in the N-glycosylation of proteins, e.g. the host cells of the invention further comprise a nucleic acid encoding an oligosaccharyl transferase and/or one or more nucleic acids encoding other glycosyltransferases.

Nucleic acid sequences comprising capsular polysaccharide gene clusters can be inserted into the host cells of the invention. In a specific embodiment, the capsular polysaccharide gene cluster inserted into a host cell of the invention is a capsular polysaccharide gene cluster from an *E. coli* strain, a *Staphylococcus* strain (e.g. *S. aureus*), a *Streptococcus* strain (e.g. *S. pneumoniae, S. pyogenes, S. agalactiae*), or a *Burkholderia* strain (e.g. *B mallei, B. pseudomallei, B. thailandensis*). Disclosures of methods for making such host cells which are capable of producing bioconjugates are found in WO 06/119987, WO 09/104074, WO 11/62615, WO 11/138361, WO 14/57109, WO14/72405 and WO16/20499.

In an embodiment, the host cell comprises a nucleic acid that encodes a modified ClfA protein in a plasmid in the host cell.

Glycosylation Machinery

The host cells of the invention comprise, and/or can be modified to comprise, nucleic acids that encode genetic machinery (e.g. glycosyltransferases, flippases, polymerases, and/or oligosaccharyltransferases) capable of producing hybrid oligosaccharides and/or polysaccharides, as well as genetic machinery capable of linking antigens to the polypeptide of the invention.

*S. aureus* capsular polysaccharides are assembled on the bacterial membrane carrier lipid undecaprenyl pyrophosphate by a conserved pathway that shares homology to the polymerase-dependent pathway of O polysaccharide synthesis in Gram-negative bacteria. O antigen assembly is initiated by the transfer of a sugar phosphate from a DP-donor to undecaprenyl phosphate. The lipid linked O antigen is assembled at the cytoplasmic side of the inner membrane by sequential action of different glycosyltransferases. The glycolipid is then flipped to the periplasmic space and polymerised. By replacing the O antigen ligase WaaL with the oligosaccharyltransferase PglB, the polymerised O antigen can be transferred to a protein carrier rather than to the lipid A core.

Glycosyltransferases

The host cells of the invention comprise nucleic acids that encode glycosyltransferases that produce an oligosaccharide or polysaccharide repeat unit. In an embodiment, said repeat unit does not comprise a hexose at the reducing end, and said oligosaccharide or polysaccharide repeat unit is derived from a donor oligosaccharide or polysaccharide repeat unit that comprises a hexose at the reducing end.

In an embodiment, the host cells of the invention may comprise a nucleic acid that encodes a glycosyltransferase that assembles a hexose monosaccharide derivative onto undecaprenyl pyrophosphate (Und-PP). In one aspect, the glycosyltransferase that assembles a hexose monosaccharide derivative onto Und-PP is heterologous to the host cell and/or heterologous to one or more of the genes that encode glycosyltransferase(s). Said glycosyltransferase can be derived from, e.g. *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, the glycosyltransferase that assembles a hexose monosaccharide derivative onto Und-PP is wecA, optionally from *E. coli* (wecA can assemble GlcNAc onto UndP from UDP-GlcNAc). In an embodiment, the hexose monosaccharide is selected from the group consisting of glucose, galactose, rhamnose, arabinotol, fucose and mannose (e.g. galactose).

In an embodiment, the host cells of the invention may comprise nucleic acids that encode one or more glycosyltransferases capable of adding a monosaccharide to the hexose monosaccharide derivative assembled on Und-PP. In a specific embodiment, said one or more glycosyltransferases capable of adding a monosaccharide to the hexose monosaccharide derivative is the galactosyltransferase (wfeD) from *Shigella boydii*. In another specific embodiment, said one or more glycosyltransferases capable of adding a monosaccharide to the hexose monosaccharide derivative is the galactofuranosyltransferase (wbeY) from *E. coli*O28. In another specific embodiment, said one or more glycosyltransferases capable of adding a monosaccharide to the hexose monosaccharide derivative is the galactofuranosyltransferase (wfdK) from *E. coli* O167. Galf-transferases, such as wfdK and wbeY, can transfer Galf (Galactofuranose) from UDP-Galf to -GlcNAc-P-P-Undecaprenyl. In another specific embodiment, said one or more glycosyltransferases capable of adding a monosaccharide to the hexose monosaccharide derivative are the galactofuranosyltransferase (wbeY) from *E. coli* O28 and the galactofuranosyltransferase (wfdK) from *E. coli*O167.

In an embodiment, the host cells of the invention comprise nucleic acids that encode glycosyltransferases that assemble the donor oligosaccharide or polysaccharide repeat unit onto the hexose monosaccharide derivative.

In an embodiment, the glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative. Exemplary glycosyltransferases include galactosyltransferases (wciP), e.g. wciP from *E. coli* O21.

In one embodiment, the glycosyltransferases that assemble the donor oligosaccharide or polysaccharide repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide. Exemplary glycosyltransferases include glucosyltransferase (wciQ), e.g. wciQ from *E. coli* O21.

In an embodiment, a host cell of the invention comprises glycosyltransferases for synthesis of the repeat units of an oligosaccharide or polysaccharide selected from the *Staphylococcus aureus* CP5 or CP8 gene cluster. In a specific embodiment, the glycosyltransferases for synthesis of the repeat units of an oligosaccharide or polysaccharide are from the *Staphylococcus aureus* CP5 gene cluster. *S. aureus* CP5 and CP8 have a similar structure to *P. aeruginosa* O11 antigen synthetic genes, so these genes may be combined with *E. coli* monosaccharide synthesis genes to synthesise an undecaprenyl pyrophosphate-linked CP5 or CP8 polymer consisting of repeating trisaccharide units.

In an embodiment, a host cell of the invention comprises glycosyltransferases sufficient for synthesis of the repeat units of the CP5 or CP8 saccharide comprising capH, capI, capJ and/or capK from S. aureus CP5 or CP8. Optionally the host cell of the invention also comprises capD, capE, capF, capG, capL, capM, capN, capO, capP from S. aureus CP5 or CP8. Alternatively, the host cell of the invention also comprises wbjB, wbjC, wbjD, wbjE, wbjF, wbjL, wbpM, wzz and/or wzx from P. aeruginosa O11 and wecB, wecC from E. coli O16.

In an embodiment, a host cell of the invention comprises glycosyltransferases sufficient for synthesis of the repeat units of the CP5 saccharide comprising capH, capI, capJ and/or capK from S. aureus CP5. Optionally the host cell of the invention also comprises capD, capE, capF, capG, capL, capM, capN, capO, capP from S. aureus CP5. Alternatively, the host cell of the invention also comprises wbjB, wbjC, wbjD, wbjE, wbjF, wbjL, wbpM, wzz and/or wzx from P. aeruginosa O11 and wecB, wecC from E. coli O16.

In an embodiment, a host cell of the invention comprises glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative.

Oligosaccharyl Transferases

N-linked protein glycosylation—the addition of carbohydrate molecules to an asparagine residue in the polypeptide chain of the target protein—is the most common type of post-translational modification occurring in the endoplasmic reticulum of eukaryotic organisms. The process is accomplished by the enzymatic oligosaccharyltransferase complex (OST) responsible for the transfer of a preassembled oligosaccharide from a lipid carrier (dolichol phosphate) to an asparagine residue of a nascent protein within the conserved sequence Asn-X-Ser/Thr (where X is any amino acid except proline) in the Endoplasmic reticulum.

It has been shown that a bacterium, the food-borne pathogen Campylobacter jejuni, can also N-glycosylate its proteins (Wacker et al. Science. 2002; 298(5599):1790-3) due to the fact that it possesses its own glycosylation machinery. The machinery responsible for this reaction is encoded by a cluster called "pgl" (for protein glycosylation).

The C. jejuni glycosylation machinery can be transferred to E. coli to allow for the glycosylation of recombinant proteins expressed by the E. coli cells. Previous studies have demonstrated how to generate E. coli strains that can perform N-glycosylation (see, e.g. Wacker et al. Science. 2002; 298 (5599):1790-3; Nita-Lazar et al. Glycobiology. 2005; 15(4):361-7; Feldman et al. Proc Natl Acad Sci USA. 2005; 102(8):3016-21; Kowarik et al. EMBO J. 2006; 25(9):1957-66; Wacker et al. Proc Natl Acad Sci USA. 2006; 103(18): 7088-93; International Patent Application Publication Nos. WO2003/074687, WO2006/119987, WO 2009/104074, and WO/2011/06261, and WO2011/138361). PglB mutants having optimised properties are described in WO2016/107818. A preferred mutant is $PglB_{CUO\ N311V-K482R-D483H-A669V}$, as described in the Examples.

Oligosaccharyl transferases transfer lipid-linked oligosaccharides to asparagine residues of nascent polypeptide chains that comprise a N-glycosylation consensus motif, e.g. Asn-X-Ser(Thr), wherein X can be any amino acid except Pro; or Asp(Glu)-X-Asn-Z-Ser(Thr) (SEQ ID NO: 21), wherein X and Z are independently selected from any natural amino acid except Pro (see WO 2006/119987). See, e.g. WO 2003/074687 and WO 2006/119987, the disclosures of which are herein incorporated by reference in their entirety.

In an embodiment, the host cells of the invention comprise a nucleic acid that encodes an oligosaccharyl transferase. The nucleic acid that encodes an oligosaccharyl transferase can be native to the host cell, or can be introduced into the host cell using genetic approaches, as described above. In a specific embodiment, the oligosaccharyl transferase is an oligosaccharyl transferase from Campylobacter. In another specific embodiment, the oligosaccharyl transferase is an oligosaccharyl transferase from Campylobacter jejuni (i.e. pglB; see, e.g. Wacker et al. 2002, Science 298:1790-1793; see also, e.g. NCBI Gene ID: 3231775, UniProt Accession No. O86154). In another specific embodiment, the oligosaccharyl transferase is an oligosaccharyl transferase from Campylobacter lari (see, e.g. NCBI Gene ID: 7410986).

In a specific embodiment, the host cells of the invention comprise a nucleic acid sequence encoding an oligosaccharyl transferase, wherein said nucleic acid sequence encoding an oligosaccharyl transferase (e.g. pglB from Campylobacter jejuni) is integrated into the genome of the host cell.

In a specific embodiment, the host cells of the invention comprise a nucleic acid sequence encoding an oligosaccharyl transferase, wherein said nucleic acid sequence encoding an oligosaccharyl transferase (e.g. pglB from Campylobacter jejuni) is plasmid-borne.

In another specific embodiment, provided herein is a modified prokaryotic host cell comprising (i) a glycosyltransferase derived from an capsular polysaccharide cluster from S. aureus, wherein said glycosyltransferase is integrated into the genome of said host cell; (ii) a nucleic acid encoding an oligosaccharyl transferase (e.g. pglB from Campylobacter jejuni), wherein said nucleic acid encoding an oligosaccharyl transferase is plasmid-borne and/or integrated into the genome of the host cell; and (iii) a polypeptide of the invention, wherein said polypeptide is either plasmid-borne or integrated into the genome of the host cell. There is also provided a method of making a modified prokaryotic host cell comprising (i) integrating a glycosyltransferase derived from an capsular polysaccharide cluster from S. aureus into the genome of said host cell; (ii) integrating into the host cell one or more nucleic acids encoding an oligosaccharyl transferase (e.g. pglB from Campylobacter jejuni) which is plasmid-borne and/or integrated into the genome of the host cell; and (iii) integrating into a host cell a polypeptide of the invention either plasmid-borne or integrated into the genome of the host cell.

In specific embodiment is a host cell of the invention, wherein at least one gene of the host cell has been functionally inactivated or deleted, optionally wherein the waaL gene of the host cell has been functionally inactivated or deleted, optionally wherein the waaL gene of the host cell has been replaced by a nucleic acid encoding an oligosaccharyltransferase, optionally wherein the waaL gene of the host cell has been replaced by C. jejuni pglB.

Polymerases

In an embodiment, a polymerase (e.g. wzy) is introduced into a host cell of the invention (i.e. the polymerase is heterologous to the host cell). In an embodiment, the polymerase is a bacterial polymerase. In an embodiment, the polymerase is a capsular polysaccharide polymerase (e.g.

wzy) or an O antigen polymerase (e.g. wzy). In an embodiment, the polymerase is a capsular polysaccharide polymerase (e.g. wzy).

In an embodiment, a polymerase of a capsular polysaccharide biosynthetic pathway is introduced into a host cell of the invention.

In another specific embodiment, a polymerase of a capsular polysaccharide biosynthetic pathway of *Staphylococcus aureus* is introduced into a host cell of the invention.

In an embodiment, the polymerase introduced into the host cells of the invention is the wzy gene from a capsular polysaccharide gene cluster of *S. aureus* CP5 or CP8 (cap5J/cap8I).

In a specific embodiment, the polymerase introduced into the host cells of the invention is the wzy gene from a capsular polysaccharide gene cluster of CP8 (cap8I).

In another specific embodiment, said polymerase is incorporated (e.g. inserted into the genome of or plasmid expressed by) in said host cell as part of a *S. aureus* capsular polysaccharide cluster, wherein said *S. aureus* capsular polysaccharide cluster has been modified to comprise the wzy polymerase.

In a specific embodiment, a nucleic acid sequence encoding the *S. aureus* wzy polymerase is inserted into or expressed by the host cells of the invention. Thus, a host cell of the invention may further comprise an *S. aureus* wzy polymerase.

Flippases

In an embodiment, a flippase (wzx or homologue) is introduced into a host cell of the invention (i.e. the flippase is heterologous to the host cell). Thus, a host cell of the invention may further comprise a flippase. In an embodiment, the flippase is a bacterial flippase. Flippases translocate wild type repeating units and/or their corresponding engineered (hybrid) repeat units from the cytoplasm into the periplasm of host cells (e.g. *E. coli*). Thus, a host cell of the invention may comprise a nucleic acid that encodes a flippase (wzx).

In a specific embodiment, a flippase of a capsular polysaccharide biosynthetic pathway is introduced into a host cell of the invention.

In another specific embodiment, a flippase of a capsular polysaccharide biosynthetic pathway of *S. aureus* is introduced into a host cell of the invention. In certain embodiments, the flippase introduced into the host cells of the invention is the capK gene from a capsular polysaccharide gene cluster of *S. aureus* CP5 or CP8. In a specific embodiment, the flippase introduced into the host cells of the invention is the capK gene from a capsular polysaccharide gene cluster of CP8.

Other flippases that can be introduced into the host cells of the invention are for example from *Campylobacter jejuni* (e.g. pglK).

Enzymes that Modify Monosaccharides

Accessory Enzymes

In an embodiment, nucleic acids encoding one or more accessory enzymes are introduced into the host cells of the invention. Thus, a host cell of the invention may further comprise one or more of these accessory enzymes. Such nucleic acids encoding one or more accessory enzymes can be either plasmid-borne or integrated into the genome of the host cells of the invention. Exemplary accessory enzymes include, without limitation, epimerases, branching, modifying (e.g. to add cholins, glycerolphosphates, pyruvates), amidating, chain length regulating, acetylating, formylating, polymerizing enzymes.

In certain embodiments, enzymes that are capable of modifying monosaccharides are introduced into a host cell of the invention (i.e. the enzymes that are capable of modifying monosaccharides are heterologous to the host cell). Such enzymes include, e.g. epimerases and racemases. Thus, a host cell of the invention may further comprise an epimerase and/or racemase.

In an embodiment, the epimerases and racemases are from bacteria. In certain embodiments, the epimerases and/or racemases introduced into the host cells of the invention are from *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

In certain embodiments, the epimerase inserted into a host cell of the invention is an epimerase described in International Patent Application Publication No. WO2011/062615, the disclosure of which is incorporated by reference herein in its entirety. In one embodiment, the epimerase is the epimerase encoded by the Z3206 gene of *E. coli* strain O157. See, e.g. WO 2011/062615 and Rush et al. 2009, The Journal of Biological Chemistry 285:1671-1680, which is incorporated by reference herein in its entirety. In another embodiment, the epimerase is galE (UPD-Galactose epimerase) Z3206 and galE convert GlcNAc-P-P-undecaprenyl to GalNAc-P-P-undecaprenyl. In a specific embodiment, the host cells of the invention comprise a nucleic acid sequence encoding an epimerase, wherein said nucleic acid sequence encoding an epimerase is integrated into the genome of the host cell.

In an embodiment, a host cell of the invention further comprises a mutase, for example glf (UDP-galactopyranose mutase).

In an embodiment, a host cell of the invention further comprises RcsA (an activator of CP synthesis). RcsA is an unstable positive regulator required for the synthesis of colanic acid capsular polysaccharide in *Escherichia coli*.

Genetic Background

Exemplary host cells that can be used to generate the host cells of the invention include, without limitation, *Escherichia* species, *Shigella* species, *Klebsiella* species, *Xanthomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used herein is *E. coli*.

In an embodiment, the host cell genetic background is modified by, e.g. deletion of one or more genes. Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102: 3016-3021), the O antigen cluster (rfb or wb), enterobacterial common antigen cluster (wec), the lipid A core biosynthesis cluster (waa), and prophage O antigen modification clusters like the gtrABS cluster. In a specific embodiment, one or more of the waaL gene, gtrA gene, gtrBgene, gtrS gene, or a gene or genes from the wec cluster or a gene or genes from the rfb gene cluster are deleted or functionally inactivated from the genome of a prokaryotic host cell of the invention. In one embodiment, a host cell used herein is *E.* coli, wherein the waaL gene, gtrA gene, gtrBgene, gtrS gene are deleted or functionally inactivated from the genome of the host cell. In another embodiment, a host cell used herein is *E. coli*, wherein the waaL gene and gtrS gene are deleted or functionally inactivated from the genome of the host cell. In another embodiment, a host cell used herein is *E. coli*, wherein the waaL gene and genes from the wec cluster are deleted or functionally inactivated from the genome of the host cell.

Bioconjugates

The host cells of the invention can be used to produce bioconjugates comprising an antigen such as a polysaccharide or oligosaccharide antigen, for example a *Staphylococcus aureus* saccharide antigen linked to a polypeptide of the invention. Methods of producing bioconjugates using host cells are described for example in WO 2003/074687, WO 2006/119987 and WO2011/138361. Bioconjugates, as described herein, have advantageous properties over chemical conjugates of antigen-carrier protein, in that they require less chemicals in manufacture and are more consistent in terms of the final product generated.

In an embodiment, provided herein is a bioconjugate comprising a polypeptide linked to a *Staphylococcus aureus* antigen. In a specific embodiment, said *Staphylococcus aureus* antigen is a capsular saccharide (e.g. capsular polysaccharide). In a specific embodiment, provided herein is a bioconjugate comprising a polypeptide of the invention and an antigen selected from a capsular saccharide (e.g. capsular polysaccharide) of *Staphylococcus aureus* serotype CP5 or CP8. In a specific embodiment, provided herein is a bioconjugate comprising a polypeptide of the invention and an antigen from a capsular saccharide (e.g. capsular polysaccharide) of *Staphylococcus aureus* serotype CP8.

The bioconjugates of the invention can be purified for example, by chromatography (e.g. ion exchange, cationic exchange, anionic exchange, affinity, and sizing column chromatography), centrifugation, differential solubility, or by any other standard technique for the purification of proteins. See, e.g. Saraswat et al. 2013, Biomed. Res. Int. ID #312709 (p. 1-18); see also the methods described in WO 2009/104074. Further, the bioconjugates may be fused to heterologous polypeptide sequences described herein or otherwise known in the art to facilitate purification. For example, the ClfA protein may incorporate a peptide tag such as a hexahistidine tag for purification by cationic exchange. The actual conditions used to purify a particular bioconjugate will depend, in part, on the synthesis strategy and on factors such as net charge, hydrophobicity, and/or hydrophilicity of the bioconjugate, and will be apparent to those having skill in the art.

A further aspect of the invention is a process for producing a bioconjugate that comprises (or consists of) a polypeptide linked to a saccharide, said method comprising (i) culturing the host cell of the invention under conditions suitable for the production of proteins (and optionally under conditions suitable for the production of saccharides) and (ii) isolating the bioconjugate produced by said host cell.

A further aspect of the invention is a bioconjugate produced by the process of the invention, wherein said bioconjugate comprises a saccharide linked to a polypeptide.

Analytical Methods

Various methods can be used to analyze the structural compositions and sugar chain lengths of the bioconjugates of the invention.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide. See Bigge J C, Patel T P, Bruce J A, Goulding P N, Charles S M, Parekh R B: Nonselective and efficient fluorescent labeling of glycans using 2-amino benzamide and anthranilic acid. Anal Biochem 1995, 230(2):229-238. The labeled polysaccharides are separated on a GlycoSep-N column (GL Sciences) according to the HPLC protocol of Royle et al. See Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified.

In another embodiment, SDS-PAGE or capillary gel electrophoresis can be used to assess glycans and bioconjugates. Polymer length for the O antigen glycans is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the bioconjugate with different polymer chain lengths separate according to their electrophoretic mobilities. The first detectable repeating unit number ($n_1$) and the average repeating unit number ($n_{average}$) present on a bioconjugate are measured. These parameters can be used to demonstrate batch to batch consistency or polysaccharide stability.

In another embodiment, high mass MS and size exclusion HPLC could be applied to measure the size of the complete bioconjugates.

In another embodiment, an anthrone-sulfuric acid assay can be used to measure polysaccharide yields. See Leyva A, Quintana A, Sanchez M, Rodriguez E N, Cremata J, Sanchez J C: Rapid and sensitive anthrone-sulfuric acid assay in microplate format to quantify carbohydrate in biopharmaceutical products: method development and validation. Biologicals: journal of the International Association of Biological Standardization 2008, 36(2):134-141. In another embodiment, a Methylpentose assay can be used to measure polysaccharide yields. See, e.g. Dische et al. J Biol Chem. 1948 September; 175(2):595-603.

Change in Glycosylation Site Usage

To show that the site usage in a specific protein is changed in a multiple plasmid system as opposed to an inserted system, the glycosylation site usage must be quantified. Methods to do so are listed below.

Glycopeptide LC-MS/MS: bioconjugates are digested with protease(s), and the peptides are separated by a suitable chromatographic method (C18, Hydrophilic interaction HPLC HILIC, GlycoSepN columns, SE HPLC, AE HPLC), and the different peptides are identified using MS/MS. This method can be used with our without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by an earlier elution time from a SE HPLC column.

Homogeneity

Bioconjugate homogeneity (i.e. the homogeneity of the attached sugar residues) can be assessed using methods that measure glycan length and hydrodynamic radius.

Analytical Methods

Yield. Yield is measured as carbohydrate amount derived from a liter of bacterial production culture grown in a bioreactor under controlled and optimized conditions. After purification of bioconjugate, the carbohydrate yields can be directly measured by either the anthrone assay or ELISA using carbohydrate specific antisera. Indirect measurements are possible by using the protein amount (measured by BCA, Lowry, or Bradford assays) and the glycan length and structure to calculate a theoretical carbohydrate amount per gram of protein. In addition, yield can also be measured by drying the glycoprotein preparation from a volatile buffer and using a balance to measure the weight.

Stability Protein or glycoconjugate stability may be assayed by SDS-PAGE and/or Western blot, to detect the production of degradation products, or by CD, mass spectrometry or other methods known in the art. Stability may be assayed directly after production, or after storage for 1, 2, 3, 4 or more weeks, 1, 2, 3, 4, 5, 6 or more months at for example 4, 10, 20 or above 30 degrees Celsius.

Homogeneity. Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE. In addition, homogeneity can also mean that certain glycosylation site usage patterns change to a broader/narrower range. These factors can be measured by Glycopeptide LC-MS/MS.

Strain stability and reproducibility. Strain stability during bacterial fermentation in absence of selective pressure is measured by direct and indirect methods that confirm presence or absence of the recombinant DNA in production culture cells. Culture volume influence can be simulated by elongated culturing times meaning increased generation times. The more generations in fermentation, the more it is likely that a recombinant element is lost. Loss of a recombinant element is considered instability. Indirect methods rely on the association of selection cassettes with recombinant DNA, e.g. the antibiotic resistance cassettes in a plasmid. Production culture cells are plated on selective media, e.g. LB plates supplemented with antibiotics or other chemicals related to a selection system, and resistant colonies are considered as positive for the recombinant DNA associated to the respective selection chemical. In the case of a multiple plasmid system, resistant colonies to multiple antibiotics are counted and the proportion of cells containing all three resistances is considered the stable population. Alternatively, quantitative PCR can be used to measure the amount of recombinant DNA of the three recombinant elements in the presence, absence of selection, and at different time points of fermentation. Thus, the relative and absolute amount of recombinant DNA is measured and compared. Reproducibility of the production process is measured by the complete analysis of consistency batches by the methods stated in this application.

Immunogenic Compositions

The polypeptides and conjugates (e.g. bioconjugate), of the invention are particularly suited for inclusion in immunogenic compositions and vaccines. The present invention provides an immunogenic composition comprising the polypeptide of the invention, or the conjugate of the invention, or the bioconjugate of the invention.

Also provided is a method of making the immunogenic composition of the invention comprising the step of mixing the polypeptide or the conjugate (e.g. bioconjugate) of the invention with a pharmaceutically acceptable excipient or carrier.

Immunogenic compositions comprise an immunologically effective amount of the polypeptide or conjugate (e.g. bioconjugate) of the invention, as well as any other components. By "immunologically effective amount", it is meant that the administration of that amount to an individual, either as a single dose or as part of a series is effective for treatment or prevention. This amount varies depending on the health and physical condition of the individual to be treated, age, the degree of protection desired, the formulation of the vaccine and other relevant factors. It is expected that the amount will fall in a relatively broad range that can be determined through routine trials.

Immunogenic compositions if the invention may also contain diluents such as water, saline, glycerol etc. Additionally, auxiliary substances, such as wetting or emulsifying agents, pH buffering substances, polyols and the like may be present.

The immunogenic compositions comprising the polypeptide of the invention or conjugates (or bioconjugates) may comprise any additional components suitable for use in pharmaceutical administration. In specific embodiments, the immunogenic compositions of the invention are monovalent formulations. In other embodiments, the immunogenic compositions of the invention are multivalent formulations, e.g. bivalent, trivalent, and tetravalent formulations. For example, a multivalent formulation comprises more than one antigen for example more than one conjugate.

The immunogenic composition of the invention optionally further comprise additional antigens. Examples of such additional antigens are *S. aureus* proteins or capsular polysaccharides.

Vaccines

The present invention also provides a vaccine comprising an immunogenic composition of the invention and a pharmaceutically acceptable excipient or carrier.

Pharmaceutically acceptable excipients and carriers can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example, laurel sarcosine and/or polysorbate (e.g. TWEEN™ 80). Examples of stabilizing agents also include poloxamer (e.g. poloxamer 124, poloxamer 188, poloxamer 237, poloxamer 338 and poloxamer 407). The pharmaceutically acceptable excipient may include a non-ionic surfactant, for example polyoxyethylene sorbitan fatty acid esters, Polysorbate-80 (TWEEN™ 80), Polysorbate-60 (TWEEN™ 60), Polysorbate-40 (TWEEN™ 40) and Polysorbate-20 (TWEEN™ 20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are described, for example, in Remington's Pharmaceutical Sciences, by E. W. Martin, Mack Publishing Co. Easton, PA, 5th Edition (975).

In an embodiment, the immunogenic composition or vaccine of the invention additionally comprises one or more buffers, e.g. phosphate buffer and/or sucrose phosphate glutamate buffer. In other embodiments, the immunogenic composition or vaccine of the invention does not comprise a buffer.

In an embodiment, the immunogenic composition or vaccine of the invention additionally comprises one or more salts, e.g. sodium chloride, calcium chloride, sodium phosphate, monosodium glutamate, and aluminum salts (e.g. aluminum hydroxide, aluminum phosphate, alum (potassium aluminum sulfate), or a mixture of such aluminum salts). In other embodiments, the immunogenic composition or vaccine of the invention does not comprise a salt.

The immunogenic composition or vaccine of the invention may additionally comprise a preservative, e.g. a mercury derivative thimerosal. In a specific embodiment, the immunogenic composition or vaccine of the invention comprises 0.001% to 0.01% thimerosal. In other embodiments, the immunogenic composition or vaccine of the invention do not comprise a preservative.

The vaccine or immunogenic composition of the invention may also comprise an antimicrobial, typically when package in multiple dose format. For example, the immunogenic composition or vaccine of the invention may comprise 2-phenoxyethanol.

The vaccine or immunogenic composition of the invention may also comprise a detergent e.g. polysorbate, such as TWEEN™ 80. Detergents are generally present at low levels e.g. <0.01%, but higher levels have been suggested for stabilising antigen formulations e.g. up to 10%.

The immunogenic compositions of the invention can be included in a container, pack, or dispenser together with instructions for administration.

The immunogenic compositions or vaccines of the invention can be stored before use, e.g. the compositions can be stored frozen (e.g. at about −20° C. or at about −70° C.); stored in refrigerated conditions (e.g. at about 4° C.); or stored at room temperature.

The immunogenic compositions or vaccines of the invention may be stored in solution or lyophilized. In an embodiment, the solution is lyophilized in the presence of a sugar such as sucrose, trehalose or lactose. In another embodiment, the vaccines of the invention are lyophilized and extemporaneously reconstituted prior to use.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Adjuvants

In an embodiment, the immunogenic compositions or vaccines of the invention comprise, or are administered in combination with, an adjuvant. The adjuvant for administration in combination with an immunogenic composition or vaccine of the invention may be administered before, concomitantly with, or after administration of said immunogenic composition or vaccine. In some embodiments, the term "adjuvant" refers to a compound that when administered in conjunction with or as part of an immunogenic composition of vaccine of the invention augments, enhances and/or boosts the immune response to a bioconjugate, but when the compound is administered alone does not generate an immune response to the polypeptide/conjugate/bioconjugate. In some embodiments, the adjuvant generates an immune response to the polypeptide, conjugate or bioconjugate and does not produce an allergy or other adverse reaction.

In an embodiment, the immunogenic composition or vaccine of the invention is adjuvanted. Adjuvants can enhance an immune response by several mechanisms including, e.g. lymphocyte recruitment, stimulation of B and/or T cells, and stimulation of macrophages. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS01 (GlaxoSmithKline), AS03 (GlaxoSmithKline), AS04 (GlaxoSmithKline), polysorbate 80 (TWEEN™ 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al. in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al. N. Engl. J. Med. 336, 86-91 (1997)). Another adjuvant is CpG (Bioworld Today, Nov. 15, 1998).

In one aspect of the invention, the adjuvant is an aluminum salt such as aluminum hydroxide gel (alum) or aluminium phosphate.

In another aspect of the invention, the adjuvant is selected to be a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen. It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p145-173).

Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); MPL, e.g. 3D-MPL and the saponin QS21 in a liposome, for example a liposome comprising cholesterol and DPOC; and a combination of monophosphoryl lipid A, for example 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1].

Unmethylated CpG containing oligonucleotides (WO 96/02555) are also preferential inducers of a TH1 response and are suitable for use in the present invention.

The vaccine or immunogenic composition of the invention may contain an oil in water emulsion, since these have been suggested to be useful as adjuvant compositions (EP 399843; WO 95/17210). Oil in water emulsions such as those described in WO95/17210 (which discloses oil in water emulsions comprising from 2 to 10% squalene, from 2 to 10% alpha tocopherol and from 0.3 to 3% TWEEN© 80 and their use alone or in combination with QS21 and/or 3D-MPL), WO99/12565 (which discloses oil in water emulsion compositions comprising a metabolisable oil, a saponin and a sterol and MPL) or WO99/11241 may be used. Further oil in water emulsions such as those disclosed in WO 09/127676 and WO 09/127677 are also suitable. In a specific embodiment, the immunogenic composition or vaccine additionally comprises a saponin, for example QS21. The immunogenic composition or vaccine may also comprise an oil in water emulsion and tocopherol (WO 95/17210).

Method of Administration

Immunogenic compositions or vaccines of the invention may be used to protect or treat a mammal susceptible to infection, by means of administering said immunogenic composition or vaccine via systemic or mucosal route. These administrations may include injection via the intramuscular (IM), intraperitoneal, intradermal (ID) or subcutaneous routes; or via mucosal administration to the oral/alimentary, respiratory, genitourinary tracts. For example, intranasal (IN) administration may be used for the treatment of pneumonia or otitis media (as nasopharyngeal carriage of pneumococci can be more effectively prevented, thus attenuating infection at its earliest stage). Although the immunogenic composition or vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, however in one particular aspect of the invention it is present in combination with the polypeptide component of the immunogenic composition or vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

In one aspect, the immunogenic composition or vaccine of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

In another aspect, the immunogenic composition or vaccine of the invention is administered by the intradermal administration. Human skin comprises an outer "horny" cuticle, called the stratum corneum, which overlays the epidermis. Underneath this epidermis is a layer called the dermis, which in turn overlays the subcutaneous tissue. The conventional technique of intradermal injection, the "mantoux procedure", comprises steps of cleaning the skin, and then stretching with one hand, and with the bevel of a narrow gauge needle (26 to 31 gauge) facing upwards the needle is inserted at an angle of between 10 to 15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

In another aspect, the immunogenic composition or vaccine of the invention is administered by the intranasal administration. Typically, the immunogenic composition or vaccine is administered locally to the nasopharyngeal area, e.g. without being inhaled into the lungs. It is desirable to use an intranasal delivery device which delivers the immunogenic composition or vaccine formulation to the nasopharyngeal area, without or substantially without it entering the lungs. Suitable devices for intranasal administration of the vaccines according to the invention are spray devices. Suitable commercially available nasal spray devices include ACCUSPRAY™ (Becton Dickinson).

In an embodiment, spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO91/13281 and EP311 863 and EP516636, incorporated herein by reference. Such devices are commercially available from Pfeiffer GmbH and are also described in Bommer, R. Pharmaceutical Technology Europe, September 1999.

In another embodiment, intranasal devices produce droplets (measured using water as the liquid) in the range 1 to 200 μm, e.g. 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Following an initial vaccination, subjects may receive one or several booster immunizations adequately spaced.

The immunogenic composition or vaccine of the present invention may be used to protect or treat a mammal, e.g. human, susceptible to infection, by means of administering said immunogenic composition or vaccine via a systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any polypeptide, conjugate or bioconjugate of the invention for optimal coordination of the immune responses with respect to each other). For co-administration, the optional adjuvant may be present in any or all of the different administrations. In addition to a single route of administration, 2 different routes of administration may be used. For example, polysaccharide conjugates may be administered IM (or ID) and the polypeptide, conjugate or bioconjugate of the invention may be administered IN (or ID). In addition, the immunogenic compositions or vaccines of the invention may be administered IM for priming doses and IN for booster doses.

Dosage

The amount of conjugate antigen in each immunogenic composition or vaccine dose is selected as an amount which induces an immunoprotective response without significant, adverse side effects in typical vaccines. Such amount will vary depending upon which specific immunogen is employed and how it is presented. The content of polypeptide will typically be in the range 1-100 μg, suitably 5-50 μg. The content of saccharide will typically be in the range 0.1-10 μg, suitably 1-5 μg.

A dose which is in a volume suitable for human use is generally between 0.25 and 1.5 ml, although, for administration to the skin a lower volume of between 0.05 ml and 0.2 ml may be used. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the paediatric population, a human dose may be less than 0.5 ml such as between 0.25 and 0.5 ml.

Prophylactic and Therapeutic Uses

The present invention also provides methods of treating and/or preventing bacterial infections of a subject comprising administering to the subject a polypeptide, conjugate or bioconjugate of the invention. The polypeptide, conjugate or bioconjugate may be in the form of an immunogenic composition or vaccine. In a specific embodiment, the immunogenic composition or vaccine of the invention is used in the prevention of infection of a subject (e.g. human subjects) by a bacterium. Bacterial infections that can be treated and/or prevented using the polypeptide, conjugate or bioconjugate of the invention include those caused by *Staphylococcus* species, *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, the immunogenic composition or vaccine of the invention is used to treat or prevent an infection by *Staphylococcus* species (e.g. *Staphylococcus aureus*).

Also provided herein are methods of inducing an immune response in a subject against a bacterium, comprising administering to the subject a polypeptide, or conjugate or bioconjugate of the invention (or immunogenic composition or vaccine). In one embodiment, said subject has bacterial infection at the time of administration. In another embodiment, said subject does not have a bacterial infection at the time of administration. The polypeptide, conjugate or bioconjugate of the invention can be used to induce an immune response against *Staphylococcus* species, *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, polypeptide, or conjugate or bioconjugate of the invention is used to induce an immune response against *Staphylococcus* species (e.g. *Staphylococcus aureus*).

Also provided herein are methods of inducing the production of opsonophagocytic antibodies in a subject against a bacterium, comprising administering to the subject a polypeptide, or conjugate or bioconjugate of the invention (or immunogenic composition or vaccine). In one embodiment, said subject has bacterial infection at the time of administration. In another embodiment, said subject does not have a bacterial infection at the time of administration. The polypeptide, or conjugate or bioconjugate of the invention (or immunogenic composition or vaccine) provided herein can be used to induce the production of opsonophagocytic antibodies against *Staphylococcus* species, *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, a polypeptide, or conjugate or bioconjugate of the invention (or immunogenic composition or vaccine) is used to induce the production of opsonophagocytic antibodies against *Staphylococcus* species (e.g. *Staphylococcus aureus*).

For example, the immunogenic composition or vaccine of the invention may be used to prevent against *S. aureus* infection, including a nosocomial infection. More particularly, the subject may be protected against a skin infection, pneumonia, meningitis, osteomyelitis endocarditis, toxic shock syndrome, and/or septicaemia. The invention is also useful for protecting against *S. aureus* infection of a subject's bones and joints (and thus for preventing disorders including, but not limited to, osteomyelitis, septic arthritis, and prosthetic joint infection). In many cases these disorders may be associated with the formation of a S. aureus biofilm.

S. aureus infects various mammals (including cows, dogs, horses, and pigs), but the preferred mammal for use with the invention is a human. The human can be a child (e.g. a toddler or infant), a teenager, or an adult. In some embodiments the human may have a prosthetic bone or joint, or may be a patient awaiting elective surgery, in particular an intended recipient of a prosthetic bone or joint (e.g. a pre-operative orthopedic surgery patient). The vaccines are not suitable solely for these groups, however, and may be used more generally in a human population.

The vaccine preparations of the present invention may be used to protect or treat a human susceptible to S. aureus infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

In an embodiment, the present invention is an improved method to elicit an immune response in infants (defined as 0-2 years old in the context of the present invention) by administering a therapeutically effective amount of an immunogenic composition or vaccine of the invention (a paediatric vaccine). In an embodiment, the vaccine is a paediatric vaccine.

In an embodiment, the present invention is an improved method to elicit an immune response in the elderly population (in the context of the present invention a patient is considered elderly if they are 50 years or over in age, typically over 55 years and more generally over 60 years) by administering a therapeutically effective amount of the immunogenic composition or vaccine of the invention. In an embodiment, the vaccine is a vaccine for the elderly.

The present invention provides a method for the treatment or prevention of *Staphylococcus aureus* infection in a subject in need thereof comprising administering to said subject a therapeutically effective amount of the polypeptide of the invention, or the conjugate of the invention, or the bioconjugate of the invention, or the immunogenic composition or vaccine of the invention.

The present invention provides a method of immunising a human host against *Staphylococcus aureus* infection comprising administering to the host an immunoprotective dose of the polypeptide of the invention, or the conjugate of the invention, or the bioconjugate of the invention, or the immunogenic composition or vaccine of the invention.

The present invention provides a method of inducing an immune response to *Staphylococcus aureus* in a subject, the method comprising administering a therapeutically or prophylactically effective amount of the polypeptide of the invention, or the conjugate of the invention, or the bioconjugate of the invention, or the immunogenic composition or vaccine of the invention.

The present invention provides a polypeptide of the invention, or the conjugate of the invention, or the bioconjugate of the invention, or the immunogenic composition or vaccine of the invention for use in the treatment or prevention of a disease caused by *Staphylococcus aureus* infection.

The present invention provides use of the polypeptide of the invention, or the conjugate of the invention, or the bioconjugate of the invention in the manufacture of a medicament for the treatment or prevention of a disease caused by *Staphylococcus aureus* infection.

The disease caused by S. aureus infection may be, for example, a skin infection, pneumonia, meningitis, S. aureus infection of a subject's bones and joints (e.g. septic arthritis, prosthetic joint infection or osteomyelitis) endocarditis, toxic shock syndrome, and/or septicaemia. The disease may be a nosocomial infection.

All references or patent applications cited within this patent specification are incorporated by reference herein.

Aspects of the invention are summarised in the subsequence numbered paragraphs:

1. A polypeptide comprising an amino acid sequence of SEQ ID NO. 3 or an amino acid sequence at least 80%, 85%, 90%, 92%, 95%, 96%, 97%, 98% or 99% identical to SEQ ID NO. 3, modified in that the amino acid sequence comprises one or more consensus sequence (s) selected from: D/E-X-N-Z-S/T (SEQ ID NO. 21) and K-D/E-X-N-Z-S/T-K (SEQ ID NO. 22), wherein X and Z are independently any amino acid apart from proline; wherein said consensus sequence has been added at, or substituted for, one or more amino acids between amino acid residues 313-340 of SEQ ID NO: 3 or at an equivalent position within an amino acid sequence at least 80%, 85%, 90%, 92%, 95%, 96%, 97%, 98% or 99% identical to SEQ ID NO. 3.

2. The polypeptide of paragraph 1, wherein said consensus sequence has been substituted for amino acid residue Q327, D329, P331 or I337 in SEQ ID NO. 3, or substituted in an amino acid sequence at least 80%, 85%, 90%, 92%, 95%, 96%, 97%, 98% or 99% identical to SEQ ID NO. 3 at an amino acid position equivalent to amino acid residue Q327, D329, or I337 in SEQ ID NO. 3.

3. The polypeptide of paragraph 2, containing a single consensus sequence that has been substituted for amino acid residue I337 in SEQ ID NO. 3, or substituted in an amino acid sequence at least 80%, 85%, 90%, 92%, 95%, 96%, 97%, 98% or 99% identical to SEQ ID NO. 3 at an amino acid position equivalent to amino acid residue I337 in SEQ ID NO. 3.

4. The polypeptide of any one of paragraphs 1-3, wherein X is Q (glutamine) and Z is A (alanine) (e.g. K-D-Q-N-A-T-K (SEQ ID NO. 23)).

5. The polypeptide of any one of paragraphs 1-4, wherein the amino acid sequence is further modified by at least one amino acid substitution selected from P116 to S and Y118 to A with reference to the amino acid sequence of SEQ ID NO. 3 (or an equivalent position in an amino acid sequence at least 80%, 85%, 90%, 92%, 95%, 96%, 97%, 98% or 99% identical to SEQ ID NO. 3), optionally comprising the sequence of any one of SEQ ID NOs 4-5 or 10-12.

6. A polypeptide according to paragraph 5, comprising (or consisting of) an amino acid sequence which is at least 80%, 85%, 90%, 92%, 95%, 96%, 97%, 98%, 99% or 100% identical to the sequence of SEQ ID NO. 3, said amino acid sequence comprising a D/E-X-N-Z-S/T (SEQ ID NO. 21) or K-D/E-X-N-Z-S/T-K (SEQ ID NO. 22) consensus sequence, wherein X and Z are independently any amino acid apart from proline, substituted for the amino acid at position I337 in SEQ ID NO. 3, or substituted in an amino acid sequence at least 80%, 85%, 90%, 92%, 95%, 96%, 97%, 98% or 99% identical to SEQ ID NO. 3 at an amino acid position equivalent to amino acid residue Q327, D329, or I337 in SEQ ID NO. 3.

7. The polypeptide of any one of paragraphs 1-6, which has an additional serine residue at the N-terminus, optionally said polypeptide having an amino acid sequence at least 97%, 98%, 99% or 100% identical to SEQ ID NO. 6 or SEQ ID NO. 12; and/or an additional glycine or glycine-serine residue at the C-terminus, optionally said polypeptide having an amino acid sequence at least 97%, 98%, 99% or 100% identical to SEQ ID NO: 32.

8. The polypeptide of any one of paragraphs 1-7, wherein the amino acid sequence further comprises a signal sequence which is capable of directing the polypeptide to the periplasm of a host cell (e.g. bacterium), optionally said signal sequence being selected from SEQ ID NO. 13-20, optionally said polypeptide having an amino acid sequence at least 97%, 98%, 99% or 100% identical to SEQ ID NO. 5 or SEQ ID NO. 11.

9. The polypeptide of any one of paragraphs 1-8, wherein the amino acid sequence further comprises a peptide tag which is useful for the purification of the ClfA protein, optionally said peptide tag comprising six histidine residues and optionally said peptide tag located at the C-terminus of the amino acid sequence, optionally said polypeptide having an amino acid sequence at least 97%, 98%, 99% or 100% identical to SEQ ID NO: 25, SEQ ID NO: 26, or SEQ ID NO: 27.

10. The polypeptide of any one of paragraphs 1-9, wherein the polypeptide is glycosylated.

11. A conjugate (e.g. bioconjugate) comprising a polypeptide of any one of paragraphs 1-10, wherein the polypeptide is linked to an antigen, e.g. a polysaccharide or oligosaccharide antigen.

12. The conjugate according to paragraph 11, wherein the conjugate is covalently linked to the antigen through a chemical linkage obtainable using a chemical conjugation method, optionally selected from the group consisting of carbodiimide chemistry, reductive animation, cyanylation chemistry (for example CDAP chemistry), maleimide chemistry, hydrazide chemistry, ester chemistry, and N-hydroysuccinimide chemistry either directly or via a linker.

13. The conjugate (e.g. bioconjugate) of paragraph 11 or paragraph 12, wherein the antigen is linked to an amino acid on the polypeptide selected from asparagine, aspartic acid, glutamic acid, lysine, cysteine, tyrosine, histidine, arginine or tryptophan (e.g. asparagine).

14. The conjugate (e.g. bioconjugate) of any one of paragraphs 11-13, wherein the antigen is a saccharide, optionally a bacterial capsular saccharide (e.g. from *Staphylococcus aureus*) optionally selected from a *S. aureus* serotype 5 or 8 capsular saccharide.

15. The conjugate (e.g. bioconjugate) of paragraph 14, wherein the antigen is a bacterial capsular saccharide from *S. aureus* serotype 8.

16. A polynucleotide encoding the polypeptide of any one of paragraphs 1-10.

17. A vector comprising the polynucleotide of paragraph 16.

18. A host cell comprising:
    one or more nucleic acids that encode glycosyltransferase(s);
    a nucleic acid that encodes an oligosaccharyl transferase;
    a nucleic acid that encodes a polypeptide according to any one of paragraphs 1-10;
    and optionally
    a nucleic acid that encodes a polymerase (e.g. wzy).

19. The host cell of paragraph 18, wherein said host cell comprises (a) a glycosyltransferase that assembles a hexose monosaccharide derivative onto undecaprenyl pyrophosphate (Und-PP) and (b) one or more glycosyltransferases capable of adding a monosaccharide to the hexose monosaccharide derivative assembled on Und-PP.

20. The host cell of paragraph 19, wherein said glycosyltransferase that assembles a hexose monosaccharide derivative onto Und-PP is heterologous to the host cell and/or heterologous to one or more of the genes that encode glycosyltransferase(s) optionally wherein said glycosyltransferase that assembles a hexose monosaccharide derivative onto Und-PP is from *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species, optionally wecA (e.g. wecA from *E. coli*).

21. The host cell of any one of paragraphs 18-20, wherein said hexose monosaccharide derivative is any monosaccharide in which C-2 position is modified with an acetamido group such as N-acetylglucosamine (GlcNAc), N-acetylgalactoseamine (GalNAc), 2,4-Diacetamido-2,4,6-trideoxyhexose (DATDH). N-acetylfucoseamine (FucNAc), or N-acetylquinovosamine (QuiNAc).

22. The host cell of any one of paragraphs 18-21, wherein said one or more glycosyltransferases capable of adding a monosaccharide to the hexose monosaccharide derivative assembled on Und-PP is the galactofuranosyltransferase (wbeY) from *E. coli* O28 or the galactofuranosyltransferase (wfdK) from *E. coli* O167 or are the galactofuranosyltransferase (wbeY) from *E. coli* O28 and the galactofuranosyltransferase (wfdK) from *E. coli* O167.

23. The host cell of any one of paragraphs 18-22 wherein the host cell comprises glycosyltransferases sufficient for synthesis of repeat units of the *S. aureus* CP5 saccharide comprising capH, capI, capJ and/or capK from *S. aureus* CP5 and optionally capD, capE, capF, capG, capL, capM, capN, capO and/or capP from *S. aureus* CP5.

24. The host cell of any one of paragraphs 18-23 wherein the host cell comprises glycosyltransferases sufficient for synthesis repeat units of the *S. aureus* CP5 saccharide comprising capH, capI, capJ and/or capK from *S. aureus* CP5 and optionally wbjB, wbjC, wbjD, wbjE, wbjF, wbjL, wbpM, wzz and/or wzx from *P. aeruginosa* O11 and wecB and/or wecC from *E. coli* O16.

25. The host cell of any one of paragraphs 18-24 wherein the oligosaccharyl transferase is derived from *Campylobacter jejuni*, optionally wherein said oligosaccharyl transferase is pglB of *C. jejuni*, optionally wherein the pglB gene of *C. jejuni* is integrated into the host cell genome and optionally wherein at least one gene of the host cell has been functionally inactivated or deleted, optionally wherein the waaL gene of the host cell has been functionally inactivated or deleted, optionally wherein the waaL gene of the host cell has been replaced by a nucleic acid encoding an oligosaccharyltransferase, optionally wherein the waaL gene of the host cell has been replaced by *C. jejuni* pglB.

26. The host cell of any one of paragraphs 18-25, wherein said host cell comprises a nucleic acid that encodes a capsular polysaccharide polymerase (e.g. wzy) or an O antigen polymerase (e.g. wzy), optionally said capsular polysaccharide polymerase is from *Staphylococcus aureus*, optionally from *S. aureus* CP5 or CP8.
27. The host cell of any one of paragraphs 18-26, wherein said host cell comprises a nucleic acid that encodes a flippase (wzx), optionally wherein said flippase is from *Staphylococcus aureus*, optionally from *S. aureus* CP5 or CP8.
28. The host cell of any one of paragraphs 18-27, wherein said host cell further comprises an enzyme capable of modifying a monosaccharide, optionally an epimerase, optionally wherein said epimerase is from *Escherichia* species, *Shigella* species, *Klebsiella* species, *Xanthomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species, optionally wherein said epimerase is from *E. coli*, optionally Z3206 from *E. coli* O157 or galE.
29. The host cell of any one of paragraphs 18-28, wherein the nucleic acid that encodes the polypeptide is in a plasmid in the host cell.
30. The host cell of any one of paragraphs 18-29, wherein the host cell is *E. coli*.
31. A method of producing a bioconjugate that comprises a polypeptide linked to a saccharide, said method comprising (i) culturing the host cell of any one of paragraphs 18-30 under conditions suitable for the production of proteins and (ii) isolating the bioconjugate.
32. A bioconjugate produced by the method of paragraph 31, wherein said bioconjugate comprises a saccharide linked to a polypeptide, e.g. a polypeptide of any one of paragraphs 1-10.
33. An immunogenic composition comprising the polypeptide of any one of paragraphs 1-10, or the conjugate of any one of paragraphs 11-15, or the bioconjugate of paragraph 32.
34. A method of making the immunogenic composition of paragraph 33 comprising the step of mixing the polypeptide or the conjugate or the bioconjugate with a pharmaceutically acceptable excipient or carrier.
35. A vaccine comprising the immunogenic composition of paragraph 34 and a pharmaceutically acceptable excipient or carrier.
36. A method for the treatment or prevention of *Staphylococcus aureus* infection in a subject in need thereof comprising administering to said subject a therapeutically effective amount of the polypeptide of any one of paragraphs 1-10, or the conjugate of any one of paragraphs 11-15, or the bioconjugate of paragraph 32.
37. A method of immunising a human host against *Staphylococcus aureus* infection comprising administering to the host an immunoprotective dose of the polypeptide of any one of paragraphs 1-10, or the conjugate of any one of paragraphs 11-15, or the bioconjugate of paragraph 32.
38. A method of inducing an immune response to *Staphylococcus aureus* in a subject, the method comprising administering a therapeutically or prophylactically effective amount of the polypeptide of any one of paragraphs 1-10, or the conjugate of any one of paragraphs 11-15, or the bioconjugate of paragraph 32.
39. A polypeptide of any one of paragraphs 1-10, or the conjugate of any one of paragraphs 11-15, or the bioconjugate of paragraph 32, for use in the treatment or prevention of a disease caused by *Staphylococcus aureus* infection.

Description of the Sequence Listing

All sequences are amino acid sequences

```
Wild-type ClfA fibrinogen binding domain (N123) with signal sequence
                                                          SEQ ID NO: 1
MNMKKKEKHAIRKKSIGVASVLVGTLIGFGLLSSKEADASENSVTQSDSASNESKSNDSSSVSAAP

KTDDTNVSDTKTSSNTNNGETSVAQNPAQQETTQSSSTNATTEETPVTGEATTTTTNQANTPATTQ

SSNTNAEELVNQTSNETTFNDTNTVSSVNSPQNSTNAENVSTTQDTSTEATPSNNESAPQSTDASN

KDVVNQAVNTSAPRMRAFSLAAVAADAPAAGTDITNQLTNVTVGIDSGTTVYPHQAGYVKLNYGFS

VPNSAVKGDTFKITVPKELNLNGVTSTAKVPPIMAGDQVLANGVIDSDGNVIYTFTDYVNTKDDVK

ATLTMPAYIDPENVKKTGNVTLATGIGSTTANKTVLVDYEKYGKFYNLSIKGTIDQIDKTNNTYRQ

TIYVNPSGDNVIAPVLTGNLKPNTDSNALIDQQNTSIKVYKVDNAADLSESYFVNPENFEDVTNSV

NITFPNPNQYKVEFNTPDDQITTPYIVVVNGHIDPNSKGDLALRSTLYGYNSNIIWRSMSWDNEVA

FNNGSGSGDGIDKPVVPEQPDEPGEIEPIPED

Wild-type ClfAN1N2N3
                                                          SEQ ID NO: 2
ASENSVTQSDSASNESKSNDSSSVSAAPKTDDTNVSDTKTSSNTNNGETSVAQNPAQQETTQSSST

NATTEETPVTGEATTTTTNQANTPATTQSSNTNAEELVNQTSNETTFNDTNTVSSVNSPQNSTNAE

NVSTTQDTSTEATPSNNESAPQSTDASNKDVVNQAVNTSAPRMRAFSLAAVAADAPAAGTDITNQL

TNVTVGIDSGTTVYPHQAGYVKLNYGFSVPNSAVKGDTFKITVPKELNLNGVTSTAKVPPIMAGDQ

VLANGVIDSDGNVIYTFTDYVNTKDDVKATLTMPAYIDPENVKKTGNVTLATGIGSTTANKTVLVD
```

-continued

YEKYGKFYNLSIKGTIDQIDKTNNTYRQTIYVNPSGDNVIAPVLTGNLKPNTDSNALIDQQNTSIK

VYKVDNAADLSESYFVNPENFEDVTNSVNITFPNPNQYKVEFNTPDDQITTPYIVVVNGHIDPNSK

GDLALRSTLYGYNSNIIWRSMSWDNEVAFNNGSGSGDGIDKPVVPEQPDEPGEIEPIPED

Wild-type ClfAN2N3
SEQ ID NO: 3

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMPAYIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

PGEIEPIPED

ClfAN2N3P116S/Y118A
SEQ ID NO: 4

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

PGEIEPIPED

ClfAN2N3P116S/Y118A with N-terminal S and Flgl signal sequence
SEQ ID NO: 5

MIKFLSALILLLVTTAAQASVAADAPAAGTDITNQLTNVTVGIDSGTTVYPHQAGYVKLNYGFSVP

NSAVKGDTFKITVPKELNLNGVTSTAKVPPIMAGDQVLANGVIDSDGNVIYTFTDYVNTKDDVKAT

LTMSAAIDPENVKKTGNVTLATGIGSTTANKTVLVDYEKYGKFYNLSIKGTIDQIDKTNNTYRQTI

YVNPSGDNVIAPVLTGNLKPNTDSNALIDQQNTSIKVYKVDNAADLSESYFVNPENFEDVTNSVNI

TFPNPNQYKVEFNTPDDQITTPYIVVVNGHIDPNSKGDLALRSTLYGYNSNIIWRSMSWDNEVAFN

NGSGSGDGIDKPVVPEQPDEPGEIEPIPED

ClfAN2N3P116S/Y118A with N-terminal S
SEQ ID NO: 6

SVAADAPAAGTDITNQLTNVTVGIDSGTTVYPHQAGYVKLNYGFSVPNSAVKGDTFKITVPKELNL

NGVTSTAKVPPIMAGDQVLANGVIDSDGNVIYTFTDYVNTKDDVKATLTMSAAIDPENVKKTGNVT

LATGIGSTTANKTVLVDYEKYGKFYNLSIKGTIDQIDKTNNTYRQTIYVNPSGDNVIAPVLTGNLK

PNTDSNALIDQQNTSIKVYKVDNAADLSESYFVNPENFEDVTNSVNITFPNPNQYKVEFNTPDDQI

TTPYIVVVNGHIDPNSKGDLALRSTLYGYNSNIIWRSMSWDNEVAFNNGSGSGDGIDKPVVPEQPD

EPGEIEPIPED

Wild-type ClfAN1N2N3 with glycosite at position corresponding to
mutant 30 (I557 of full-length ClfA, underlined)
SEQ ID NO: 7

ASENSVTQSDSASNESKSNDSSSVSAAPKTDDTNVSDTKTSSNTNNGETSVAQNPAQQETTQSSST

NATTEETPVTGEATTTTTNQANTPATTQSSNTNAEELVNQTSNETTFNDTNTVSSVNSPQNSTNAE

NVSTTQDTSTEATPSNNESAPQSTDASNKDVVNQAVNTSAPRMRAFSLAAVAADAPAAGTDITNQL

TNVTVGIDSGTTVYPHQAGYVKLNYGFSVPNSAVKGDTFKITVPKELNLNGVTSTAKVPPIMAGDQ

VLANGVIDSDGNVIYTFTDYVNTKDDVKATLTMPAYIDPENVKKTGNVTLATGIGSTTANKTVLVD

YEKYGKFYNLSIKGTIDQIDKTNNTYRQTIYVNPSGDNVIAPVLTGNLKPNTDSNALIDQQNTSIK

VYKVDNAADLSESYFVNPENFEDVTNSVNITFPNPNQYKVEFNTPDDQITTPYIVVVNGHIDPNSK

GDLALRSTLYGYNSNIIWRSMSWDNEVAFNNGSGSGDGIDKPVVPEQPDEPGEIEPKDQNATKPED

-continued

ClfAN1N2N3 P298S/Y300A with glycosite at position corresponding to mutant 30 (I557 of full-length ClfA, underlined)
SEQ ID NO: 8

ASENSVTQSDSASNESKSNDSSSVSAAPKTDDTNVSDTKTSSNTNNGETSVAQNPAQQETTQSSST

NATTEETPVTGEATTTTTNQANTPATTQSSNTNAEELVNQTSNETTFNDTNTVSSVNSPQNSTNAE

NVSTTQDTSTEATPSNNESAPQSTDASNKDVVNQAVNTSAPRMRAFSLAAVAADAPAAGTDITNQL

TNVTVGIDSGTTVYPHQAGYVKLNYGFSVPNSAVKGDTFKITVPKELNLNGVTSTAKVPPIMAGDQ

VLANGVIDSDGNVIYTFTDYVNTKDDVKATLTMSAAIDPENVKKTGNVTLATGIGSTTANKTVLVD

YEKYGKFYNLSIKGTIDQIDKTNNTYRQTIYVNPSGDNVIAPVLTGNLKPNTDSNALIDQQNTSIK

VYKVDNAADLSESYFVNPENFEDVTNSVNITFPNPNQYKVEFNTPDDQITTPYIVVVNGHIDPNSK

GDLALRSTLYGYNSNIIWRSMSWDNEVAFNNGSGSGDGIDKPVVPEQPDEPGEIEPKDQNATKPED

Wild-type ClfAN2N3 with mutant 30 glycosite (underlined)
SEQ ID NO: 9

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMPAYIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

PGEIEPKDQNATKPED

ClfAN2N3P116S/Y118A with mutant 30 glycosite (underlined)
SEQ ID NO: 10

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

PGEIEPKDQNATKPED

ClfAN2N3P116S/Y118A with N-terminal S and Flgl signal sequence and mutant 30 glycosite (underlined)
SEQ ID NO: 11

MIKFLSALILLLVTTAAQASVAADAPAAGTDITNQLTNVTVGIDSGTTVYPHQAGYVKLNYGFSVP

NSAVKGDTFKITVPKELNLNGVTSTAKVPPIMAGDQVLANGVIDSDGNVIYTFTDYVNTKDDVKAT

LTMSAAIDPENVKKTGNVTLATGIGSTTANKTVLVDYEKYGKFYNLSIKGTIDQIDKTNNTYRQTI

YVNPSGDNVIAPVLTGNLKPNTDSNALIDQQNTSIKVYKVDNAADLSESYFVNPENFEDVTNSVNI

TFPNPNQYKVEFNTPDDQITTPYIVVVNGHIDPNSKGDLALRSTLYGYNSNIIWRSMSWDNEVAFN

NGSGSGDGIDKPVVPEQPDEPGEIEPKDQNATKPED

ClfAN2N3P116S/Y118A with N-terminal S and mutant 30 glycosite (underlined)
SEQ ID NO: 12

SVAADAPAAGTDITNQLTNVTVGIDSGTTVYPHQAGYVKLNYGFSVPNSAVKGDTFKITVPKELNL

NGVTSTAKVPPIMAGDQVLANGVIDSDGNVIYTFTDYVNTKDDVKATLTMSAAIDPENVKKTGNVT

LATGIGSTTANKTVLVDYEKYGKFYNLSIKGTIDQIDKTNNTYRQTIYVNPSGDNVIAPVLTGNLK

PNTDSNALIDQQNTSIKVYKVDNAADLSESYFVNPENFEDVTNSVNITFPNPNQYKVEFNTPDDQI

TTPYIVVVNGHIDPNSKGDLALRSTLYGYNSNIIWRSMSWDNEVAFNNGSGSGDGIDKPVVPEQPD

EPGEIEPKDQNATKPED

-continued

FlgI signal sequence
SEQ ID NO: 13
MIKFLSALILLLVTTAAQA

OmpA signal sequence
SEQ ID NO: 14
MKKTAIAIAVALAGFATVAQA

MalE signal sequence
SEQ ID NO: 15
MKIKTGARILALSALTTMMFSASALA

PelB signal sequence
SEQ ID NO: 16
MKYLLPTAAAGLLLLAAQPAMA

LTIIb signal sequence
SEQ ID NO: 17
MSFKKIIKAFVIMAALVSVQAHA

DsbA signal sequence
SEQ ID NO: 18
MKKIWLALAGLVLAFSASA

TolB signal sequence
SEQ ID NO: 19
MKQALRVAFGFLILWASVLHA

SipA signal sequence
SEQ ID NO: 20
MKMNKKVLLTSTMAASLLSVASVQAS glycosite
SEQ ID NO: 21
D/E-X-N-Z-S/T glycosite
SEQ ID NO: 22
K-D/E-X-N-Z-S/T-K glycosite
SEQ ID NO: 23
K-D-Q-N-A-T-K glycosite
SEQ ID NO: 24
K-D-Q-N-R-T-K ClfAN2N3P116S/Y118A with mutant 30 glycosite (underlined),
additional GSand 6-His C-terminal tag
SEQ ID NO: 25
VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

PGEIEPKDQNATKPEDGSHHHHHH

ClfAN2N3P116S/Y118A with N-terminal Sand FlgI signal sequence and
mutant 30 glycosite (underlined), additional GSand 6-His C-terminal
tag
SEQ ID NO: 26
MIKFLSALILLLVTTAAQASVAADAPAAGTDITNQLTNVTVGIDSGTTVYPHQAGYVKLNYGFSVP

NSAVKGDTFKITVPKELNLNGVTSTAKVPPIMAGDQVLANGVIDSDGNVIYTFTDYVNTKDDVKAT

LTMSAAIDPENVKKTGNVTLATGIGSTTANKTVLVDYEKYGKFYNLSIKGTIDQIDKTNNTYRQTI

YVNPSGDNVIAPVLTGNLKPNTDSNALIDQQNTSIKVYKVDNAADLSESYFVNPENFEDVTNSVNI

TFPNPNQYKVEFNTPDDQITTPYIVVVNGHIDPNSKGDLALRSTLYGYNSNIIWRSMSWDNEVAFN

NGSGSGDGIDKPVVPEQPDEPGEIEPKDQNATKPEDGSHHHHHH

-continued

ClfAN2N3P116S/Y118A with N-terminal S, glycosite (underlined),
additional GS and 6-His C-terminal tag

SEQ ID NO: 27

SVAADAPAAGTDITNQLTNVTVGIDSGTTVYPHQAGYVKLNYGFSVPNSAVKGDTFKITVPKELNL

NGVTSTAKVPPIMAGDQVLANGVIDSDGNVIYTFTDYVNTKDDVKATLTMSAAIDPENVKKTGNVT

LATGIGSTTANKTVLVDYEKYGKFYNLSIKGTIDQIDKTNNTYRQTIYVNPSGDNVIAPVLTGNLK

PNTDSNALIDQQNTSIKVYKVDNAADLSESYFVNPENFEDVTNSVNITFPNPNQYKVEFNTPDDQI

TTPYIVVVNGHIDPNSKGDLALRSTLYGYNSNIIWRSMSWDNEVAFNNGSGSGDGIDKPVVPEQPD

EPGEIEPKDQNATKPEDGSHHHHHH

ClfAN2N3P116S/Y118A mutant 1 (D24KDQNATK)

SEQ ID NO: 28

VAADAPAAGTDITNQLTNVTVGIKDQNATKSGTTVYPHQAGYVKLNYGFSVPNSAVKGDTFKITVP

KELNLNGVTSTAKVPPIMAGDQVLANGVIDSDGNVIYTFTDYVNTKDDVKATLTMSAAIDPENVKK

TGNVTLATGIGSTTANKTVLVDYEKYGKFYNLSIKGTIDQIDKTNNTYRQTIYVNPSGDNVIAPVL

TGNLKPNTDSNALIDQQNTSIKVYKVDNAADLSESYFVNPENFEDVTNSVNITFPNPNQYKVEFNT

PDDQITTPYIVVVNGHIDPNSKGDLALRSTLYGYNSNIIWRSMSWDNEVAFNNGSGSGDGIDKPVV

PEQPDEPGEIEPIPED

ClfAN2N3P116S/Y118A mutant 27 Q327KDQNATK)

SEQ ID NO: 29

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEKDQN

ATKPDEPGEIEPIPED

ClfAN2N3P116S/Y118A mutant 28 (D329KDQNATK)

SEQ ID NO: 30

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPKD

QNATKEPGEIEPIPED

ClfAN2N3P116S/Y118A mutant 29 (P331KDQNATK)

SEQ ID NO: 31

VAADAPAAGTDITNQLTNVTVGIDSGTTVYPHQAGYVKLNYGFSVPNSAVKGDTFKITVPKELNLN

GVTSTAKVPPIMAGDQVLANGVIDSDGNVIYTFTDYVNTKDDVKATLTMSAAIDPENVKKTGNVTL

ATGIGSTTANKTVLVDYEKYGKFYNLSIKGTIDQIDKTNNTYRQTIYVNPSGDNVIAPVLTGNLKP

NTDSNALIDQQNTSIKVYKVDNAADLSESYFVNPENFEDVTNSVNITFPNPNQYKVEFNTPDDQIT

TPYIVVVNGHIDPNSKGDLALRSTLYGYNSNIIWRSMSWDNEVAFNNGSGSGDGIDKPVVPEQPDE

KDQNATKGEIEPIPED

ClfAN2N3P116S/Y118A with mutant 30 glycosite (underlined), N-
terminal S, C-terminal GS

SEQ ID NO: 32

SVAADAPAAGTDITNQLTNVTVGIDSGTTVYPHQAGYVKLNYGFSVPNSAVKGDTFKITVPKELNL

NGVTSTAKVPPIMAGDQVLANGVIDSDGNVIYTFTDYVNTKDDVKATLTMSAAIDPENVKKTGNVT

LATGIGSTTANKTVLVDYEKYGKFYNLSIKGTIDQIDKTNNTYRQTIYVNPSGDNVIAPVLTGNLK

-continued
PNTDSNALIDQQNTSIKVYKVDNAADLSESYFVNPENFEDVTNSVNITFPNPNQYKVEFNTPDDQI

TTPYIVVVNGHIDPNSKGDLALRSTLYGYNSNIIWRSMSWDNEVAFNNGSGSGDGIDKPVVPEQPD

EPGEIEPKDQNATKPEDGS

In order that this invention may be better understood, the following examples are set forth. These examples are for purposes of illustration only, and are not to be construed as limiting the scope of the invention in any manner.

EXAMPLES

Example 1: Screen of ClfA Glycosite Mutants

Chemical competent cells of *E. coli* strain StGVXN1690, clone 6D (W3110 ΔwaaL; ΔECA(rffG-rffM)::cat) carrying the plasmid encoding the *Staphylococcus aureus* capsular polysaccharide CP8 (CPS 8; pGVXN564) and the plasmid encoding the codon usage optimized version of the *Campylobacter jejuni* oligosaccharyl transferase PglB N534Q mutant (pGVXN971) were transformed with plasmids encoding the indicated (see table) *Staphylococcus aureus* clumping factor N2N3 glyco-site mutants with an *E. coli* OmpA signal sequence and carrying a C-terminal hexahistidine affinity tag (SEQ ID NO: 36):

TABLE 1

Using pGVXN974, site-directed mutagenesis was employed to replace the indicated amino acid residue in ClfA against a glycosylation site (glycosylation sequence "KDQNATK" SEQ ID NO: 23)) resulting in the pEC415-based expression plasmids displaying ampicillin resistance. For ease of reference, the corresponding numbering in ClfN2N3 is also given.

| plasmid | Mutation - ClfA full-length numbering ("KDQNATK" disclosed as SEQ ID NO: 23) | Mutation - ClfA N2N3 numbering ("KDQNATK" disclosed as SEQ ID NO: 23) | plasmid backbone, antibiotic resistance |
|---|---|---|---|
| pGVXN1141 | mut 1: D244KDQNATK | D24KDQNATK | pEC414, Ampicillin resistance |
| pGVXN1142 | mut 2: T248KDQNATK | T28KDQNATK | pEC414, Ampicillin resistance |
| pGVXN1143 | mut 3: G262KDQNATK | G42KDQNATK | pEC414, Ampicillin resistance |
| pGVXN1144 | mut 4: T278KDQNATK | T58KDQNATK | pEC414, Ampicillin resistance |
| pGVXN1145 | mut 5: G300KDQNATK | G80KDQNATK | pEC414, Ampicillin resistance |
| pGVXN1146 | mut 6: V308KDQNATK | V88KDQNATK | pEC414, Ampicillin resistance |
| pGVXN1147 | mut 7: D312KDQNATK | D92KDQNATK | pEC414, Ampicillin resistance |
| pGVXN1148 | mut 8: I316KDQNATK | I96KDQNATK | pEC414, Ampicillin resistance |
| pGVXN1149 | mut 9: T318KDQNATK | T98KDQNATK | pEC414, Ampicillin resistance |
| pGVXN1150 | mut 10: K330KDQNATK | K110KDQNATK | pEC414, Ampicillin resistance |
| pGVXN1151 | mut 11: N349KDQNATK | N129KDQNATK | pEC414, Ampicillin resistance |
| pGVXN1152 | mut 12: L366KDQNATK | L146KDQNATK | pEC414, Ampicillin resistance |
| pGVXN1153 | mut 13: Y376KDQNATK | Y156KDQNATK | pEC414, Ampicillin resistance |
| pGVXN1154 | mut 14: T390KDQNATK | T170KDQNATK | pEC414, Ampicillin resistance |
| pGVXN1155 | mut 15: N406KDQNATK | N186KDQNATK | pEC414, Ampicillin resistance |

TABLE 1-continued

Using pGVXN974, site-directed mutagenesis was employed to replace the indicated amino acid residue in ClfA against a glycosylation site (glycosylation sequence "KDQNATK" SEQ ID NO: 23)) resulting in the pEC415-based expression plasmids displaying ampicillin resistance. For ease of reference, the corresponding numbering in ClfN2N3 is also given.

| plasmid | Mutation - ClfA full-length numbering ("KDQNATK" disclosed as SEQ ID NO: 23) | Mutation - ClfA N2N3 numbering ("KDQNATK" disclosed as SEQ ID NO: 23) | plasmid backbone, antibiotic resistance |
|---|---|---|---|
| pGVXN1156 mut 16: | P418KDQNATK | P198KDQNATK | pEC414, Ampicillin resistance |
| pGVXN1158 mut 18: | S432KDQNATK | S212KDQNATK | pEC414, Ampicillin resistance |
| pGVXN1159 mut 19: | F466KDQNATK | F246KDQNATK | pEC414, Ampicillin resistance |
| pGVXN1160 mut 20: | D480KDQNATK | D260KDQNATK | pEC414, Ampicillin resistance |
| pGVXN1161 mut 21: | Q482KDQNATK | Q262KDQNATK | pEC414, Ampicillin resistance |
| pGVXN1162 mut 22: | H494KDQNATK | H274KDQNATK | pEC414, Ampicillin resistance |
| pGVXN1163 mut 23: | G501KDQNATK | G281KDQNATK | pEC414, Ampicillin resistance |
| pGVXN1164 mut 24: | N515KDQNATK | N295KDQNATK | pEC414, Ampicillin resistance |
| pGVXN1166 mut 26: | R519KDQNATK | R299KDQNATK | pEC414, Ampicillin resistance |
| pGVXN1167 mut 27: | Q547KDQNATK | Q327KDQNATK | pEC414, Ampicillin resistance |
| pGVXN1168 mut 28: | D549KDQNATK | D329KDQNATK | pEC414, Ampicillin resistance |
| pGVXN1169 mut 29: | P551KDQNATK | P331KDQNATK | pEC414, Ampicillin resistance |
| pGVXN1170 mut 30: | I557KDQNATK | I337KDQNATK | pEC414, Ampicillin resistance |

As one positive control chemical competent cells of *E. coli* strain StGVXN1690, clone 6D (W3110 ΔwaaL; ΔECA (rffG-rffM)::cat) carrying the plasmid encoding the *Staphylococcus aureus* capsular polysaccharide CP8 (CPS 8; pGVXN564) and the plasmid encoding the codon usage optimized version of the *Campylobacter jejuni* oligosaccharyltransferase PglB N534Q mutant (pGVXN971) were transformed with a plasmid (pGVXN150) encoding *Pseudomonas aeruginosa* exoprotein A (pEC415-DsbA-ss-EPA$^{2xglycosites}_{His6}$) with an *E. coli* DsbA signal sequence and carrying a C-terminal hexahistidine affinity tag (SEQ ID NO: 36). As second positive control chemical competent cells of *E. coli* strain StGVXN1690, clone 6D (W3110 ΔwaaL; ΔECA(rffG-rffM)::cat) carrying the plasmid encoding the *Staphylococcus aureus* capsular polysaccharide CP8 (CPS 8; pGVXN564) and the plasmid encoding the codon usage optimized version of the *Campylobacter jejuni* oligosaccharyltransferase PglB N534Q mutant (pGVXN971) were transformed with a plasmid (pGVXN633) encoding *Staphylococcus aureus* clumping factor glyco-site mutant (D328KDQNRTK (SEQ ID NO: 24)) with an *E. coli* DsbA signal sequence and carrying a C-terminal hexahistidine affinity tag (SEQ ID NO: 36).

Figure 3B:
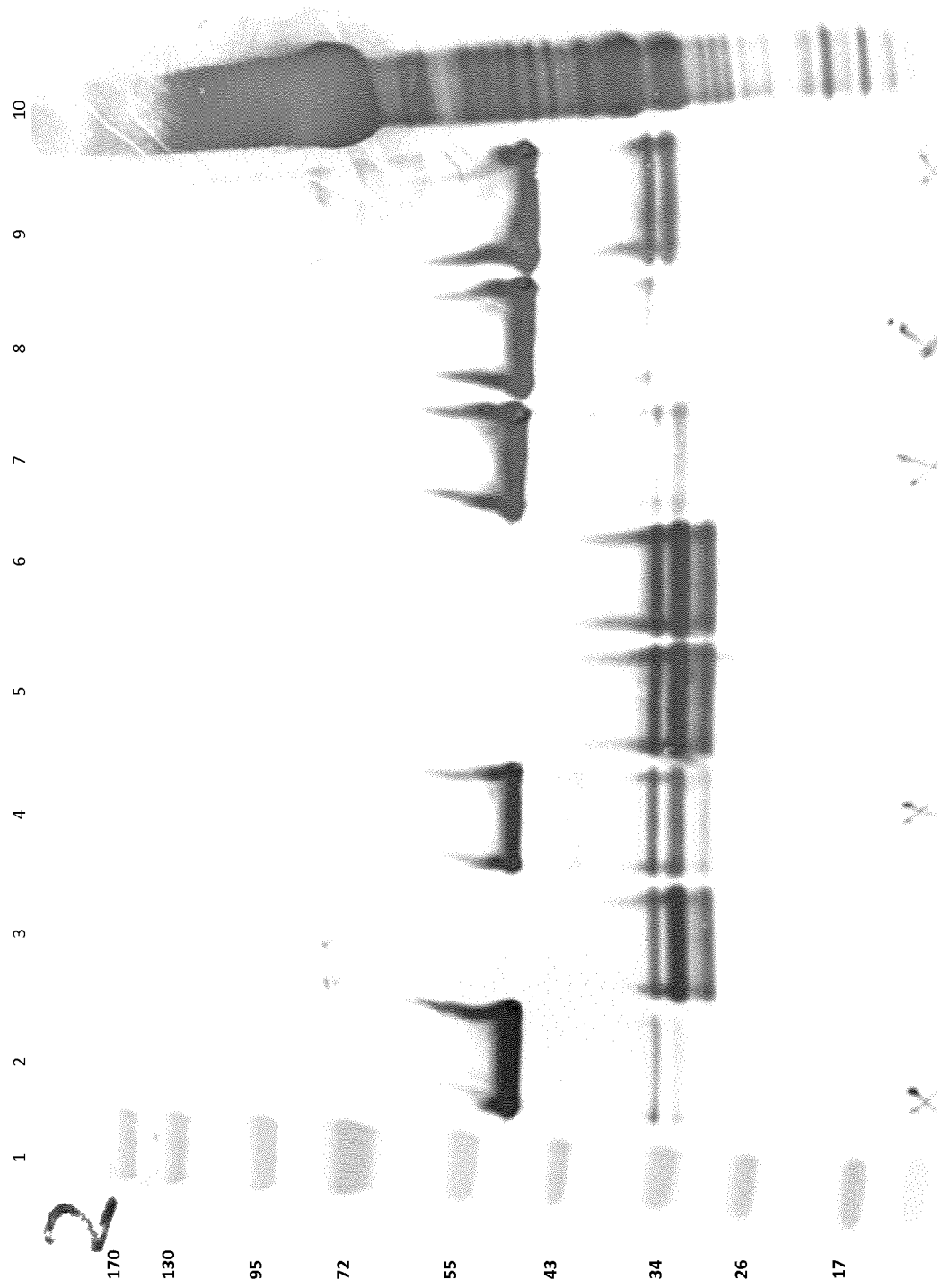
FIGS. 3, 4: Anti-His Western blot of different ClfA glycosite mutant bioconjugates Anti-His Western blot analysis of CP8-ClfAN2N3 bioconjugate production for mutants 1-30 as described in Example 1, with D328KDQNRTK (SEQ ID NO: 24) (plasmid 633) as positive control and EPA-CP8. Lane 1: Protein markers (M). Blot: rabbit α-His 1:2000, goat α-mouse 1:20 000.
Figure 4B:
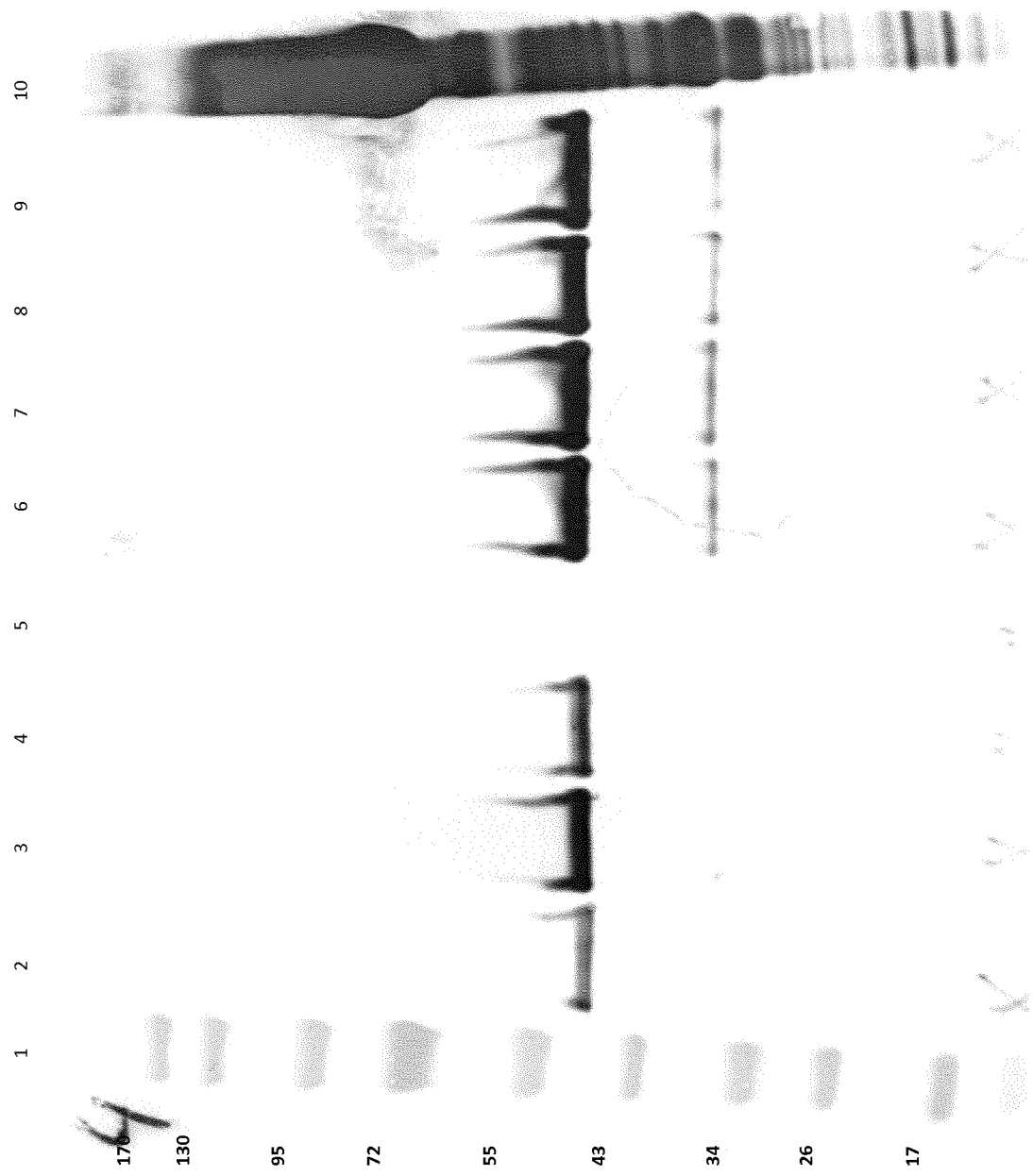

As a negative control chemical competent cells of *E. coli* strain StGVXN1690, clone 6D (W3110 ΔwaaL; ΔECA (rffG-rffM)::cat) carrying the plasmid encoding the *Staphylococcus aureus* capsular polysaccharide CP8 (CPS 8; pGVXN564) and the plasmid encoding the codon usage optimized version of the *Campylobacter jejuni* oligosaccharyltransferase PglB N534Q mutant (pGVXN971) were transformed with a plasmid (pGVXN974) encoding *Staphylococcus aureus* clumping factor without a glycosite containing an *E. coli* OmpA signal sequence and carrying a C-terminal hexahistidine affinity tag (SEQ ID NO: 36). Cells were grown overnight on selective Luria Broth (LB) agar plates supplemented with the three antibiotics ampicillin [100 ug/ml], tetracycline [100 ug/ml] and spectinomycine [40 ug/ml]. Freshly grown transformants were inoculated into 1 ml LB preculture supplemented with the antibiotics ampicilline [100 ug/ml], tetracycline [100 ug/ml] and spectinomycine [40 ug/ml] and shaken in a 96-deepwell plate overnight at 37° C. After overnight cultivation 100 ul of the precultures were used to inoculate 900 ul Terrific Broth (TB)

supplemented with 10 mM MgCl$_2$ and with the antibiotics ampicilline [100 ug/ml], tetracycline [100 ug/ml] and spectinomycine [40 ug/ml]. After 150 min cultivation at 37° C. cultures were induced with 1 mM IPTG and 0.1% arabinose and cultivated o/n at 37° C. Cells were harvested within the 96-deepwell plates by centrifugation for 10 min. at 3700 rpm. The periplasmic content was extracted with 200 ul lysis buffer (30 mM Tris-HCl pH 8.5, 1 mM EDTA pH 8.0, 20% sucrose, containing lysozyme [final 1 mg/ml]), during 30 minutes at 4° C. Periplasmic extracts (PPE) were cleared by centrifugation (15 min. at 3700 rpm) and 150 ul of each supernatant were mixed with 37.5 ul 5× binding buffer (150 mM Tris-HCl pH 8.0, 2.5 M NaCl, 50 mM imidazole pH 8.0, 4 mM MgCl2) in a new 96 well plate (=load). The "loads" were transferred to a new 96-well plate containing 50 ul/well Ni-NTA agarose that was equilibrated before with 1× binding buffer (30 mM Tris-HCl pH 80, 500 mM NaCl, 10 mM imidazole pH 8.0) and incubated for 1 hr at ambient temperature. The slurries were transferred to a new 96 well plate (containing one filter device/well). Ni-NTA agarose with bound protein was centrifuged onto the filter during 2 min. at 300 rcf and the flowthrough was discarded. Filters were washed twice with 1× binding buffer and bound protein was eluted with 50 ul elution buffer per filter (1×PBS pH 7.0; 500 mM Imidazole). 20 ul 4× Lammli sample buffer were added to each of the eluted samples, mixed and boiled for 10 min. at 95° C. For analysis by Western Blot 30 ul of these samples were loaded per lane onto a 4-12% NuPAGE Gel, proteins were electro blotted on nitrocellulose membrane and detected with an anti-His antibody (Qiagen No 34660; FIGS. 3 and 4) and a secondary anti-mouse peroxidase conjugate antibody (Sigma, A0412) or a anti-CP8 antibody and a secondary anti-rabbit peroxidase conjugate antibody (BioRad, 170-6515; FIGS. 5 and 6). The anti-CP8 Western Blot revealed conjugate formation for *Staphylococcus aureus* clumping factor glyco-site mutants mut1, mut27, mut28, and mut30.

Example 2: Improved Protein Stability of *S. aureus* Bioconjugate Production in the Context of Carrier Protein ClfAN2N3 Glyco-Site Mutant 30 Compared to Glyco-Site Mutant 1

Glycosylation efficiency and stability of mutants 1 and 30 described in Example 1 were compared directly.

Strain StGVXN8966 (W3110 waaL::pglB$_{CUO\ N311V-}$ $_{K482R-D483H-A669V}$; O16::O11_wbjB-wbpM; ΔrmlB-wecG; wecA-wzzE::CP8_p2636(CCW)_Cat) was individually transformed with the plasmids encoding the *Staphylococcus aureus* clumping factor domains N2N3 glyco-site mutant mut 1 (ClfAN2N3, pGVXN1188) or the plasmid encoding clumping factor domains N2N3 glyco-site mutant mut 30 (pGVXN2592) by electroporation.

Cells were grown in TB medium, *S. aureus* capsular polysaccharide CP8 (CPS 8) was expressed constitutively from gene clusters integrated into the *E. coli* genome. Integrated oligosaccharyltransferase PglB was induced with 1 mM isopropyl-p-D-thiogalactopyranoside (IPTG), plasmid-borne ClfAN2N3 were induced with 0.6% arabinose, at an optical density OD$_{600\ nm}$ of 0.95 and 1.05.

After overnight induction at 37° C., cells were harvested and the CP8-ClfAN2N3 bioconjugates were extracted by a periplasmic preparation using a lysis buffer (30 mM Tris-HCl pH 8.5, 1 mM EDTA, 20% (w/v) sucrose) supplemented with 1 mg/ml lysozyme. Periplasmic proteins were collected from the supernatant after centrifugation, loaded on a 4-12% SDS-PAGE and blotted onto a nitrocellulose membrane and detected with an anti-Histidine tag antibody. Proteins loaded were normalized for the optical density of the cells. Results are shown in FIG. 9.

Example 3: Expression and Purification of CP8-ClfAN2N3 Mutant 1 Bioconjugate from a Three Plasmid System FIG. 7 shows a SDS-PAGE SIMPLYBLUE™ SafeStain, an anti-ClfA and an anti-CP8 Western Blot analysis of the final product of CP8-ClfAN2N3 mut1, expressed from a three plasmid system in a 20 L bioreactor and purified to homogeneity.

Strain StGVXN1690, clone 6D (W3110 ΔwaaL; ΔECA (rffG-rffM)::cat) carrying the plasmids encoding the *Staphylococcus aureus* clumping factor domains N2N3 glyco-site mutant mut1 with an *E. coli* OmpA signal sequence and carrying a C-terminal hexahistidine affinity tag pGVXN1188 and the plasmid encoding the *Staphylococcus aureus* capsular polysaccharide CP8 (CPS 8) pGVXN564 was transformed with the plasmid carrying the *Campylobacter jejuni* oligosaccharyltransferase PglB wild type codon usage optimized pGVXN970, by electroporation and plated on a selective agar plate.

Cells were inoculated into a 400 ml LB preculture, shaken overnight at 37° C. and inoculated into a 20 L Bioreactor (newMBR FE_03/20 L) containing 7 Liter (L) Terrific Broth (TB) medium. Recombinant polysaccharide was expressed constitutively, while PglB and ClfAN2N3 mut1 were induced with 1 mM isopropyl-p-D-thiogalactopyranoside (IPTG) and with 0.6% arabinose, respectively, at an optical density OD$_{600\ nm}$ of 40, and the vessel was fed with TB medium overnight at 37° C. until an OD$_{600\ nm}$ of 108 and 10 L total volume was reached and the induction was continued for a total of 40 hours (h).

After induction, a total of 803,600 ODs were harvested and washed with 0.9% sodium chloride. CP8-ClfAN2N3 mut1 bioconjugates from 100,000 ODs were extracted by an osmotic shock treatment. Cells were resuspended in 250 ml ⅓×TBS (Tris buffered saline, Fisher Scientific), supplemented with 125 ml resuspension buffer (75% Sucrose, 30 mM EDTA, 600 mM Tris HCl pH 8.5) incubated for 20 minutes at 4° C. by rotation. Cells were pelleted and resuspended in 375 ml osmotic shock buffer (10 mM Tris HCl pH 8.0) and again incubated for 30 minutes at 4° C. Cells were pelleted and the supernatant (420 ml) was supplemented with 21 ml 1 M magnesium chloride and 110 ml 5× binding buffer 150 mM Tris-HCl, pH 8.0, 2500 mM NaCl, 25 mM Imidazole and filtered with a 0.2 micrometer filter. 40 ml of IMAC (Immobilized metal affinity chromatography) beads were equilibrated with 30 mM Tris-HCl, pH 8.0, 500 mM NaCl, 5 mM Imidazole and incubated with the sample by stirring for 30 minutes at room temperature. The resin was packed into a XK26/20 column (GE Healthcare) and washed with 30 mM Tris-HCl, pH 8.0, 500 mM NaCl, 5 mM Imidazole for 2 column volumes. The protein was eluted with a gradient to reach 30 mM Tris-HCl, pH 8.0, 500 mM NaCl, 500 mM Imidazole in 15 column volumes. Fractions were analyzed by 4-12% SDS-PAGE, developed with anti-His Western Blot and all fractions containing bioconjugate were pooled (110 ml) and directly loaded on a PallQ column (Pall) equilibrated with 30 mM Bis-Tris pH 6.5, 50 mM NaCl. The protein was eluted by a gradient of 20 column volumes to 30 mM Bis-Tris pH 6.5, 500 mM NaCl and fractions were analyzed by 4-12% SDS-PAGE, stained with SIMPLYBLUE™ Safe Stain and visualized by anti-His Western Blot. Fractions containing most of the bioconjugate and least of the unglycosylated species were pooled (42 ml) and dialyzed against 4 L of 5 mM Na-Phosphate pH 7.2, 150 mM NaCl overnight at 4° C. The sample was loaded on a Hydroxyapatite column (Biorad) equilibrated with 5 mM Na-Phosphate pH 7.2, 150 mM NaCl and eluted by a differential gradient up to 500 mM Na-Phosphate pH 7.2, 150 mM NaCl. Fractions were analyzed by 4-12% SDS-PAGE, stained with SIMPLYBLUE™ Safe Stain and fractions containing longer glycans were pooled The pooled sample (55 ml) was concentrated in a 10 kDa molecular weight cutoff (MWCO) filter (Millipore) and injected into a size exclusion column (SUPERDEX© 200 10/300, GE Healthcare) equilibrated and running in 1×TBS (Tris buffered saline, Fisher Scientific). Fractions were analyzed by 4-12% SDS-PAGE, stained with SIMPLYBLUE™ Safe Stain and cleanest fractions containing the least unglycosylated protein and impurities were pooled and sterile filtered.

Example 4: Expression and Purification of CP8-ClfAN2N3 Mut 30 Bioconjugate from a One Plasmid System FIG. 8 shows a SDS-PAGE SIMPLYBLUE™ SafeStain, an anti-ClfA and an anti-CP8 Western Blot analysis of the final product of CP8-ClfAN2N3 mut30, expressed from a one-plasmid system in a 2 L bioreactor and purified to homogeneity.

Strain StGVXN8966 (W3110 waaL::pglB$_{CUO\ N311V\text{-}K482R\text{-}D483H\text{-}A669V}$; O16::O11_wbjB-wbpM; ΔrmlB-wecG; wecA-wzzE::CP8_p2636(CCW)_Cat) was transformed with the plasmid encoding the *Staphylococcus aureus* clumping factor domains N2N3 glyco-site mutant mut 30 with a *S. flexneri* flagellar P-ring protein signal sequence (FlgI) and carrying a C-terminal hexahistidine affinity tag (pGVXN2685), by electroporation and plated on a selective agar plate.

Cells were inoculated into a 400 ml LB preculture supplemented with 10 mM MgCl2, shaken overnight at 37° C. and inoculated into a 2 L Bioreactors (Infors Multitron) containing 1.4 L TB medium. Recombinant polysaccharide was expressed constitutively, while PglB and ClfA were induced with 1 mM isopropyl-p-D-thiogalactopyranoside (IPTG) and with 0.6% arabinose, respectively, at an optical density OD$_{600\ nm}$ of 33, and the vessel was fed with TB medium overnight to reach 1.8 liter total volume.

After overnight induction, a total of 138,600 ODs were harvested and washed with 0.9% sodium chloride. Bioconjugates were extracted by an osmotic shock treatment. Cells (30,000 OD$_{600}$ equivalents) were resuspended in 100 ml ⅓×TBS (Tris buffered saline, Fisher Scientific). supplemented with 50 ml resuspension buffer (75% Sucrose, 30 mM EDTA, 600 mM Tris HCl pH 8.5) incubated for 30 minutes at 4° C. by rotation. Cells were pelleted and resuspended in 150 ml osmotic shock buffer (10 mM Tris HCl pH 8.0) and again incubated for 30 minutes at 4° C. Cells were pelleted and the supernatant was supplemented with 50 mM MgCl2 and 5× binding buffer to reach 30 mM Tris-HCl, pH 8.0, 500 mM NaCl, 5 mM Imidazole. 50 ml of IMAC (Immobilized metal affinity chromatography) beads were equilibrated with 30 mM Tris-HCl, pH 8.0, 500 mM NaCl, 5 mM Imidazole and incubated with the sample by stirring for 1 h at room temperature. The resin was packed into a XK26 column (GE Healthcare) and washed with 30 mM Tris-HCl, pH 8.0, 500 mM NaCl, 5 mM Imidazole for 5 column volumes. The protein was eluted with a gradient to reach 30 mM Tris-HCl, pH 8.0, 500 mM NaCl, 500 mM Imidazole in 15 column volumes. Fractions were analyzed by 4-12% SDS-PAGE, developed with anti-His Western Blot and all fractions containing bioconjugate were pooled (128 ml), and directly loaded on a PallQ column (Pall) equilibrated with 30 mM Bis-Tris pH 6.5, 50 mM NaCl. The protein was eluted by a gradient of 20 column volumes to 30 mM Bis-Tris pH 6.5, 500 mM NaCl and fractions were analyzed by 4-12% SDS-PAGE, stained with SIMPLYBLUE™ Safe Stain and visualized by anti-His Western Blot. Fractions containing most of the bioconjugate and least of the unglycosylated species were pooled (55 ml) and dialyzed against 4 L of 5 mM Na-Phosphate pH 7.2, 150 mM NaCl overnight at 4° C. The sample was loaded on a Hydroxyapatite column (Biorad) equilibrated with 5 mM Na-Phosphate pH 7.2, 150 mM NaCl and eluted by a differential gradient up to 500 mM Na-Phosphate pH 7.2, 150 mM NaCl. Fractions were analyzed by 4-12% SDS-PAGE, stained with SIMPLYBLUE™ Safe Stain and fractions containing longer glycans were pooled separately from fractions containing shorter glycans. The pooled samples were concentrated separately in a 10 kDa MWCO filter (Millipore) and injected into a size exclusion column (SUPERDEX© 200 10/300, GE Healthcare) running in 1×TBS (Tris buffered saline, Fisher Scientific). Fractions were analyzed by 4-12% SDS-PAGE, stained with SIMPLYBLUE™ Safe Stain and cleanest fractions containing the least unglycosylated protein were pooled and sterile filtered.

Example 5: Enhanced *S. aureus* CP8-ClfAN2N3 Mut30 Bioconjugate Productivity with Carrier Expression from a Flagellin Signal Sequence Versus an OmpA Signal Sequence FIG. 10 shows the impact on production yields with different signal sequences on ClfAN2N3 mut30 and highlights the enhancement of CP8-ClfAN2N3 mut 30 bioconjugate productivity with signal sequence from *S. flexneri* flagellar P-ring protein FlgI.

Strain StGVXN8966 (W3110 waaL::pglB$_{CUO\ N311V\text{-}K482R\text{-}D483H\text{-}A669V}$; O16::O11_wbjB-wbpM; ΔrmlB-wecG; wecA-wzzE::CP8_p2636(CCW)_Cat) was individually transformed with the plasmids encoding the *Staphylococcus aureus* clumping factor domains N2N3 glyco-site mutant mut 30 with an *E. coli* disulfide oxidoreductase DsbA signal sequence (DsbA, pGVXN2684), a *S. flexneri* flagellar P-ring protein signal sequence (FlgI, pGVXN2685), *E. coli* heat-labile enterotoxin IIB, B chain signal sequence (LTIIb, pGVXN2686), *E. coli* maltose binding protein MalE signal sequence (MalE, pGVXN2687), *P. carotovorum* pectase lyase 2 precursor signal sequence (PelB, pGVXN2688), *S. agalactiae* surface immunogenic protein signal sequence (SipA, pGVXN2689), *E. coli* translocation protein signal sequence (TolB, pGVXN2691), *E. coli* outer membrane protein signal sequence (OmpA, pGVXN2692) by electroporation.

Cells were grown in TB medium, *S. aureus* capsular polysaccharide CP8 (CPS 8) was expressed constitutively from gene clusters integrated into the *E. coli* genome. Integrated oligosaccharyltransferase PglB was induced with 1 mM isopropyl-p-D-thiogalactopyranoside (IPTG), plasmid-borne ClfAN2N3 were induced with 0.6% arabinose, between an optical density OD$_{600\ nm}$ of 0.86 and 0.96.

After overnight induction at 37° C., cells were harvested and the CP8-ClfAN2N3 bioconjugates were extracted by a periplasmic preparation using a lysis buffer (30 mM Tris-HCl pH 8.5, 1 mM EDTA, 20% (w/v) sucrose) supplemented with 1 mg/ml lysozyme. Periplasmic proteins were collected from the supernatant after centrifugation, loaded on a 4-12% SDS-PAGE and blotted onto a nitrocellulose membrane and detected with an anti-Histidine tag antibody. Proteins loaded were normalized for the optical density of the cells. The results are shown in FIG. 10.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are hereby incorporated in their entireties

---

The invention claimed is:

1. A polypeptide comprising the amino acid sequence of SEQ ID NO: 3 or an amino acid sequence at least 95% identical to SEQ ID NO:3, modified in that the amino acid sequence comprises at least one consensus sequence selected from: KDQNATK (SEQ ID NO: 23) and KDQNRTK (SEQ ID NO: 24); wherein said consensus sequence has been substituted for the amino acid residue Q327, D329, P331 or I337 of SEQ ID NO: 3 or at an equivalent position within the amino acid sequence at least 95% identical to SEQ ID NO: 3.

2. The polypeptide of claim 1, wherein the amino acid sequence further comprises at least one amino acid substitution selected from P116S and Y118A within the amino acid sequence of SEQ ID NO: 3 or at an equivalent position within the amino acid sequence at least 95% identical to SEQ ID NO: 3.

3. The polypeptide according to claim 2, wherein the at least one consensus sequence is substituted for the amino acid residue I337 in SEQ ID NO: 3, or at an equivalent position within the amino acid sequence at least 95% identical to SEQ ID NO: 3.

4. The polypeptide of claim 1, which has an additional serine residue at the N-terminus and an amino acid sequence at least 97% identical to SEQ ID NO: 12 and/or an additional glycine or glycine-serine residue at the C-terminus.

5. The polypeptide of claim 1, wherein the amino acid sequence further comprises a signal sequence which is capable of directing the polypeptide to the periplasm of a host cell, said signal sequence being selected from SEQ ID NOs: 13-20.

6. The polypeptide of claim 1, wherein the amino acid sequence further comprises a peptide tag which is useful for purification of the polypeptide, said peptide tag comprising six histidine residues and being located at the C-terminus of the amino acid sequence.

7. The polypeptide of claim 1, wherein the polypeptide is glycosylated.

8. An immunogenic composition comprising the polypeptide of claim 1, or a conjugate or bioconjugate comprising said polypeptide.

9. A method of making the immunogenic composition of claim 8, the method comprising the step of mixing the polypeptide or the conjugate or the bioconjugate comprising the polypeptide with a pharmaceutically acceptable excipient or carrier.

10. The immunogenic composition of claim 8 further comprising a pharmaceutically acceptable excipient or carrier.

11. A method of inducing an immune response to *Staphylococcus aureus* in a mammalian subject, the method comprising administering the mammalian subject an immunologically effective amount of the polypeptide of claim 1.

12. The polypeptide of claim 1, wherein said polypeptide comprises the amino acid sequence of any one of SEQ ID NOs: 10-12.

13. The polypeptide of claim 1, wherein said polypeptide has an amino acid sequence at least 97% identical to SEQ ID No: 32.

14. The polypeptide of claim 1, wherein said polypeptide comprises an amino acid sequence at least 97% identical to SEQ ID NOs: 11.

15. The polypeptide of claim 1, wherein said polypeptide has an amino acid sequence at least 97% identical to SEQ ID No: 25, SEQ ID NO: 26, or SEQ ID NO: 27.

* * * * *